(12) United States Patent
Monroe et al.

(10) Patent No.: US 11,484,553 B2
(45) Date of Patent: Nov. 1, 2022

(54) DOMINANT ACTIVE YAP, A HIPPO EFFECTOR, INDUCES CHROMATIN ACCESSIBILITY AND CARDIOMYOCYTE RENEWAL

(71) Applicant: Baylor College of Medicine, Houston, TX (US)

(72) Inventors: Tanner Monroe, Houston, TX (US); John Leach, Houston, TX (US); James F. Martin, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 341 days.

(21) Appl. No.: 16/491,491

(22) PCT Filed: Mar. 14, 2018

(86) PCT No.: PCT/US2018/022496
§ 371 (c)(1),
(2) Date: Sep. 5, 2019

(87) PCT Pub. No.: WO2018/170172
PCT Pub. Date: Sep. 20, 2018

(65) Prior Publication Data
US 2020/0016212 A1    Jan. 16, 2020

Related U.S. Application Data

(60) Provisional application No. 62/471,204, filed on Mar. 14, 2017.

(51) Int. Cl.
| | | |
|---|---|---|
| C07H 21/04 | (2006.01) | |
| C07H 21/02 | (2006.01) | |
| A61K 35/34 | (2015.01) | |
| C07K 14/47 | (2006.01) | |
| C12N 5/077 | (2010.01) | |
| A61K 48/00 | (2006.01) | |
| A01K 67/027 | (2006.01) | |
| A61K 38/00 | (2006.01) | |

(52) U.S. Cl.
CPC .............. *A61K 35/34* (2013.01); *A61K 48/00* (2013.01); *C07K 14/4702* (2013.01); *C12N 5/0657* (2013.01); *A01K 67/0278* (2013.01); *A01K 2217/072* (2013.01); *A01K 2227/105* (2013.01); *A01K 2267/0375* (2013.01); *A61K 38/00* (2013.01)

(58) Field of Classification Search
CPC .......................... C07K 14/4702; A61K 48/00
See application file for complete search history.

(56) References Cited

U.S. PATENT DOCUMENTS

| | | |
|---|---|---|
| 2009/0312251 A1 | 12/2009 | Lim et al. |
| 2014/0107189 A1 | 4/2014 | Bancel et al. |
| 2016/0287724 A1 | 10/2016 | Rosenzweig et al. |
| 2016/0361340 A1 | 12/2016 | Meilhac et al. |

FOREIGN PATENT DOCUMENTS

| | | | |
|---|---|---|---|
| WO | 2016/044096 A1 | 3/2016 | |
| WO | WO 2020/115039 A1 * | 6/2020 | ............ C12N 15/111 |

OTHER PUBLICATIONS

Sudol et al. (The Journal of Biological Chemistry, 270, 24, 14733-14741, 1995).*
He, Mingjing et al. "New insights into posttranslational modifications of Hippo pathway in carcinogenesis and therapeutics", Cell Division, vol. 11, No. 1, Mar. 1, 2016.
Lin et al.: "Cardiac-Specific YAP Activation Improves Cardiac Function and Survival in an Experimental Murine MI Model", Circulation Research, vol. 115, No. 3, Jul. 18, 2014 (Jul. 18, 2014), pp. 354-363.
Von Gise et al.: "YAPI, the nuclear target of Hippo signaling, stimulates heart growth through cardiomyocyte proliferation but not hypertrophy", Proceedings of the National Academy of Sciences, vol. 109, No. 7, Jan. 30, 2012 (Jan. 30, 2012), pp. 2394-2399.
Yang et al.: "Hippo/Yap Signaling in 1-10 Cardiac Development and Regeneration", Current Treatment Dptions in Cardiovascular Medicine, Current Science Inc., Philadelphia, PA, US, vol. 18, No. 6, Apr. 4, 2016 (Apr. 4, 2016), pp. 1-9.
Zhao et al.: "A coordinated phosphorylation by Lats and CKI regulates YAP stability through SCF-TRCP", Genes & Development, vol. 24, No. I, Jan. 1, 2010 (Jan. 1, 2010), pp. 72-85.
Zhao et al.: "Both TEAD-Binding and WW 1-10 Domains Are Required for the Growth Stimulation and Oncogenic Transformation Activity of Yes-Associated Protein", Cancer Research, vol. 69, No. 3, Jan. 20, 2009 (Jan. 20, 2009), pp. 1089-1098.
Lin et al. , "Harnessing Hippo in the heart: Hippo/Yap signaling and applications to head regeneration and rejuvenation" Cell Res. 2014, vol. 13(3 Pt B). p. 571-81.

(Continued)

*Primary Examiner* — Amy H Bowman
(74) *Attorney, Agent, or Firm* — Norton Rose Fulbright US LLP

(57) ABSTRACT

The present disclosure encompasses methods for generating cells or tissue from existing cells with one or more mutated variants of Yap. In specific embodiments, the disclosure regards treatment of existing cardiomyocytes with one or more mutated variants of Yap that causes them to divide and generate new cardiomyocytes. In specific cases, the mutated variant of Yap has serine-to-alanine substitutions at 1, 2, 3, 4, 5, 6, or more serines of Yap.

7 Claims, 31 Drawing Sheets

Specification includes a Sequence Listing.

(56) References Cited

OTHER PUBLICATIONS

Xin et al., "Hippo pathway effector Yap promotes cardiac regeneration", Proc Natl Acad Sci USA. 2013, vol. 110(34). p. 13839-44.
Juan et al., "Targeting the Hippo Signaling Pathway for Tissue Regeneration and Cancer Therapy" Genes (Basel). 2016, vol. 7(9). pii: E55.
Judson et al., "Constitutive Expression of Yes-Associated Protein (Yap) in Adult Skeletal Muscle Fibres Induces Muscle Atrophy and Myopathy" PLoS One. 2013, vol. 8(3):e59622.

* cited by examiner

```
  1  MDPGQQPPPQPAPQGQGQPPSQPPQGQGPPSGPGQPAPAATQAAPQAPPAGHQIVHVRGD
 61  SETDLEALFNAVMNPKTANVPQTVPMRLRKLPDSFFKPPEPKSHSRQASTDAGTAGALTP
121  QHVRAHSSPASLQLGAVSPGTLTPTGVVSGPAATPTAQHLRQSSFEIPDDVPLPAGWEMA
181  KTSSGQRYFLNHIDQTTTWQDPRKAMLSQMNVTAPTSPPVQQNMMNSASGPLPDGWEQAM
241  TQDGEIYYINHKNKTTSWLDPRLDPRFAMNQRISQSAPVKQPPPLAPQSPQGGVMGGSNS
301  NQQQQMRLQQLQMEKERLRLKQQELLRQELALRSQLPTLEQDGGTQNPVSSPGMSQELRT
361  MTTNSSDPFLNSGTYHSRDESTDSGLSMSSYSVPRTPDDFLNSVDEMDTGDTINQSTLPS
421  QQNRFPDYLEAIPGTNVDLGTLEGDGMNIEGEELMPSLQEALSSDILNDMESVLAATKLD
481  KESFLTWL (SEQ ID NO: 1)
```

Lats phosphorylation motif: HXRXXS

FIG. 1A

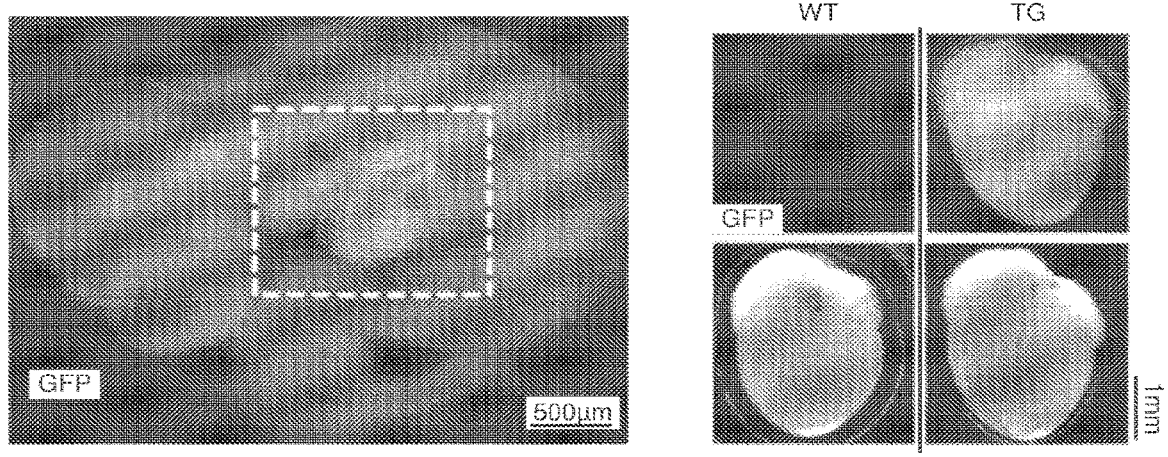

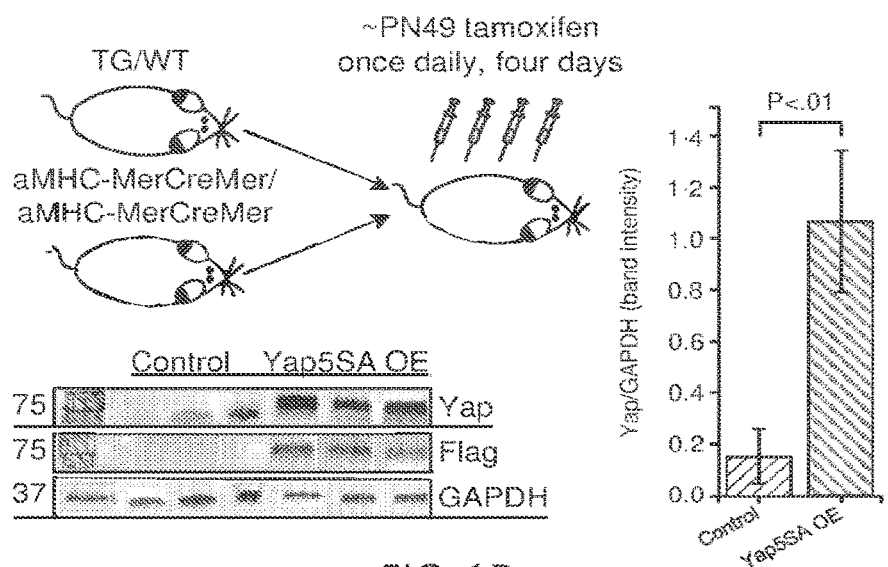

FIG. 1D $\log_2 N(t) = 1.4633t - 4.7005$
$R^2 = 0.95981$
$t_0 = 1.37$ days $N(t) = N_0 2^{2t/1.37}$ Days after tamoxifen

| Proportion with inverted T wave | | |
|---|---|---|
|  | Control | Yap5SA OE |
| Pre-tamoxifen | 0/3 | 0/4 |
| Post-tamoxifen | 3/3* | 0/4 |

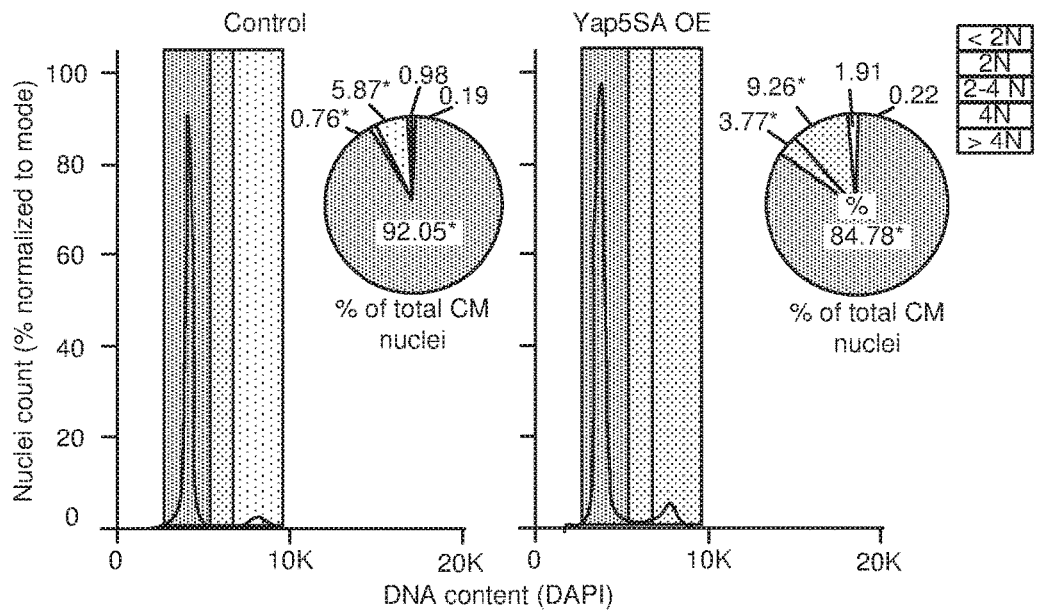
FIG. 6A
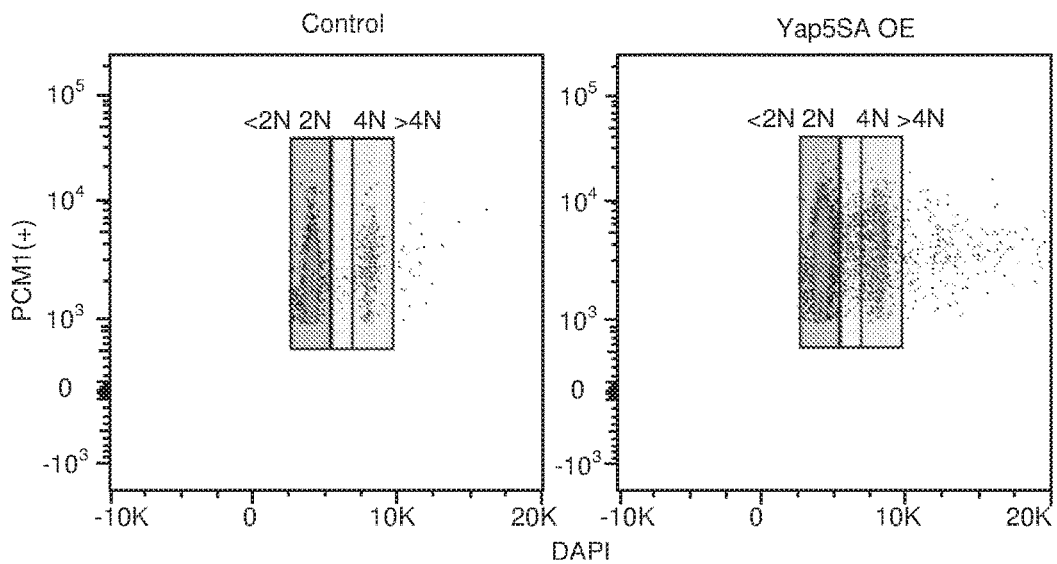
FIG. 6B
| | % nuclei <2N | +/- | % nuclei 2N | +/- | % nuclei 2-4N | +/- | % nuclei 4N | +/- | % nuclei >4N | +/- |
|---|---|---|---|---|---|---|---|---|---|---|
| Control | 0.19 | 0.01 | 92.05 | 0.24 | 0.76 | 0.38 | 5.87 | 0.04 | 0.98 | 0.65 |
| Yap5SA OE | 0.22 | 0.70 | 84.78 | 0.46 | 3.77 | 0.31 | 9.26 | 0.95 | 1.91 | 0.62 |
| P | 0.63 | | 0.001 | | 0.005 | | 0.005 | | 0.11 | |
FIG. 6C RNA-seq (up), ChIP-seq (+), ATAC-seq (no change)

| log2(FC)S | Gene | log2(FC) | Adjusted P | Gene | log2(FC) | Adjusted P |
|---|---|---|---|---|---|---|
| 0.00 | Adamts5 | 2.48 | 5.98E-19 | Dbf4 | 1.20 | 1.29E-03 |
| 10.00 | Tmem97 | 2.68 | 1.28E-15 | Sulf1 | 1.05 | 1.36E-03 |
| | Actn1 | 1.75 | 2.55E-12 | Pacsin2 | 0.97 | 1.73E-03 |
| | Usp31 | 1.68 | 9.68E-09 | Il17ra | 1.33 | 1.96E-03 |
| | 2310022B05 | 1.75 | 3.28E-08 | Piezo1 | 0.95 | 1.97E-03 |
| | Wsb1 | 1.58 | 3.80E-08 | Mlana | 1.90 | 2.07E-03 |
| | Ajuba | 1.61 | 3.81E-08 | Was | 1.47 | 2.11E-03 |
| | Gria3 | 2.09 | 3.90E-08 | Hes1 | 1.06 | 2.71E-03 |
| | Peak1 | 1.43 | 4.49E-08 | Mfhas1 | 1.00 | 2.83E-03 |
| | S100a7a | 3.05 | 2.68E-07 | Spry2 | 1.02 | 2.86E-03 |
| | Prkcz | 2.28 | 3.88E-07 | Ryr3 | 1.68 | 2.94E-03 |
| | Fcgr1 | 1.77 | 1.25E-06 | Fzd2 | 1.28 | 3.02E-03 |
| | Kcnab2 | 1.77 | 1.64E-06 | Numbl | 1.40 | 3.13E-03 |
| | Hist1h4f | 1.66 | 1.95E-06 | Pard6b | 1.03 | 3.25E-03 |
| | Ret | 2.19 | 3.30E-06 | Itsn1 | 1.10 | 3.34E-03 |
| | Adgre1 | 1.55 | 3.99E-06 | Capg | 1.18 | 3.58E-03 |
| | Efemp1 | 1.76 | 7.17E-06 | Lacc1 | 1.33 | 3.80E-03 |
| | Pik3cg | 1.62 | 1.19E-05 | Fam105a | 1.33 | 4.36E-03 |
| | Lyn | 1.33 | 1.20E-05 | Sptb | 0.98 | 4.37E-03 |
| | Plod2 | 1.92 | 1.51E-05 | Incenp | 1.11 | 4.52E-03 |
| | Ms4a7 | 1.99 | 1.73E-05 | Wnt9a | 1.19 | 4.62E-03 |
| | Cpox | 1.44 | 2.67E-05 | Atic | 1.03 | 4.71E-03 |
| | Dock8 | 1.33 | 2.82E-05 | Aprt | 1.10 | 4.78E-03 |
| | Rras2 | 1.49 | 5.06E-05 | Kntc1 | 1.26 | 4.78E-03 |
| | Cfap43 | 1.36 | 8.16E-05 | Hexb | 1.07 | 4.79E-03 |
| | Chn1 | 1.35 | 8.76E-05 | Tnfaip6 | 1.39 | 4.80E-03 |
| | Basp1 | 1.61 | 1.34E-04 | Amhr2 | 1.77 | 5.07E-03 |
| | Rhobtb3 | 1.12 | 1.45E-04 | Slc7a2 | 1.13 | 5.11E-03 |
| | Phldb3 | 2.16 | 1.48E-04 | Ifi44 | 1.67 | 5.39E-03 |
| | Nhlrc1 | 1.66 | 1.75E-04 | Plk1 | 1.22 | 5.69E-03 |
| | Ddb1 | 1.19 | 1.76E-04 | Map4k3 | 0.91 | 5.69E-03 |
| | Ppp1r3a | 1.15 | 1.77E-04 | E2f1 | 1.36 | 5.69E-03 |
| | Noct | 1.09 | 2.35E-04 | Epdr1 | 1.14 | 5.70E-03 |
| | Hk3 | 1.62 | 2.49E-04 | Rcan2 | 1.38 | 5.76E-03 |
| | Abca4 | 1.37 | 2.52E-04 | Bmp2k | 0.88 | 6.31E-03 |
| | Rgma | 1.17 | 2.68E-04 | 1600014C10 | 1.14 | 6.97E-03 |
| | Prep | 1.15 | 3.08E-04 | Dusp10 | 1.35 | 6.99E-03 |
| | Ifngr2 | 1.13 | 4.30E-04 | Iqsec1 | 0.91 | 7.24E-03 |
| | Mki67 | 1.23 | 5.28E-04 | P4ha1 | 1.07 | 7.27E-03 |
| | Atp8b4 | 1.47 | 5.56E-04 | Pde3b | 1.05 | 7.79E-03 |
| | E2f2 | 1.87 | 5.56E-04 | Rap1b | 0.88 | 8.12E-03 |
| | Cd53 | 1.27 | 6.75E-04 | Fap | 1.35 | 8.25E-03 |
| | Ect2 | 1.27 | 6.79E-04 | Terc | 1.52 | 8.82E-03 |
| | Myo1g | 1.45 | 6.98E-04 | Nup210 | 1.13 | 9.70E-03 |
| | Endod1 | 1.15 | 7.66E-04 | | | |
| | Rock2 | 0.95 | 9.05E-04 | | | |
| | Cd28 | 2.16 | 9.73E-04 | | | |
| | Rps6ka5 | 1.28 | 9.93E-04 | | | |
| | Corb2 | 1.37 | 1.05E-03 | | | |
| | Ccna2 | 1.28 | 1.06E-03 | | | |
| | Il33 | 1.29 | 1.09E-03 | | | |
| | Atp13a3 | 1.00 | 1.28E-03 | | | |
| | Rps6ka1 | 1.23 | 1.54E-03 | | | |

FIG. 13A.1

RNA-seq (up), ChIP-seq (-), ATAC-seq (+)

| log2(FC)S | Gene | log2(FC) | padj | Gene | log2(FC) | padj |
|---|---|---|---|---|---|---|
| 0.00 | Plcxd2 | 4.21 | 3.48E-57 | Pvt1 | 1.75 | 9.91E-05 |
| 10.00 | Serpinb9b | 5.16 | 1.20E-49 | Tnfaip3 | 1.38 | 1.17E-04 |
| | Tnfsf15 | 6.14 | 1.73E-44 | Klhl8 | 1.26 | 1.22E-04 |
| | Lrtm2 | 5.24 | 1.29E-40 | Stard13 | 1.45 | 1.34E-04 |
| | Frmpd1 | 5.40 | 4.05E-32 | Cdc42se2 | 1.15 | 1.55E-04 |
| | Tnfsf18 | 4.26 | 4.19E-28 | Cacul1 | 1.16 | 1.57E-04 |
| | Slc24a3 | 3.64 | 3.72E-24 | Tmpo | 1.14 | 1.58E-04 |
| | Vnn1 | 4.95 | 8.58E-23 | Lgals9 | 1.25 | 2.28E-04 |
| | Krt7 | 3.95 | 9.37E-22 | Cacna1s | 2.16 | 2.47E-04 |
| | Gpc4 | 2.62 | 4.23E-21 | Sipa1l3 | 1.15 | 2.99E-04 |
| | Itga3 | 2.27 | 5.98E-19 | Mras | 1.60 | 3.41E-04 |
| | Prss23 | 2.48 | 1.86E-18 | A430105I19 | 1.09 | 4.21E-04 |
| | Abhd17c | 2.37 | 8.28E-18 | Sned1 | 1.15 | 4.48E-04 |
| | Dcun1d4 | 2.46 | 5.08E-17 | Tamm41 | 1.38 | 5.23E-04 |
| | Tsku | 2.35 | 6.58E-17 | Mrpl39 | 1.15 | 5.93E-04 |
| | Morc4 | 2.73 | 4.31E-16 | 1700037HC | 1.37 | 6.70E-04 |
| | Sema3e | 3.45 | 1.26E-15 | Dse | 1.21 | 8.24E-04 |
| | Amotl2 | 1.93 | 3.24E-15 | Dlc1 | 1.05 | 1.18E-03 |
| | Rtn4r | 2.86 | 6.83E-14 | Lpcat2 | 1.55 | 1.22E-03 |
| | Plekhg2 | 2.05 | 2.50E-13 | Slc35b4 | 1.10 | 1.28E-03 |
| | Ctdspl | 2.07 | 2.22E-12 | Snx30 | 1.53 | 1.58E-03 |
| | Ngfrap1 | 2.47 | 2.70E-10 | Ergic1 | 0.99 | 1.71E-03 |
| | Map6 | 2.30 | 3.92E-10 | Rrm1 | 1.10 | 1.81E-03 |
| | Nhs | 2.17 | 3.81E-08 | Capn2 | 1.10 | 1.96E-03 |
| | Tbc1d23 | 1.54 | 4.78E-08 | Lrtm1 | 1.04 | 2.06E-03 |
| | Dock5 | 1.59 | 7.30E-08 | Upk3b | 1.48 | 2.14E-03 |
| | Tmem37 | 2.76 | 8.97E-08 | Cenpe | 1.21 | 2.21E-03 |
| | Figf | 2.18 | 1.09E-07 | Sema6d | 0.99 | 2.42E-03 |
| | Pxdc1 | 1.59 | 1.93E-07 | Sh3gl1 | 1.02 | 2.47E-03 |
| | Cdc42ep3 | 1.63 | 3.22E-07 | Gls | 0.90 | 2.71E-03 |
| | Ero2 | 2.48 | 9.38E-07 | Ube2e1 | 1.07 | 2.90E-03 |
| | Hs6st2 | 1.95 | 1.11E-06 | Creb3 | 1.10 | 3.02E-03 |
| | Sdpr | 1.59 | 1.15E-06 | Arhgap1 | 1.21 | 3.21E-03 |
| | Ube2ql | 1.47 | 1.21E-06 | Amst | 1.21 | 3.26E-03 |
| | Ins c | 2.99 | 1.20E-06 | Slfn2 | 1.11 | 3.52E-03 |
| | Serpinb6b | 1.91 | 1.29E-06 | Osbpl5 | 1.00 | 3.66E-03 |
| | Mpnp | 1.29 | 1.59E-03 | Mrvi1 | 1.09 | 3.77E-03 |
| | Tns3 | 1.30 | 1.64E-06 | Fam72a | 1.76 | 3.79E-03 |
| | Ccl2 | 1.73 | 2.28E-06 | Apls3 | 1.94 | 3.80E-03 |
| | Mbp | 1.89 | 3.66E-06 | Ifit2 | 1.17 | 3.82E-03 |
| | Slc7a8 | 1.81 | 5.65E-06 | Dram1 | 1.25 | 4.34E-03 |
| | Ari5a | 1.31 | 6.07E-06 | Cacnb4 | 1.41 | 4.79E-03 |
| | Gm4841 | 2.81 | 6.34E-06 | Fam134b | 0.67 | 5.07E-03 |
| | Phldb2 | 2.09 | 7.42E-06 | A330015K0 | 1.81 | 5.35E-03 |
| | Prelp | 1.42 | 7.65E-06 | Vim | 0.98 | 6.10E-03 |
| | Rnd3 | 1.38 | 8.16E-06 | Zdhhc14 | 1.06 | 6.83E-03 |
| | Fgfrl1 | 1.57 | 8.66E-06 | Rasl11a | 1.47 | 6.99E-03 |
| | Adamtsl3 | 1.51 | 1.31E-05 | Lig1 | 1.05 | 7.16E-03 |
| | Vgll4 | 1.36 | 2.70E-05 | AI467606 | 1.71 | 7.23E-03 |
| | Spg20 | 1.21 | 3.15E-05 | Rprd1a | 1.04 | 7.63E-03 |
| | Aqp4 | 2.13 | 4.64E-05 | Nuak2 | 1.05 | 7.82E-03 |
| | Ch25h | 2.00 | 7.04E-05 | Cond1 | 1.09 | 8.45E-03 |
| | Ddr1 | 1.22 | 8.60E-05 | Bank1 | 1.71 | 8.82E+00 |

FIG. 13A.2

RNA-seq (up), ChIP-seq (-), ATAC-seq (+)

| log2(FC)S | Gene | log2(FC) | padj | Gene | log2(FC) | padj |
|---|---|---|---|---|---|---|
| 0.00 | Cemip | 7.03 | 2.24E-150 | Snap91 | 1.44 | 1.71E-03 |
| 10.00 | Col4a3 | 4.70 | 1.45E-54 | Bdnf | 1.80 | 2.13E-03 |
| | Col4a4 | 3.68 | 1.47E-54 | Nog | 2.20 | 2.42E-03 |
| | Cobl | 3.55 | 1.38E-37 | C1galt1 | 0.96 | 2.60E-03 |
| | Wwc1 | 4.60 | 6.50E-36 | Ccdc71l | 1.06 | 2.64E-03 |
| | Csf1 | 3.10 | 3.68E-27 | Secisbp2l | 0.92 | 2.79E-03 |
| | Arhgef16 | 3.89 | 1.37E-21 | Rbms3 | 0.95 | 3.13E-03 |
| | Klhdc8a | 2.82 | 1.54E-19 | Zfhx3 | 0.91 | 3.31E-03 |
| | Ctnnd2 | 4.15 | 2.27E-19 | Mtss1 | 1.13 | 3.32E-03 |
| | Il23r | 4.39 | 1.98E-17 | Fndc1 | 0.97 | 3.61E-03 |
| | Ildr2 | 2.57 | 1.07E-16 | Cnn3 | 1.09 | 4.06E-03 |
| | Plekha7 | 2.40 | 9.16E-16 | Prickle1 | 1.01 | 4.05E-03 |
| | Igfbp2 | 4.14 | 5.85E-15 | Snx2 | 1.00 | 4.13E-03 |
| | Gng12 | 2.17 | 1.07E-13 | Veph1 | 2.08 | 4.57E-03 |
| | Arhgef26 | 2.39 | 1.07E-13 | Prkd1 | 2.08 | 4.57E-03 |
| | Ctsc | 1.65 | 6.71E-11 | Sptan1 | 0.85 | 7.16E-03 |
| | Adcy6 | 2.60 | 1.08E-09 | Tbx18 | 1.07 | 7.34E-03 |
| | Epb41l3 | 2.13 | 1.67E-09 | Atp10a | 1.15 | 7.34E-03 |
| | Pak3 | 2.77 | 2.24E-09 | Dchs2 | 0.93 | 7.48E-03 |
| | Vgll3 | 1.76 | 3.05E-09 | Ankrd44 | 0.96 | 7.55E-03 |
| | Pgm2 | 1.68 | 6.33E-08 | Vgll2 | 1.95 | 8.09E-03 |
| | Dab2 | 1.44 | 1.00E-07 | Fat3 | 1.61 | 9.04E-03 |
| | Slc1a3 | 1.78 | 1.96E-07 | Pvrl1 | 1.10 | 9.05E-03 |
| | 1190002N15 | 2.45 | 3.37E-07 | | | |
| | Fam178a | 1.43 | 3.38E-07 | | | |
| | Nav3 | 1.51 | 3.65E-07 | | | |
| | Msr1 | 1.88 | 3.95E-07 | | | |
| | Crim1 | 1.59 | 5.64E-07 | | | |
| | Prkci | 1.52 | 1.05E-06 | | | |
| | Alcam | 1.88 | 2.26E-06 | | | |
| | Ptchd4 | 2.72 | 3.16E-06 | | | |
| | Htra1 | 1.75 | 3.55E-06 | | | |
| | Fmn1 | 1.46 | 3.89E-06 | | | |
| | Frmd4a | 1.48 | 8.35E-06 | | | |
| | Tmsb10 | 1.40 | 1.26E-05 | | | |
| | Pdpn | 1.62 | 1.30E-05 | | | |
| | Cpne2 | 1.70 | 1.87E-05 | | | |
| | Asap1 | 1.17 | 4.35E-05 | | | |
| | Lats2 | 1.14 | 5.11E-05 | | | |
| | Sdk1 | 1.90 | 5.49E-05 | | | |
| | Arnt2 | 2.10 | 1.08E-04 | | | |
| | Snx7 | 1.30 | 1.68E-04 | | | |
| | Txndc5 | 1.13 | 3.14E-04 | | | |
| | Pappa | 1.28 | 5.39E-04 | | | |
| | Itgb6 | 1.69 | 5.44E-04 | | | |
| | S100a10 | 1.51 | 5.45E-04 | | | |
| | Cited2 | 1.20 | 5.63E-04 | | | |
| | Mme | 1.48 | 6.91E-04 | | | |
| | Itga4 | 1.34 | 8.24E-04 | | | |
| | Wls | 1.10 | 9.03E-04 | | | |
| | Klf5 | 1.94 | 1.24E-03 | | | |
| | Zeb2 | 1.04 | 1.58E-03 | | | |
| | Spc24 | 1.54 | 1.69E-03 | | | |

FIG. 13A.3

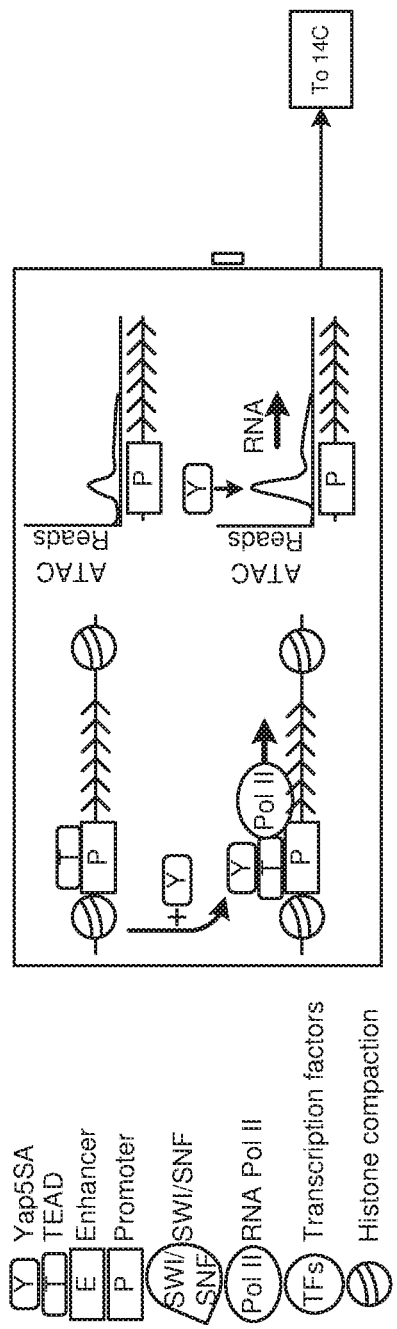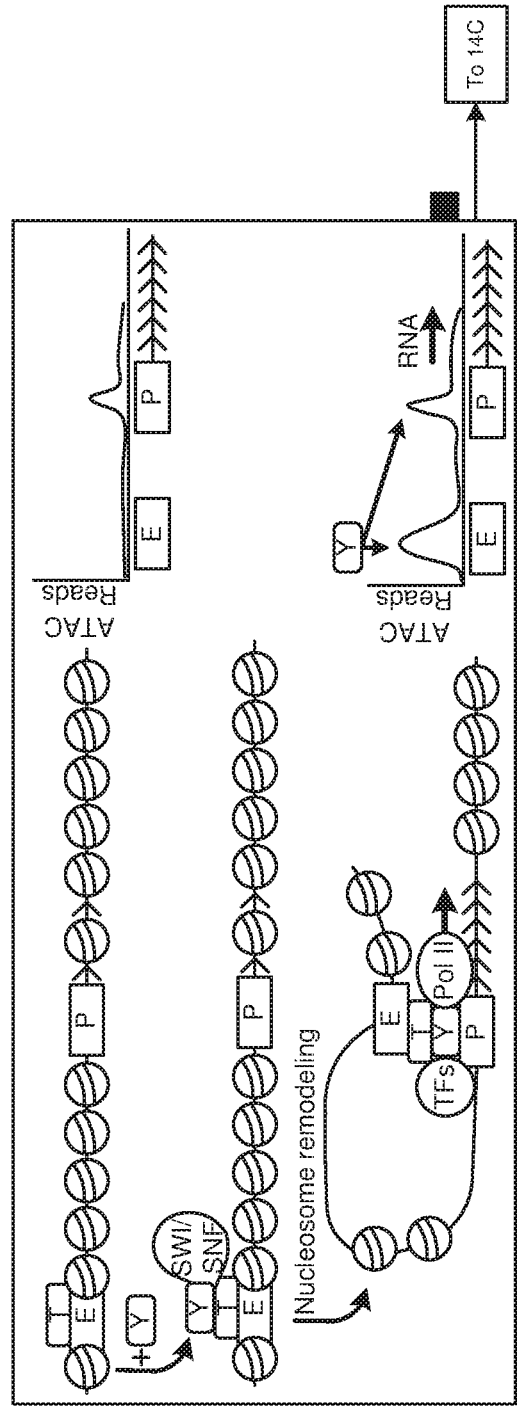
FIG. 14A
FIG. 14B

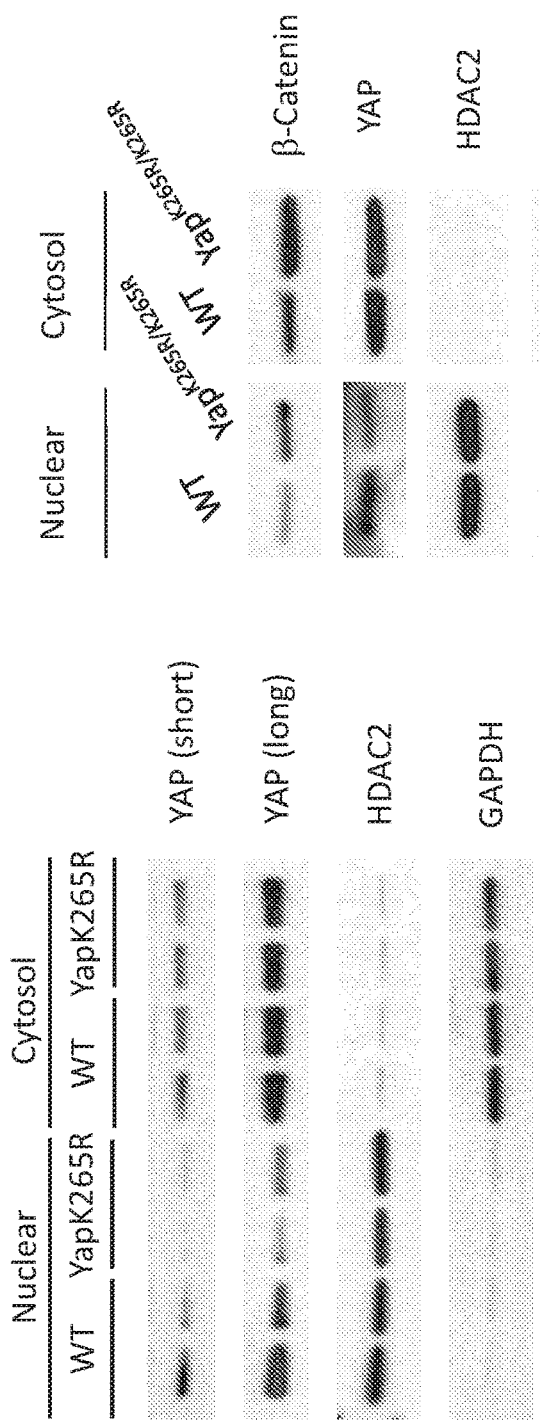
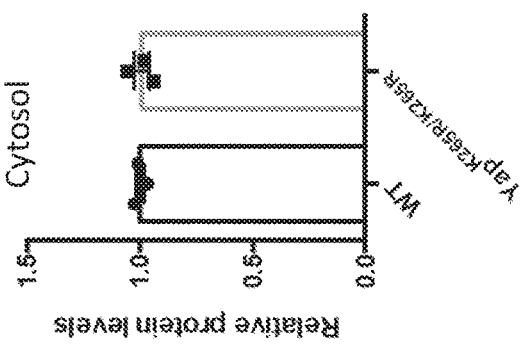
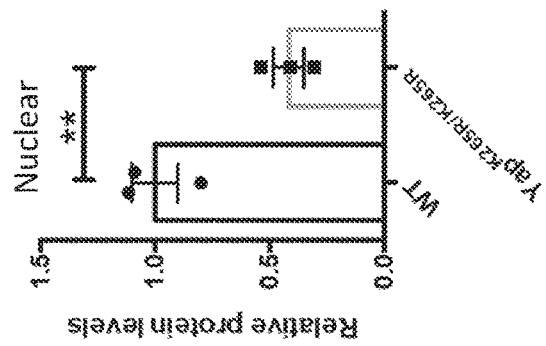
FIG. 19A
FIG. 19B
FIG. 19C
FIG. 19D

DOMINANT ACTIVE YAP, A HIPPO EFFECTOR, INDUCES CHROMATIN ACCESSIBILITY AND CARDIOMYOCYTE RENEWAL

The present application is a national phase application under 35 U.S.C. § 371 that claims priority to International Application No. PCT/US2018/022496 filed Mar. 14, 2018, which claims priority to U.S. Provisional Patent Application 62/471,204, filed Mar. 14, 2017, both of which are incorporated by reference herein in their entirety.

The instant application contains a Sequence Listing which has been submitted electronically in ASCII format and is hereby incorporated by reference in its entirety. Said ASCII copy, created on Jul. 18, 2018, is named BAYM_P0223W0_SL.txt and is 16,265 bytes in size.

STATEMENT REGARDING FEDERALLY SPONSORED RESEARCH OR DEVELOPMENT

This invention was made with government support under HL 127717 awarded by National Institutes of Health (NIH). The government has certain rights in the invention.

TECHNICAL FIELD

Embodiments of the disclosure concern at least the fields of cell biology, molecular biology, biochemistry, cardiology, and medicine.

BACKGROUND $C^{14}$ dating experiments indicated that the complete supply of human cardiomyocytes is established within the first month of life and adult cardiomyocytes renew at approximately 1% per year[1]. Adult mouse cardiomyocytes have similarly low rates of renewal[2]. The Hippo pathway is an evolutionarily conserved kinase cascade that results in the phosphorylation and inhibition of the transcriptional co-activator, Yap, by the Large Tumor Suppressor (Lats)1 and 2 kinases[3]. Postnatal deletion of Hippo pathway components can modestly increase CM renewal, as can expressing an active form of Yap with a single Serine (S) to Alanine (A) mutation[4-7].

Lats1/2 inhibits Yap by phosphorylating S residues at five consensus NDR (nuclear Dbf2-related) kinase family motifs, HXRXXS. In vitro reporter assays have shown that while much of Hippo inhibition is through S127 phosphorylation (S127 in humans, S112 in mice), the other S phosphorylation events also contribute to Yap inhibition[8].

The present disclosure satisfies a longfelt need in the art of cardiomyocyte renewal including for cardiac repair.

BRIEF SUMMARY

Embodiments of the disclosure include methods and compositions for tissue renewal of any kind, including in the heart, retina, neurons of the central nervous system, and hair cells of the ear, for example. Embodiments of the disclosure include methods and compositions related to regeneration of cells including for the therapy for one or more conditions in a mammalian individual such as a human, dog, cat, horse, and so forth. Embodiments of the disclosure include methods and compositions for regenerating cells in one or more individuals in need thereof. The individual may have any kind of condition in need of cell regeneration or is susceptible or at risk thereto. In specific embodiments, there is provided methods and compositions related to regeneration of cardiomyocytes, retinal cells, neurons of the central nervous system, or hair cells of the ear (including inner or outer), including for the therapy for one or more conditions in a mammalian individual. In specific cases for the retina, Yap mutant is exposed to Muller glial cells so that they will differentiate into neurons of the retina. In the case of regeneration of cardiomyocytes the individual may have or be at risk for a cardiac condition. An individual may be at risk for a cardiac condition because of a personal and/or family history, because they are a smoker, because they are obese or overweight, a combination thereof, and so forth.

In specific embodiments, the methods and compositions concern one or more mutants of Yap. In certain embodiments, one or more mutants of Yap have an activity of promoting cell (including cardiomyocyte retinal cells, neurons of the central nervous system, or hair cells of the ear) renewal that leads to improvement of any related medical condition. In alternative embodiments, the one or more Yap mutants improve any medical condition but do not detectably promote cell renewal. In specific embodiments, however, one or more Yap mutants stimulates global chromatin reorganization to promote cell renewal. In specific cases, the mutant is a Yap mutant having 1, 2, 3, 4, 5, 6, or more amino acid substitutions. The substitution may or may not be at a serine and in some cases the substitution is that of an amino acid to alanine. In particular aspects, a mutant having five serine to alanine substitutions at the main phosphorylation sites for Lats kinases, Yap5SA, in adult cardiomyocytes stimulates global chromatin reorganization to promote cardiomyocyte renewal, as an example. Such a Yap mutant or other Yap mutants may analogously be used to promote retinal or hair cell renewal. The Yap mutant may be provided to an individual as a polynucleotide or a polypeptide.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 1A-1E. Design and expression of the Yap5SA transgene. FIG. 1A. (Top) Structure of the conditional Yap5SA allele. (Bottom) Human protein sequence of the Yap variant that was overexpressed with the underlined serine residues mutated to alanine FIG. 1B. Representative e9.5 Tg (Jojo_Flag::Yap5SA)5JFM mouse with GFP expression in the developing heart. FIG. 1C. Images of GFP fluorescence in control and transgenic hearts taken from P0 neonates. FIG. 1D. (Top left) Breeding and induction strategy to express the Yap5SA in adult CMs. (Bottom left) Western Blot showing FlagYap5SA expression. Molecular weight markers on the left. (Right) Quantification of Yap expression by western blot is shown as mean+/−SEM. n=3 mice/genotype. FIG. 1E. Immunofluorescent images of isolated control and Yap5SA OE cardiomyocytes stained with an anti-Yap antibody and DAPI. (Right) Quantification of nuclear/cytosolic ratio of Yap immunofluorescence shown as mean+/−SEM. All statistics by ANOVA with Bonferroni post-hoc tests. Control n=3 hearts, 60 cells. Yap5SA n=3 hearts, 67 cells;

FIG. 2A. Kaplan Meier survival analysis representing control (n=8) and Yap5SA OE (n=7) mice. Statistics computed by Mantel-Cox test. FIG. 2B. Masson's trichrome from control and moribund-stage Yap5SA hearts (day 7). FIG. 2C. Representative B-Mode images of left ventricle in the same animal before and one day after the fourth tamoxifen injection. FIGS. 2D-2E. Left ventricle posterior free wall thickness, in systole (FIG. 2D) and diastole (FIG. 2E). FIGS. 2D-2E Shown as mean+/−SEM. (Before Yap5SA n=7, before Con n=6, Post Yap5SA n=10, Post Con n=9) statistics computed by ANOVA with post-hoc Bonferroni tests. FIG. 2F Representative M-mode echocardiography of control and a Yap5SA OE hearts, before and one day after the fourth tamoxifen injection. FIG. 2G. End systolic left ventricular chamber diameter FIG. 2H. End diastolic left ventricular chamber diameter. FIG. 2I. Fractional shortening FIG. 2J. Ejection fraction. FIGS. 2G-2J Data shown as mean+/−SEM. (Before Yap5SA n=4, before Con n=3, Post Yap5SA n=7, after Con n=7) statistics computed as by ANOVA with post-hoc Bonferroni tests;

FIG. 3A. Histograms indicating area of isolated CMs. n=3 mice/group.~100 cells/heart. FIG. 3B. Sections and area of LV at different tissue depths. n=6/group. Mean+/−SEM. * indicates P<0.05 FIG. 3C. LV volume. FIG. 3D. LV Chamber volume n=6/group. Mean+/−SEM. FIG. 3E. LV weight to body weight ratio (n=6/condition). Mean+/−SEM FIG. 3F. (Left) Myocyte number in LV. (n=5/group) Mean+/−SEM. (Right) PCM1(+) CM nuclei (examples indicated with yellow arrows). FIG. 3G. CM nucleation. 6 hearts/group. 400-500 CMs/heart. Mean+/−SEM. FIG. 3H. (Left) Example EdU-containing CMs. (Right) Induction/EdU labelling strategy and Quantification of EdU incorporation. Mean+/−SEM. n=4 hearts/group. 200-300 CMs/heart. FIG. 3I. Representative AuroraB-stained sections (positive cells indicated with yellow arrows). (Right) Quantification of AuroraB(+) CMs Mean+/−SEM. n=3 mice/group. 200-300 CMs/heart. FIG. 3J. Example PHH3-stained sections (positive cells indicated with yellow arrows). (Right) Quantification of PHH3(+) CMs. Mean+/−SEM. n=3 mice/group 200-300 CMs/heart. FIGS. 3A-3J statistics by ANOVA with post-hoc Bonferroni tests. FIGS. 3A-3J from mice 2 days after the tamoxifen protocol. FIG. 3K. Number of Yap5SA OE lacz(+) CMs after single low dose tamoxifen at different time points Shown in log 2 form (left) and raw (right). Mean+/−SEM. N(t)=number of lacz(+) cells/area myocardium. t=time (days). tD=doubling time. n=3 mice/time point. Linear fit R2=0.96 after log 2 transformation;

FIG. 4A. (Top) CM nuclear enrichment protocol. (Bottom left) Volcano plot of Yap5SA RNA-seq relative to control. 1,352 genes up, 748 down (adjusted P-value<0.1). (Bottom right) Volcano plot of Yap5SA ATAC-seq compared to control. 16,189 peaks up, 13,353 down by significant $log_2$ fold change in Yap5SA. Two samples/genotype. Reproducibility in FIG. 9. FIG. 4B. (Left) Top Yap5SA enriched ATAC-seq motifs. (Right) Nucleosome signal for all TEAD motif peaks, normalized between 0 and 1 (FIG. 4C). Enhancer and promoter proportions of: total intergenic ATAC-seq peaks (FIG. 12); Yap5SA enriched intergenic ATAC-seq peaks; and Yap5SA ChIP-Seq peaks. *P<0.001 relative to control proportions Chi-squared test, Yates correction. FIG. 4D. H3K27Ac fragment coverage from developing and adult hearts centered around the top ATAC-seq peaks (adjusted p<0.035) in either control or Yap5SA OE CMs. n for number of interrogated peaks. FIG. 4E. (Left) High confidence Yap5SA OE up-regulated genes (RNA-seq adjusted p-value<0.01) mapped to Yap5SA up-regulated ATAC-seq peaks (adjusted p-value<1e-5) and to Yap5SA ChIP-seq peaks (HOMER peak score cutoff of 20). (Right) Highly enriched GO terms from each category. FIG. 4F. ATAC-seq signal across Yap5SA up-regulated genes (T marks TEAD motifs; Y marks Yap ChIP-seq peaks). FIG. 4G. ChIP-seq and ATAC-seq signal in promoters of Yap5SA up-regulated genes. Chip-seq Peaks at promoters indicated by green arrows.

FIG. 5A. Representative ECG traces from control and Yap5SA OE mice before and after tamoxifen. Inverted T-wave indicated. FIG. 5B. (Top) Proportions of mice inverted T wave *P=0.0286 (Fisher's exact test). (Bottom) Relative area under the curve of T wave. Means+/−SEM. Statistics computed by ANOVA with post hoc Bonferroni test. Control n=3, Yap5SA n=4. FIG. 5C. Immunostaining of β-galactosidase (aqua) and Connexin 43(red) showing recombined, β-gal(+) CMs coupling to unrecombined CMs (no stain, black) through gap junctions. Yellow arrows indicate β-gal(−) CMs in syncytium with Yap5SA OE CMs. Inset is a close-up view. FIG. 5D. (Left) Representative plot of sarcomere shortening. (Middle) Resting CM sarcomere length. Shown as means (Right) Percent sarcomere shortening. Shown as means+/−SEM. No statistical difference. control n=5 animals, 27 cells. Yap5SA OE n=5 animals, 31 cells. ANOVA with post hoc Bonferroni test.

FIGS. 6A-6C. Flow cytometry analysis of cell cycle stage FIG. 6A. Representative histograms from flow cytometry of isolated cardiac nuclei from control and Yap5SA OE hearts, stained with DAPI. Pie charts control n=4, Yap5SA OE n=4. Data in pie charts shown as mean, P values computed by ANOVA, followed by Bonferroni post-hoc test. P<0.05 is indicated with an asterisk FIG. 6B. Representative Dot plots from CM DNA content by FACS referred to in A. FIG. 6C. FACS DNA content analysis means and SEM, n=4/genotype. Statistics computed by ANOVA followed by post-hoc Bonferroni tests.

FIG. 10A. Gene ontology analysis on up and down regulated genes in the Yap5SA OE hearts (p<0.01). FIG. 10B. Heat map of selected genes from the RNA-seq FIGS. 11A-11B. Yap5SA induces a futile negative feedback loop.

FIG. 12A. Total Intergenic ATAC-seq peak distance to TSS across both genotypes (Control: 34738 peaks; Yap5SA OE: 40,333 peaks) FIG. 12B. Up-regulated intergenic ATAC-seq and ChIP-seq peaks distance to TSS.

FIGS. 13A.1-13A.3 and 13B-13D. High confidence Yap5SA targets (FIGS. 13A1-13A3) (Left) List of 97 genes directly up-regulated by Yap5SA in regions where the chromatin was already open. (Middle) List of 106 genes with newly open chromatin and up-regulated RNA. (Right) List of 76 genes directly up-regulated by Yap5SA with increased open chromatin.

FIGS. 14A-14C. Model of Yap5SA activation of cardiomyocyte proliferation FIG. 14A. In certain cases, Yap binds directly to open promoters of target genes, increasing transcription. Such a process does not result in new open chromatin reads. FIG. 14B. Primarily, Yap5SA binds to enhancer regions, recruiting in chromatin remodeling factors, such as the SWI/SNF complex to open the genomic neighborhood of target genes. Yap itself or other transcription factors are then free to promote transcription. FIG. 14C. (Left panel) Between those two direct activation schemes, Yap5SA facilitates proliferation through three processes: 1. Activation of the cell cycle through Kruppel like factors, E2F transcription factors, Cyclins, and Polo-like kinases. 2. Rearranging the cytoskeleton and promoting cytokinesis through Formin, Protein kinase C iota, Ect2, Incenp, and Ephexin4.3. Re-emergence of genes associated with fetal heart development, e.g. Protein kinase D1, Alcam, and Disabled homolog 2. (Right panel) independently, those three processes have minimal or detrimental function. For brevity, only direct ChIP-seq targets are included in the left panel, indicated by color. The right panel includes directly up-regulated genes, as well as indirectly (up or down) regulated transcripts indicated by color (genes included according to FIGS. 4A and 4D).

FIG. 15A, WT P19 cells and P19 cells with YapK265R mutation (No. 13) treated with 20 ug/ml cycloheximide for 0, 2, 4 and 6 hours, and harvested with 0.5% NP40 lysis buffer. Immunoblotted for the antibodies as indicated. FIG. 15B, Lysates from P19 cells and two different P19 colonies with YapK265R mutation immunoblot analyzed with the indicated antibodies.

FIG. 17A, WT P19 cells and P19 cells with YapK265R mutation (No. 11) treated with 20 ug/ml cycloheximide for 0, 2, 4 and 8 hours, and harvested with 0.5% NP40 lysis buffer. Immunoblotted for the antibodies as indicated. FIG. 17B, Relative amount of Yap was quantified by densitometry, normalized to GAPDH, and plotted.

FIG. 18A, WT P19 cells and P19 cells with YapK265R mutation (No. 11) treated with 20 uM/ml Mg132 for 0, 1, 2 and 4 hours, and harvested with 0.5% NP40 lysis buffer. Immunoblotted for the antibodies as indicated. FIG. 18B and FIG. 18C, Relative amount of Yap and β-Catenin were quantified by densitometry, normalized to GAPDH, and plotted.

FIGS. 19A-19D. Determination of Yap mutant protein nuclear localization. FIG. 19A and FIG. 19B, $2.0 \times 10^6$ cells were seeded in 10 cm dishes, 18 hours later, cells were harvested and fractionated for western blotting analysis. FIG. 19C and FIG. 19D, Relative amount of Yap was quantified by densitometry, normalized to HDAC2 (for nuclear fraction) or GAPDH (for cystosol fraction), and plotted.

DETAILED DESCRIPTION

Figure 1E:
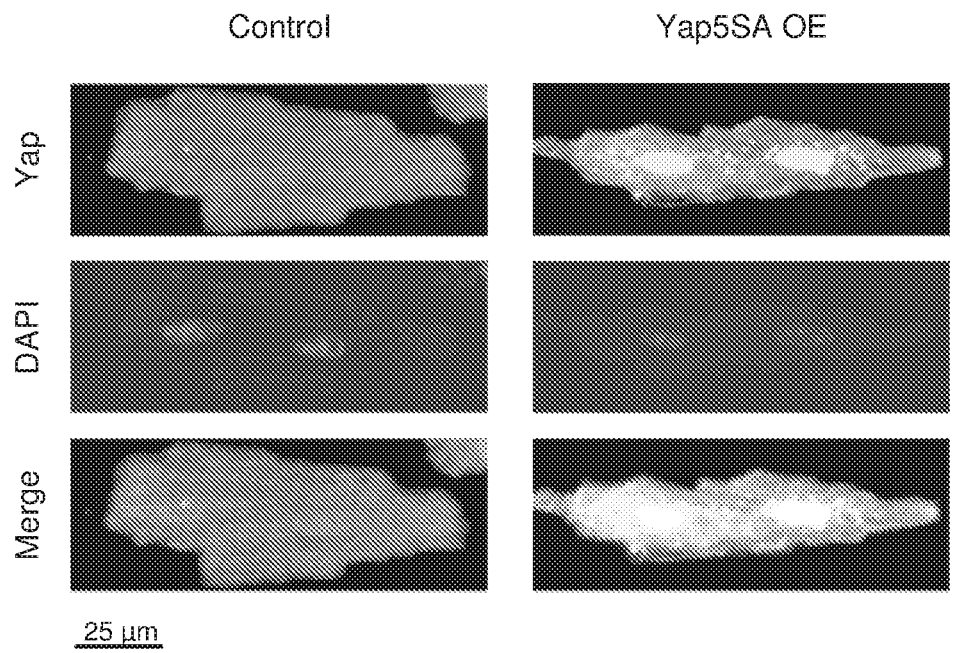
Figure 1E:
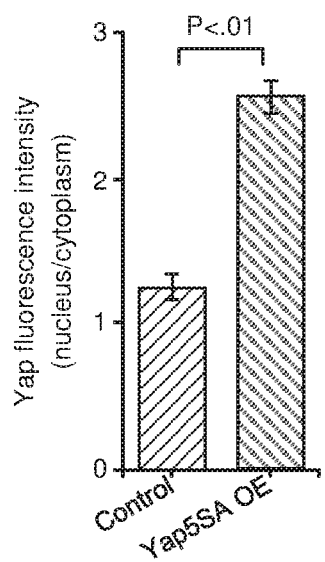

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "therapeutically effective amount" is synonymous with "therapeutically effective dose" or "effective dose" and refers to the amount of Yap mutant protein or polypeptide that will elicit the biological or clinical response being sought by the practitioner in an individual in need thereof. As a non-limiting example, an effective amount is an amount sufficient to regenerate cells or tissue.

I. Examples of Yap Mutants

Embodiments of the disclosure include one or more mutants of Yap and their use for clinical and/or research purposes. The mutant(s) may comprise one or more of the following, for example: amino acid substitution(s); deletion(s); insertion(s); a combination thereof; and so forth. In specific embodiments, one or more amino acids of Yap are substituted with another one or more amino acids. One or more particular mutations may be employed to diminish the biologic activity of the mutant Yap. Such a mutation may or may not be used in conjunction with another mutation in the same mutated Yap protein. Any mutated Yap protein encompassed in the disclosure may be non-natural. Any protein or DNA related to any Yap mutant may be isolated from nature.

A Yap mutant protein may have substitution at one or more serines in the protein. In specific cases, 1, 2, 3, 4, or 5 serines that are the main phosphorylation sites for Lats kinases are substituted. Although any serine can be substituted with any other amino acid, in specific cases they are substituted with alanine.

As used herein, in specific embodiments a mutated variant of human Yap comprises a mutation at least at one of the serines underlined in this wildtype sequence below. These underlined serine residues are either known to be phosphorylated by Lats, or predicted to be. (SEQ ID NO:1):

```
  1  MDPGQQPPPQPAPQGQGQPPSQPPQGQGPPSGPGQPAPAATQAAPQAPPAGHQIVHVRGD
 61  SETDLEALFNAVMNPKTANVPQTVPMRLRKLPDSFFKPPEPKSHSRQASTDAGTAGALTP
121  QHVRAHSSPASLQLGAVSPGTLTPTGVVSGPAATPTAQHLRQSSFEIPDDVPLPAGWEMA
181  KTSSGQRYFLNHIDQTTTWQDPRKAMLSQMNVTAPTSPPVQQNMMNSASGPLPDGWEQAM
241  TQDGEIYYINHKNKTTSWLDPRLDPRFAMNQRISQSAPVKQPPPLAPQSPQGGVMGGSNS
361  NQQQQMRLQQLQMEKERLRLKQQELLRQELALRSQLPTLEQDGGTQNPVSSPGMSQELRT
361  MTTNSSDPFLNSGTYHSRDESTDSGLSMSSYSVPRTPDDFLNSVDEMDTGDTINQSTLPS
421  QQNRFPDYLEAIPGTNVDLGTLEGDGMNIEGEELMPSLQEALSSDILNDMESVLAATKLD
481  KESFLTWL
```

In addition to, or alternative to, one or more mutations at one or more serines in the sequence above, there may be one or more mutations in the sequence that are not at a serine. Such a mutation may be an amino acid substitution (whether conservative or not), deletion, and/or inversion, and so forth. In specific embodiments the mutated version of Yap has five mutations, each at a serine as a single amino acid substitution. In specific cases the one or more serines are mutated to alanine, although the serine(s) may be mutated to a different amino acid, such as histidine, isoleucine, leucine, lysine, methionine, phenylalanine, threonine, tryptophan, valine, arginine, cysteine, glutamine, glycine, proline, tyrosine, alanine, asparagine, aspartic acid, and glutamic acid. In any case, 1, 2, 3, 4, 5, 6, 7, 8, 9, 10, or more serines may be mutated in a single mutant Yap protein.

One example of a mutant Yap protein is as follows (the underlined indicates sites where serines are replaced with alanines and bold indicates the Lats recognition sequence):

(SEQ ID NO: 2)
```
  1  MDPGQQPPPQPAPQGQGQPPSQPPQGQGPPSGPGQPAPAATQAAPQAPPAGHQIVHVRGD
 61  AETDLEALFNAVMNPKTANVPQTVPMRLRKLPDSFFKPPEPKSHSRQAATDAGTAGALTP
121  QHVRAHAAPAALQLGAVSPGTLTPTGVVSGPAATPTAQHLRQAAFEIPDDVPLPAGWEMA
181  KTSSGQRYFLNHIDQTTTWQDPRKAMLSQMNVTAPTSPPVQQNMMNSASGPLPDGWEQAM
241  TQDGEIYYINHKNKTTSWLDPRLDPRFAMNQRISQSAPVKQPPPLAPQSPQGGVMGGSNS
301  NQQQQMRLQQLQMEKERLRLKQQELLRQELALRSQLPTLEQDGGTQNPVSSPGMSQELRT
```

```
361 MTTNSSDPFLNSGTYHSRDEATDSGLSMSSYSVPRTPDDFLNSVDEMDTGDTINQSTLPS

421 QQNRFPDYLEAIPGTNVDLGTLEGDGMNIEGEELMPSLQEALSSDILNDMESVLAATKLD

481 KESFLTWL
```

SEQ ID NO: 2 lacks any version of a tag, such as Flag-tag.

One example of a Yap mutant protein with Flag-tag (SEQ ID NO:3) is as follows:

```
M D Y K D D D D K L A A A N S S L A T M D Y K D D D D K A R L E S V P
K D P G Q Q P P P Q P A P Q G Q G Q P P S Q P P Q G Q G P P S G P G Q P A P A A T Q A
A P Q A P P A G H Q I V H V R G D A E T D L E A L F N A V M N P K T A N V P Q T V P
M R L R K L P D S F F K P P E P K S H S R Q A A T D A G T A G A L T P Q H V R A H A
A P A A L Q L G A V S P G T L T P T G V V S G P A A T P T A Q H L R Q A A F E I P D D
V P L P A G W E M A K T S S G Q R Y F L N H I D Q T T T W Q D P R K A M L S Q M N V
T A P T S P P V Q Q N M M N S A S G P L P D G W E Q A M T Q D G E I Y Y I N H K N K
T T S W L D P R L D P R F A M N Q R I S Q S A P V K Q P P P L A P Q S P Q G G V M G G
S N S N Q Q Q Q M R L Q Q L Q M E K E R L R L K Q Q E L L R Q E L A L R S Q L P T L
E Q D G G T Q N P V S S P G M S Q E L R T M T T N S S D P F L N S G T Y H S R D E A T
D S G L S M S S Y S V P R T P D D F L N S V D E M D T G D T I N Q S T L P S Q Q N R F
P D Y L E A I P G T N V D L G T L E G D G M N I E G E E L M P S L Q E A L S S D I L N
D M E S V L A A T K L D K E S F L T W L
```

One example of DNA that encodes a Yap mutant protein is as follows (SEQ ID NO:4):

```
ATGGACTACAAAGACGATGACGACAAGCTTGCGGCCGCGAATTCAAGCTT
AGCCACCATGGACTACAAAGACGATGACGATAAAGCAAGGCTCGAATCGG
TACCTAAGGATCCCGGGCAGCAGCCGCCGCCTCAACCGGCCCCCCAGGGC
CAAGGGCAGCCGCCTTCGCAGCCCCCGCAGGGGCAGGGCCCGCCGTCCGG
ACCCGGGCAACCGGCACCCGCGGCGACCCAGGCGGCGCCGCAGGCACCCC
CCGCCGGGCATCAGATCGTGCACGTCCGCGGGGACGCGGAGACCGACCTG
GAGGCGCTCTTCAACGCCGTCATGAACCCAAGACGGCCAACGTGCCCCA
GACCGTGCCCATGAGGCTCCGGAAGCTGCCCGACTCCTTCTTCAAGCCGC
CGGAGCCCAAATCCCACTCCCGACAGGCCGCTACTGATGCAGGCACTGCA
GGAGCCCTGACTCCACAGCATGTTCGAGCTCATGCCGCTCCAGCTGCTCT
GCAGTTGGGAGCTGTTTCTCCTGGGACACTGACCCCCACTGGAGTAGTCT
CTGGCCCAGCAGCTACACCCACAGCTCAGCATCTTCGACAGGCTGCTTTT
GAGATACCTGATGATGTACCTCTGCCAGCAGGTTGGGAGATGGCAAAGAC
ATCTTCTGGTCAGAGATACTTCTTAAATCACATCGATCAGACAACAACAT
GGCAGGACCCCAGGAAGGCCATGCTGTCCCAGATGAACGTCACAGCCCCC
ACCAGTCCACCAGTGCAGCAGAATATGATGAACTCGGCTTCAGGTCCTCT
TCCTGATGGATGGGAACAAGCCATGACTCAGGATGGAGAAATTTACTATA
TAAACCATAAGAACAAGACCACCTCTTGGCTAGACCCAAGGCTTGACCCT
CGTTTTGCCATGAACCAGAGAATCAGTCAGAGTGCTCCAGTGAAACAGCC
ACCACCCCTGGCTCCCCAGAGCCCACAGGGAGGCGTCATGGGTGGCAGCA
ACTCCAACCAGCAGCAACAGATGCGACTGCAGCAACTGCAGATGGAGAAG
GAGAGGCTGCGGCTGAAACAGCAAGAACTGCTTCGGCAGGAGTTAGCCCT
GCGTAGCCAGTTACCAACACTGGAGCAGGATGGTGGGACTCAAAATCCAG
TGTCTTCTCCCGGGATGTCTCAGGAATTGAGAACAATGACGACCAATAGC
TCAGATCCTTTCCTTAACAGTGGCACCTATCACTCTCGAGATGAGGCTAC
AGACAGTGGACTAAGCATGAGCAGCTACAGTGTCCCTCGAACCCCAGATG
ACTTCCTGAACAGTGTGGATGAGATGGATACAGGTGATACTATCAACCAA
AGCACCCTGCCCTCACAGCAGAACCGTTTCCCAGACTACCTTGAAGCCAT
TCCTGGGACAAATGTGGACCTTGGAACACTGGAAGGAGATGGAATGAACA
TAGAAGGAGAGGAGCTGATGCCAAGTCTGCAGGAAGCTTTGAGTTCTGAC
ATCCTTAATGACATGGAGTCTGTTTTGGCTGCCACCAAGCTAGATAAAGA
AAGCTTTCTTACATGGTTATAG
```

In some embodiments, a Yap mutant has one or more mutations so that it is less stable compared to lacking those one or more mutations.

In one embodiment, a Yap mutant has a mutation at position 265, such as a lysine at position 265 (human lysine 280). In specific embodiments the lysine at position 265 (human 280) is mutated to another amino acid that may be any other amino acid, but in specific cases the mutation is K265R, which is analogous to lysine 280 in the human sequence.

The present disclosure encompasses proteins and nucleic acids that encode them, including a mutated variant of Yap. In some cases, the mutant Yap protein(s) is delivered in polypeptide form, and in some cases the mutant Yap protein(s) is delivered as a polynucleotide that encodes the protein. When delivered in polynucleotide form, the polynucleotide may comprise an expression construct in a suitable vector. The vector may be of any suitable kind, such as non-viral or viral. In cases wherein the vector is non-viral, the vector may be a plasmid or linear sequence of RNA. In cases wherein the vector is viral, the vector may be adenoviral, lentiviral, adeno-associated, retroviral, and so forth. When regulated by a promoter in an expression construct, the promoter may be constitutive, inducible, or tissue-specific, for example. In particular, embodiments, the mutant variant of Yap will be delivered in an adeno associated virus construct or as a modified RNA[9].

II. Examples of Methods of Use

Embodiments of the disclosure include methods of tissue renewal in a tissue of interest, including at least in the heart, retina, and hair cells of the ear. In particular embodiments, an individual with a need for cell regeneration or tissue renewal is provided an effective amount of one or more mutated variants of Yap.

Adult mammalian cardiomyocyte (CM) renewal is inefficient. Injured CMs fail to proliferate, and instead activate endoreduplication that increases ploidy. As a result, the heart is prone to failure, the leading cause of human death. In particular embodiments, the inventors expressed a version of the Hippo effector Yap, called Yap5SA, in adult CMs that is impervious to Hippo inhibition. Yap5SA induced CM proliferation with a 33 hour doubling time, hyperplastic ventricular walls, and greater than 15% of CMs reinitiated mitosis. Genome-wide characterization of chromatin accessibility revealed that Yap5SA promoted the opening of distal enhancers and expression of a robust mitotic gene program. The genes and enhancers revealed herein, promoting CM proliferation, are useful for stimulating cardiac regeneration. Thus, embodiments of the disclosure include methods and compositions for the renewal of cardiomyocytes, including by targeting the Hippo pathway. In particular embodiments, an individual with a need for cardiomyocyte renewal is provided an effective amount of one or more mutated variants of Yap. In certain embodiments, there is a method of regenerating cells at a desired location in an individual, comprising the steps of delivering to the location an effective amount of Yap mutant protein(s) and/or polynucleotide(s) encoding Yap mutant protein.

In particular embodiments there are methods of treating a medical condition by delivering a therapeutically effective amount of one or more mutated variants of Yap to the individual. At least one symptom of any medical condition may be improved upon administration of one or more mutant Yap protein(s) and/or nucleic acid(s) encoding them.

Certain embodiments of the disclosure include methods of regenerating cardiomyocytes in an individual by providing to the individual a therapeutically effective amount of one or more mutated variants of Yap. In at least some cases, the mutated variant comprises 1, 2, 3, 4, 5, 6, 7, 8, 9, 10, or more amino acid substitutions at a serine, and the substitutions may or may not be to an alanine. Other non-serine mutations may be included in the mutated Yap. Certain methods may be performed on one or more individuals that are in need of regeneration of cardiomyocytes, such as individuals with damage to the heart or at risk for damage to the heart. The individual may have damaged heart muscle tissue in need of regeneration of cardiomyocytes. In particular embodiments, the administration of one or more mutated Yap proteins and/or nucleic acid(s) encoding them results in regeneration of cardiomyocytes from existing cardiomyocytes in the individual.

Embodiments of the disclosure include methods and/or compositions for regeneration of cardiac muscle and reversal of myocardial ischemic injury, for example. In particular embodiments, there are methods for stimulating proliferation of resident adult cardiac progenitor or cardiac muscle cells in mammalian hearts that have had a cardiac condition, such as acute ischemic injury, for example. In certain embodiments, such methods are achieved with compositions comprising one or more mutated variants of Yap to the individual.

Embodiments of the present disclosure are directed to methods and/or compositions related to therapy and/or prevention of one or more cardiac conditions. Embodiments of the present disclosure concern regeneration of tissue, including muscle tissue, such as myocardial tissue. Certain embodiments relate to reversal of a cardiac condition (or improvement of at least one symptom thereof), including at least heart disease, cardiomyopathy, heart valve problems, pericarditis, arrhythmia, cardiac arrest, congenital heart defect, heart failure, cardiac disease, cardiotoxicity, congestive heart failure, ischemic heart disease, acute myocardial infarction, atrial fibrillation, coronary artery disease, ischemic heart disease, valvular heart disease, hypertensive heart disease, and arrhythmias. Particular types of cardiovascular disease may be treated or prevented, such as coronary artery disease (also known as coronary heart disease and ischaemic heart disease); cardiomyopathy (diseases of cardiac muscle); heart failure; cor pulmonale; cardiac dysrhythmias; inflammatory heart disease; endocarditis; inflammatory cardiomegaly; myocarditis; valvular heart disease; cerebrovascular disease; peripheral arterial disease; congenital heart disease; and rheumatic heart disease. Particular but exemplary indications of embodiments of the disclosure include at least applications for 1) congestive heart failure; 2) prevention from ventricular remodeling or aneurysm of myocardial infarction; and/or 3) cardiomyopathy. In specific embodiments, methods and compositions of the disclosure provide cardiomyocyte regeneration that is sufficient to reverse established cardiac condition or prevention of a cardiac condition or delay of onset or reduction in severity.

In cases of cardiomyopathy, the condition may be induced by a drug, such as a chemotherapy drug (like Adriamycin) or a monoclonal antibody[10,11]. The cardiomyopathy may be ischemic or non-ischemic cardiomyopathy. The cardiomyopathy may be caused by long-term high blood pressure, heart valve problems, heart tissue damage from a previous heart attack, chronic rapid heart rate, metabolic disorders, nutritional deficiencies, pregnancy, alcohol abuse, drug abuse, chemotherapy drugs, viral infection, hemochromatosis, genetic condition, elevated cholesterol levels, pulmonary hypertension, or a combination thereof.

Particular aspects of the disclosure concern delivery of a Yap mutant polynucleotide, protein, peptide, or mixture thereof to a certain tissue for proliferation, inhibition of cell death (apoptosis), and/or differentiation of certain cells in the tissue. The tissue may be of any kind, but in specific cases it is muscle tissue, including cardiac tissue, retinal tissue, or hair cells of the ear. In particular embodiments, methods and compositions of the disclosure allow for regeneration of pre-existing adult cardiac muscle cells. In some cases, delivery of the inventive composition(s) results in the cells being more resistant to pathological remodeling and they resist further damage after an initial insult.

Embodiments of the disclosure include delivery of one or more Yap mutant polynucleotides and/or polypeptides that stimulate regeneration of cells (such as muscle cells, including cardiomyocytes) and/or tissue (including cardiac tissue). Particular aspects for such embodiments result in reversal of one or more cardiac-related medical conditions. Certain aspects for such embodiments result in improvement of at least one symptom of a medical condition, such as a cardiac-related medical condition, an ocular medical condition or an otological medical condition.

In specific embodiments, a Yap mutant polynucleotide, protein, peptide, or mixture thereof is targeted to a particular tissue of interest, including a muscle tissue, such as cardiac tissue, for example.

In some cases, methods and compositions of the present disclosure are employed for prevention of one or more cardiac-related medical conditions or delay of onset of one or more cardiac-related medical conditions or reduction of extent of one or more symptoms of one or more cardiac-related medical conditions. In particular cases, such prevention, delay or onset, or reduction of extent of one or more symptoms, occurs in an individual that is at risk for a cardiac-related medical condition. Exemplary risk factors include one or more of the following: age, gender (male, although it occurs in females), high blood pressure, high serum cholesterol levels, tobacco smoking, excessive alcohol consumption, sugar consumption, family history, obesity, lack of physical activity, psychosocial factors, diabetes mellitus, overweight, genetic predisposition, and/or exposure to air pollution.

Any individual being treated may be an adult, adolescent, child, infant, or the treatment may be in utero.

Delivery to the individual of the mutant Yap protein(s) and/or nucleic acid(s) encoding them may be systemic or may be local. In specific examples, following use of the Yap mutant protein or polynucleotide, in vitro-derived cardiomyocytes are delivered to an individual. In other cases, the Yap mutant protein or polynucleotide is delivered in vivo within the heart. This could work, for example, either by using Yap to expand patient-derived (or non-patient-derived) induced-pluripotent stem cell-derived cardiomyocytes (or embryonic stem cell-derived cardiomyocytes) in culture before transplanting into a patient; or by using Yap to expand stem cell-derived cardiomyocytes after transplanting into the patient using small-molecule driven promoters, or other Yap induction schemes engineered into the stem-cell derived cardiomyocytes.

An individual receiving the therapy encompassed herein may or may not have been diagnosed with a medical condition, including a cardiac medical condition, for example. The individual may or may not be exhibiting one or more symptoms of having a cardiac medical condition without having a previous diagnosis, for example.

III. Pharmaceutical Preparations

Pharmaceutical compositions of the present invention comprise an effective amount of one or more Yap mutant proteins and/or polynucleotides encoding same or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one Yap mutant proteins and/or polynucleotides encoding same or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The Yap mutant proteins and/or polynucleotides encoding same may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The Yap mutant proteins and/or polynucleotides encoding same may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present disclosure, the composition is combined with the carrier in any convenient and practical manner, i.e., by solution, suspension, emulsification, admixture, encapsulation, absorption and the like. Such procedures are routine for those skilled in the art.

In a specific embodiment of the present disclosure, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include Yap mutant proteins and/or polynucleotides encoding same, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the Yap mutant proteins and/or polynucleotides encoding same may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the Yap mutant proteins and/or polynucleotides encoding same are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like[12,13] (U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, Yap mutant proteins and/or polynucleotides encoding same may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound Yap mutant proteins and/or polynucleotides encoding same may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins[14] and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

IV. Kits of the Disclosure

Any of the compositions described herein may be comprised in a kit. In a non-limiting example, a mutant Yap polypeptide and/or polynucleotide (or oligonucleotides for generation of it) may be comprised in a kit.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the one or more compositions in close confinement for commercial sale. Such containers may include injection or blow-molded plastic containers into which the desired vials are retained.

The composition may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

The kits of the present disclosure will also typically include a means for containing the vials in close confinement for commercial sale, such as, e.g., injection and/or blow-molded plastic containers into which the desired vials are retained.

In particular embodiments, the kit comprises reagents and/or tools for determining that an individual has a cardiac-related medical condition. In some embodiments, the kit comprises one or more additional therapies for a cardiac-related medical condition, such as one or more of ACE Inhibitor, aldosterone inhibitor, angiotensin II receptor blocker (ARBs); beta-blocker, calcium channel blocker, cholesterol-lowering drug, digoxin, diuretics, inotropic therapy, potassium, magnesium, vasodilator, anticoagulant medication, aspirin, and a combination thereof.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Dominant Active Yap Induces Chromatin Accessibility and Cardiomyocyte Renewal

To characterize that the YapS127A mutation fails to account for all the Lats-dependant Yap inhibition and to model a heart that has no Hippo activity, a transgenic mouse line was generated that conditionally overexpressed Yap5SA that has all five Lats1/2 phosphorylation sites mutated to $A^8$.

The CAG-driven inducible Yap5SA transgene contained a LoxP-flanked-STOP eGFP, followed by Flag tagged Yap5SA and IRES LacZ (FIG. 1A). The transgene directed eGFP expression in embryonic and postnatal hearts before recombination (FIGS. 1B, 1C). The inventors crossed Yap5SA mice to the tamoxifen-inducible, cardiomyocyte-specific Cre driver, αMyHC-Cre-ERT2 (FIG. 1D)[15] to generate Yap5SA overexpressing (OE) mice. Recombination was induced in adult CMs by 4 days of consecutive tamoxifen injections (40 µg/g). Western blots on adult heart extracts showed a 5 fold increase in Yap levels in the Yap5SA OE hearts (FIG. 1D). Immunofluorescence studies revealed a 2.5 fold Yap nuclear enrichment relative to cytosol of Yap5SA OE CMs. Control CMs expressed Yap in both the cytosol and nucleus (FIG. 1E).

Figure 2A:
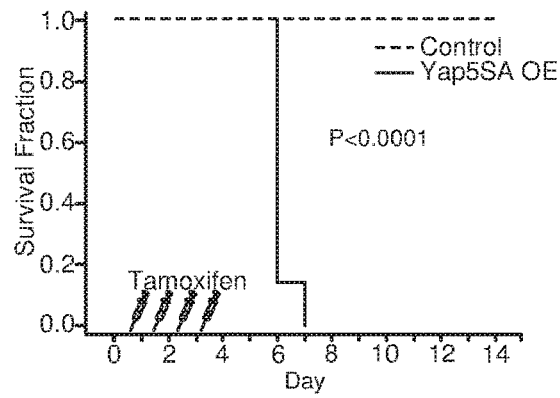
FIGS. 2A-2J. Concentric heart failure and death in Yap5SA OE mice.
Figure 2B:
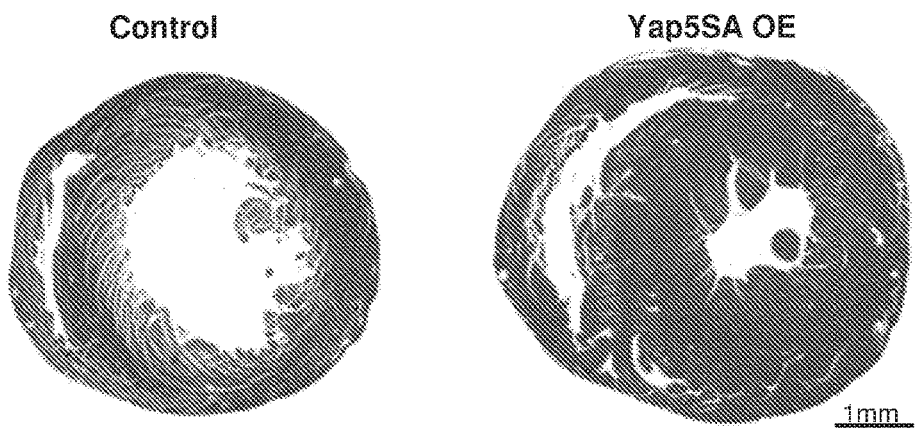
Figure 2C:
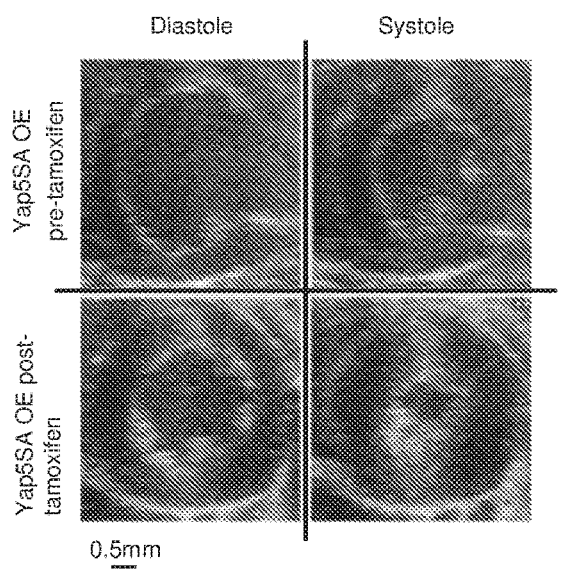
Figure 2D:
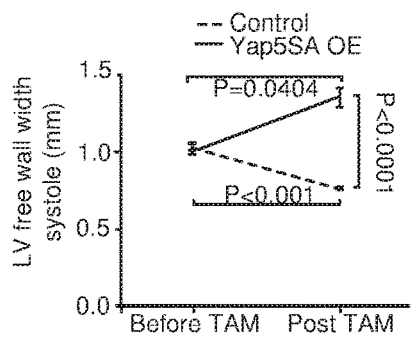
Figure 2E:
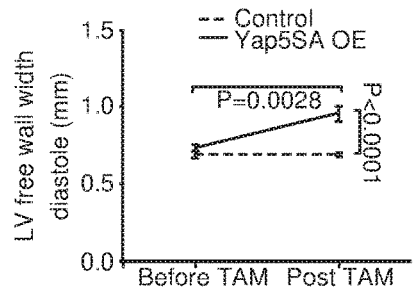
Figure 2F:
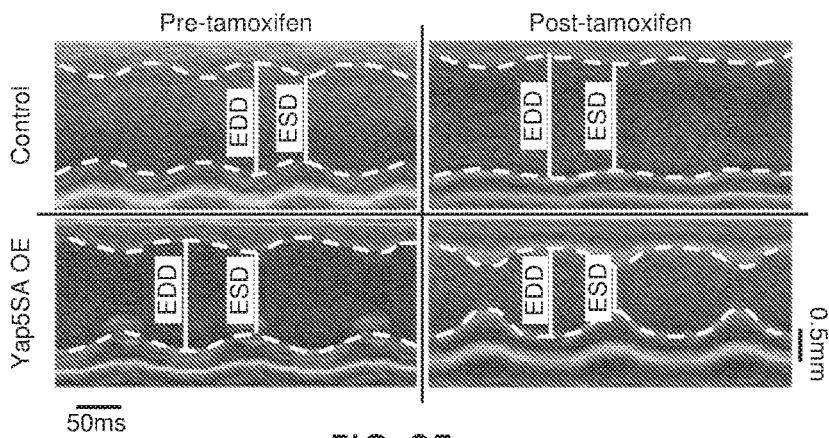
Figure 2G:
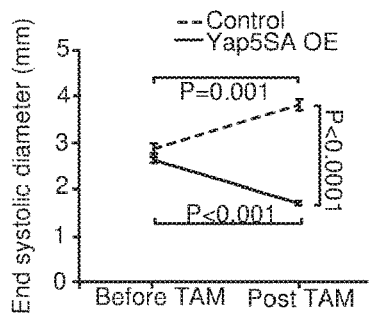
Figure 2H:
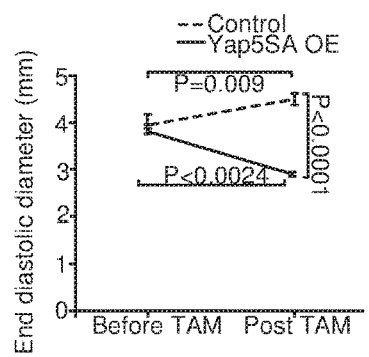
Figure 2I:
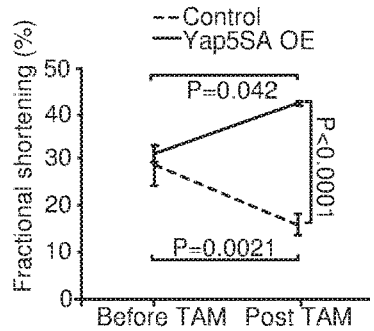
Figure 2J:
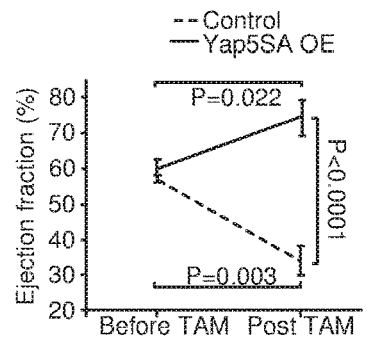

Yap5SA OE mice died 72 hours after the final tamoxifen injection (FIG. 2A). Histology revealed increased left ventricular wall thickness with the LV chambers nearly occluded with muscle (FIG. 2B). Echocardiography from before and one day after tamoxifen showed the thickened ventricular walls, decreased chamber size, and increased ejection fraction of Yap5SA OE hearts in vivo (FIGS. 2C-2J and multiple videos). This phenotype contrasts with cardiotoxic ventricular dilation in control αMHC-merCremer mice after tamoxifen[16].

Figure 3A:
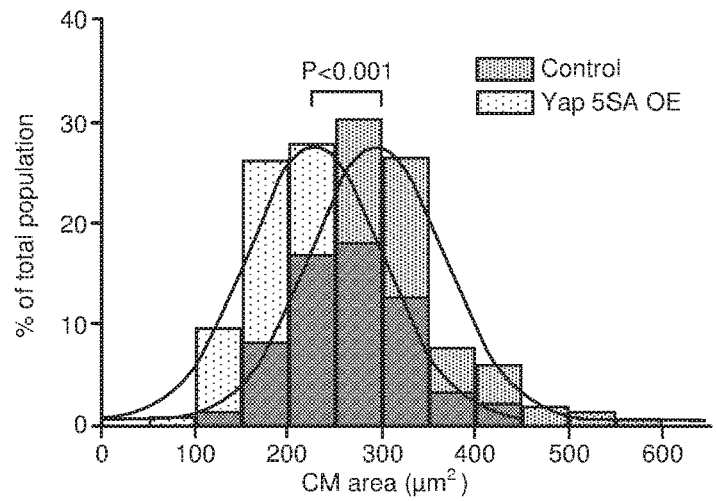
FIGS. 3A-3K. Proliferation of differentiated cardiomyocytes.
Figure 5A:
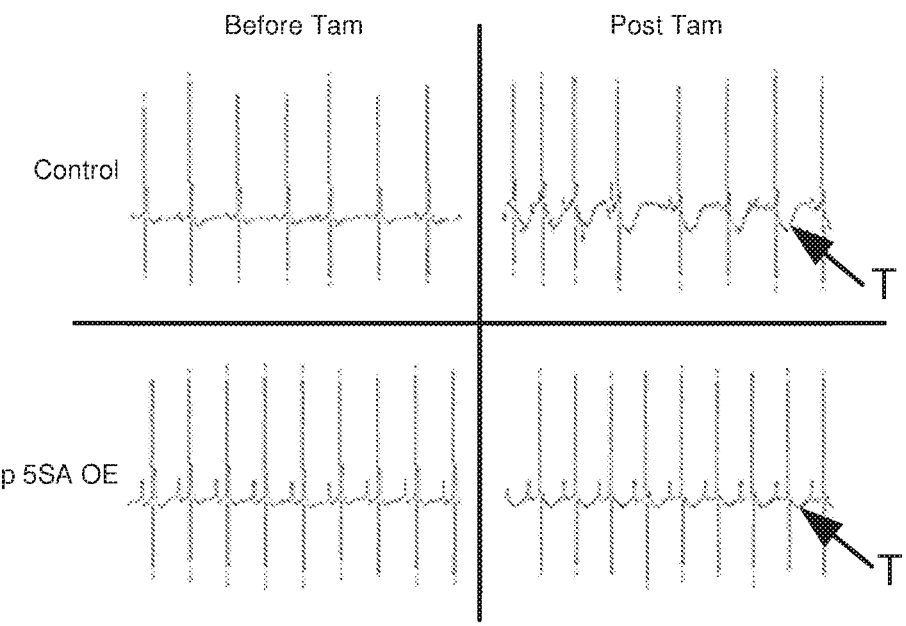
FIGS. 5A-5D. Yap5SA OE myocytes have normal physiology and couple to CMs that do not express the transgene.
Figure 5B:
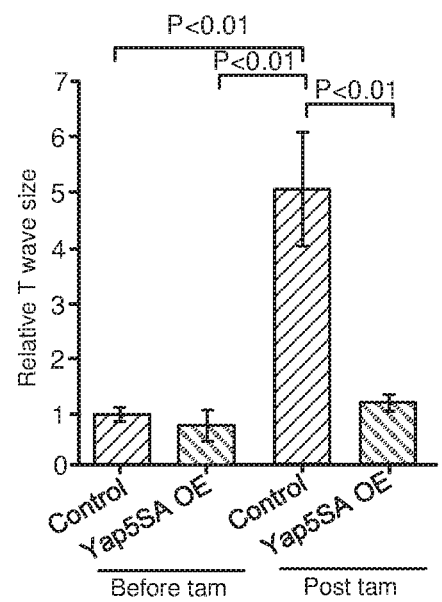
Figure 5C:
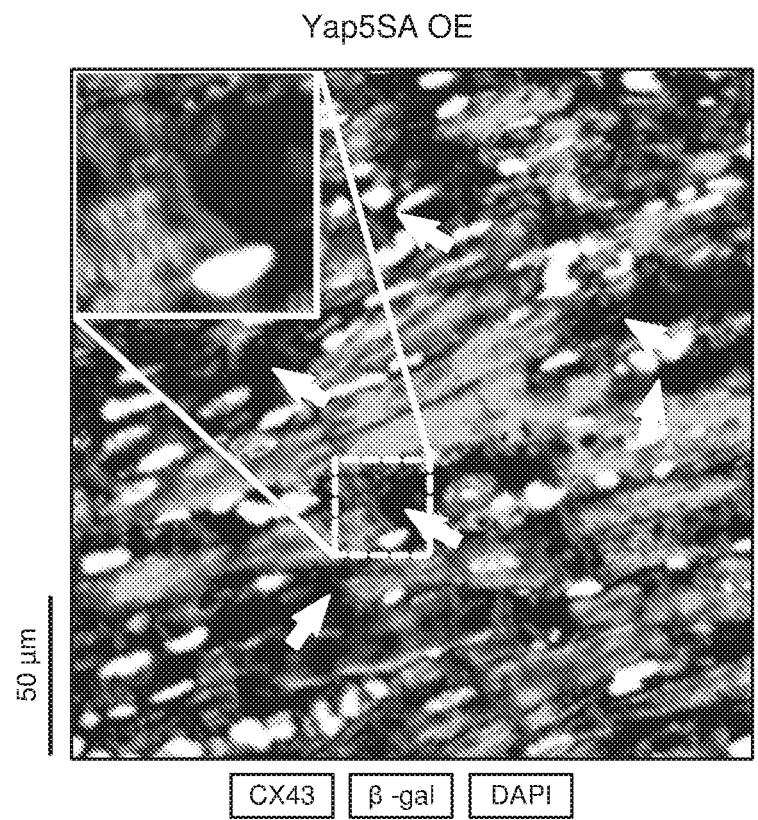
Figure 5D:
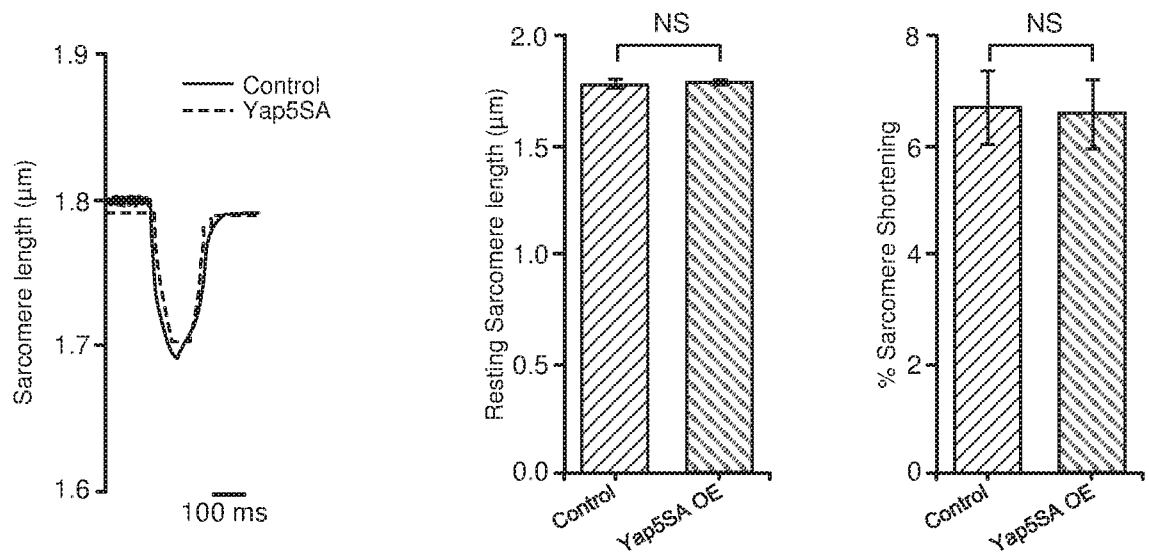

To monitor for arrhythmias, telemetry devices were implanted into littermate control and Yap5SAOE mice. There was no detection of arrhythmias in Yap5SA OE mice but rather protection from tamoxifen-induced arrhythmias (T wave inversion) observed in all the αMyHC-Cre-ERT2 mice studied (FIG. 5A, 5B; n=3). Further, Yap5SA expressing ((3-galactosidase positive) cardiomyocytes were connected to control CMs by gap junctions, as indicated by Connexin43 immunofluorescence (FIG. 5C) suggesting that Yap5SA expressing CMs electrically couple with wild type CMs. Cardiomyocytes were isolated 24 hours after the final tamoxifen injection and studied CM contractility at the individual cell level. Yap5SA OE CMs were smaller but had similar resting sarcomere length and contractility in response to field stimulation as compared to tamoxifen-administered control CMs (FIG. 3A, 5D).

Figure 3B:
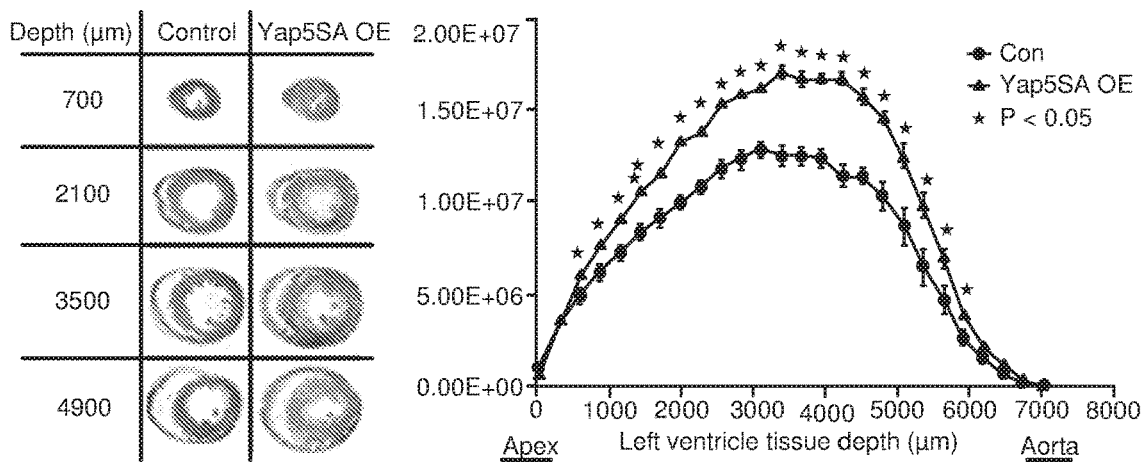
Figure 3C:
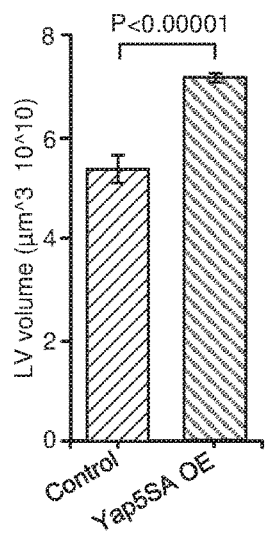
Figure 3D:
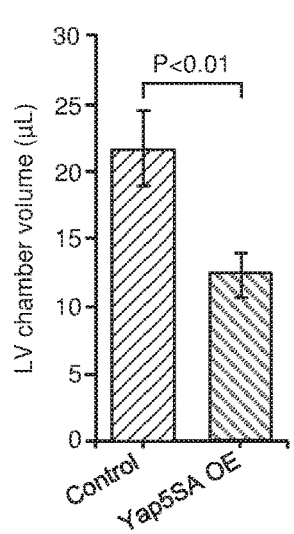
Figure 3E:
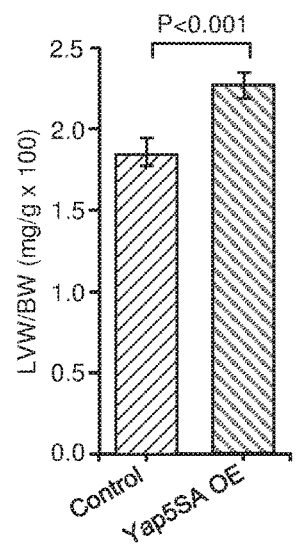

To determine CM number by stereology, diastole fixed hearts were sectioned 2 days post-tamoxifen injection from apex to aorta in 7 µm increments and the inventors directly measured left ventricular area at different tissue depths. The reference left ventricular volume was calculated by plotting left ventricular areas as a function of location within the heart and integrating the area under the curve. Because it can be difficult to unequivocally identify CMs, the inventors used the pericentriolar material 1 (PCM-1) marker to identify CM nuclei in the left ventricle[1]. Yap5SA OE hearts had increased left ventricular wall area, increased myocardial volume, and decreased chamber volume as compared to control hearts (FIG. 3B-3D). Yap5SA OE hearts also increased left ventricle weight to body weight ratio (FIG. 3E).

Figure 3F:
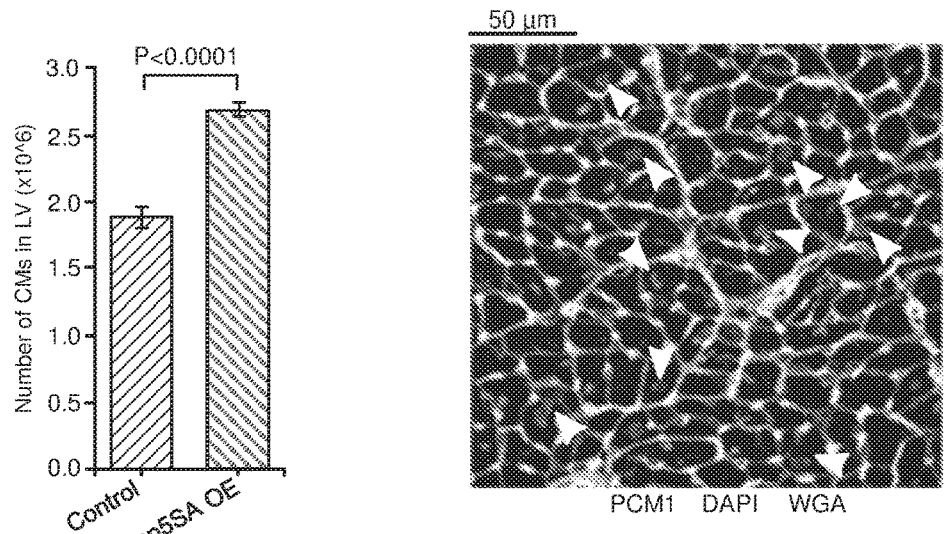

To estimate total left ventricular CM number, the inventors calculated PCM-1 positive CM nuclei density in control (72,100+/−2300 CM nuclei/mm^3) and Yap5SA OE hearts (70,600+/−1300 CM nuclei/mm^3)[1,17]. CM nuclei densities were consistent with recent mouse stereology data from Alkass et. al. (see FIG. 1B). To obtain CM number, the inventors multiplied CM density by total heart volume and corrected for CM nucleation (see below)[117]. Yap5SA OE left ventricles had a large increase in CM number compared to control (Control: 1,880,000+/−78,000 vs. Yap5SA: 2,680,000+/−54,000; ANOVA with Bonferoni post-hoc analysis p<0.0001; FIG. 3F). The control CM number data are also consistent with previously published mouse data[18].

Figure 3G:
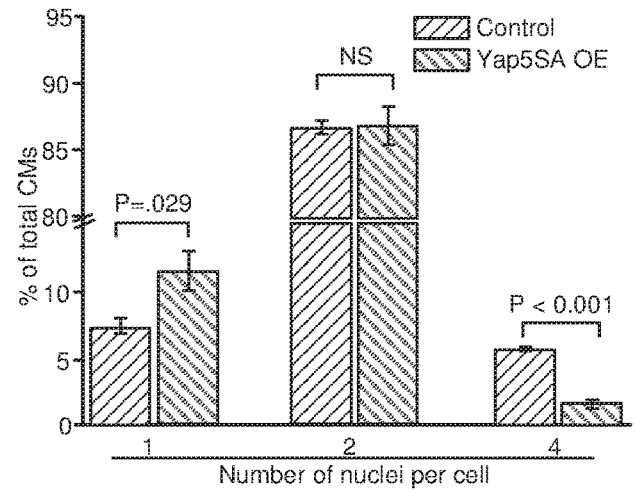

DNA content was quantified of isolated PCM-1 positive CM nuclei by flow cytometry and Yap5SA OE CMs had a small increase in 4N nuclei but no increase in nuclei with greater than 4N DNA content as is seen in models of mitotic catastrophe[19] (FIG. 6). Because diploid cells in G2/M have the same 4N DNA content as tetraploid cells, the data suggest that the increase in Yap5SA 4N nuclei is due to normal cell cycle progression rather than hyper-ploidization[20]. The number of CM nuclei were measured on isolated CMs and there was an increase in mononuclear CMs in Yap5SA OE hearts but no change in bi-nucleated CMs (FIG. 3G). It was also noted that Yap5SA hearts had a reduced proportion of CMs with 4 nuclei suggesting fewer non-productive nuclear divisions (FIG. 3G).

Figure 3H:
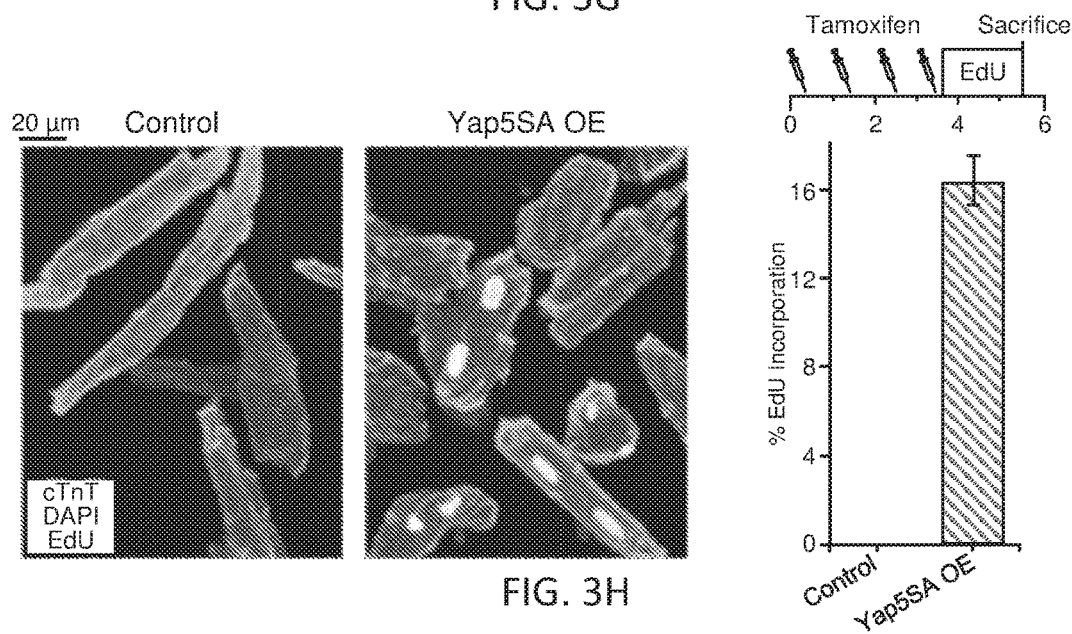
Figure 3I:
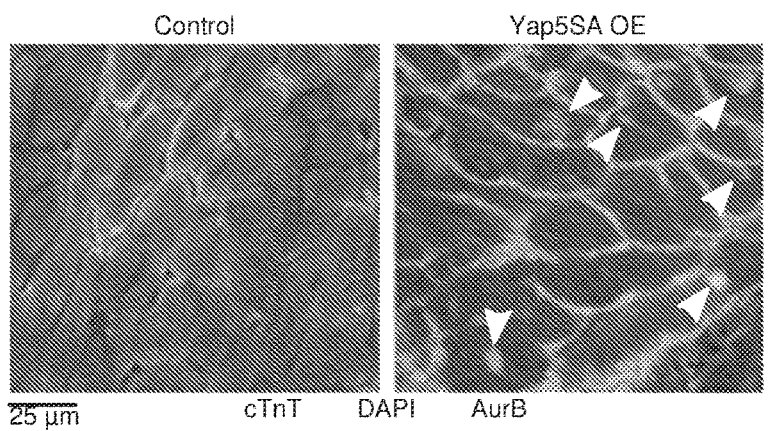
Figure 3I:
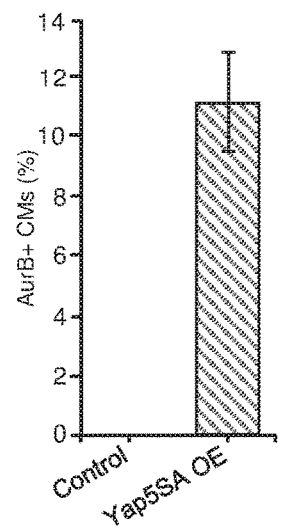
Figure 3J:
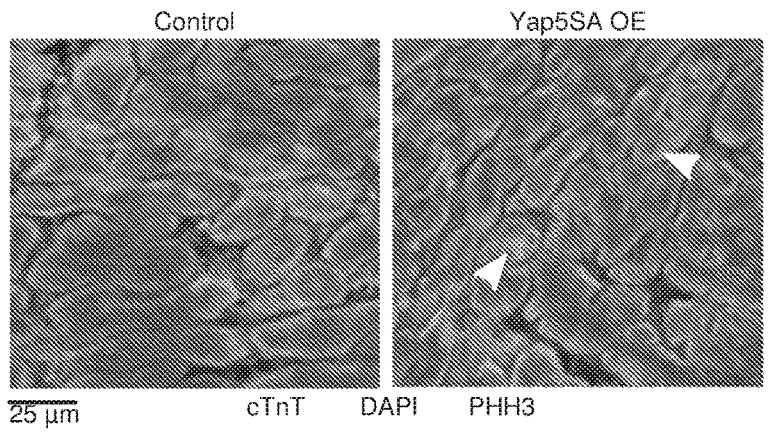
Figure 3J:
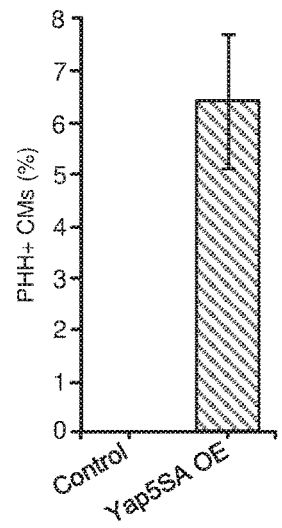
Figure 3K:
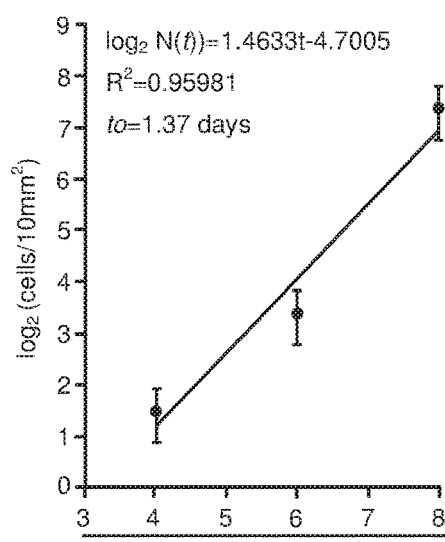
Figure 3K:
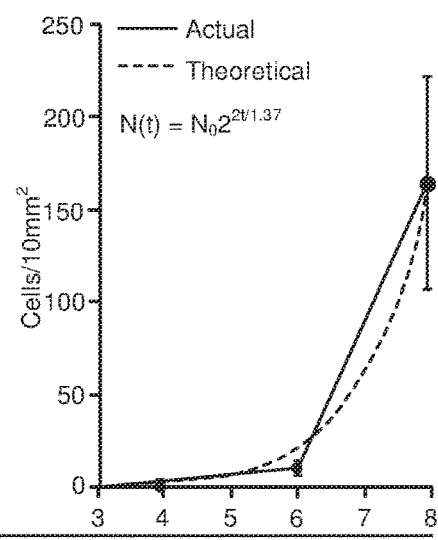
Figure 7:
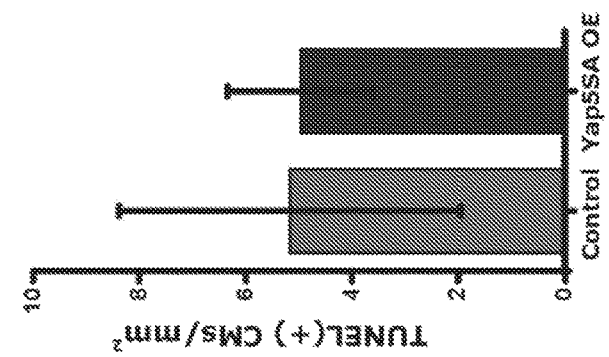
FIG. 7. No evidence of increased cell apoptosis in Yap5SA OE CMs. TUNEL staining shows no significant difference between control and Yap5SA OE hearts (n=4 hearts/genotype). Shown as means+/−SEM statistics computed by pairwise ANOVA, followed by Bonferroni post-hoc test.
Figure 7:
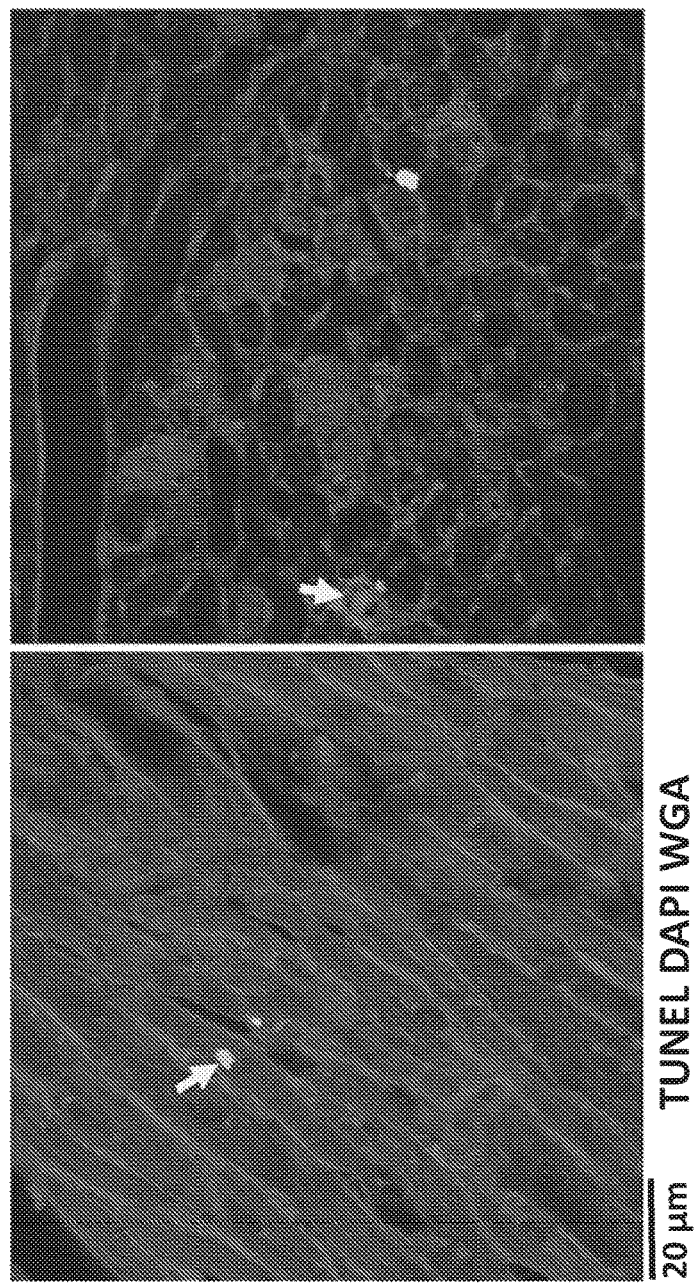
Figure 8:
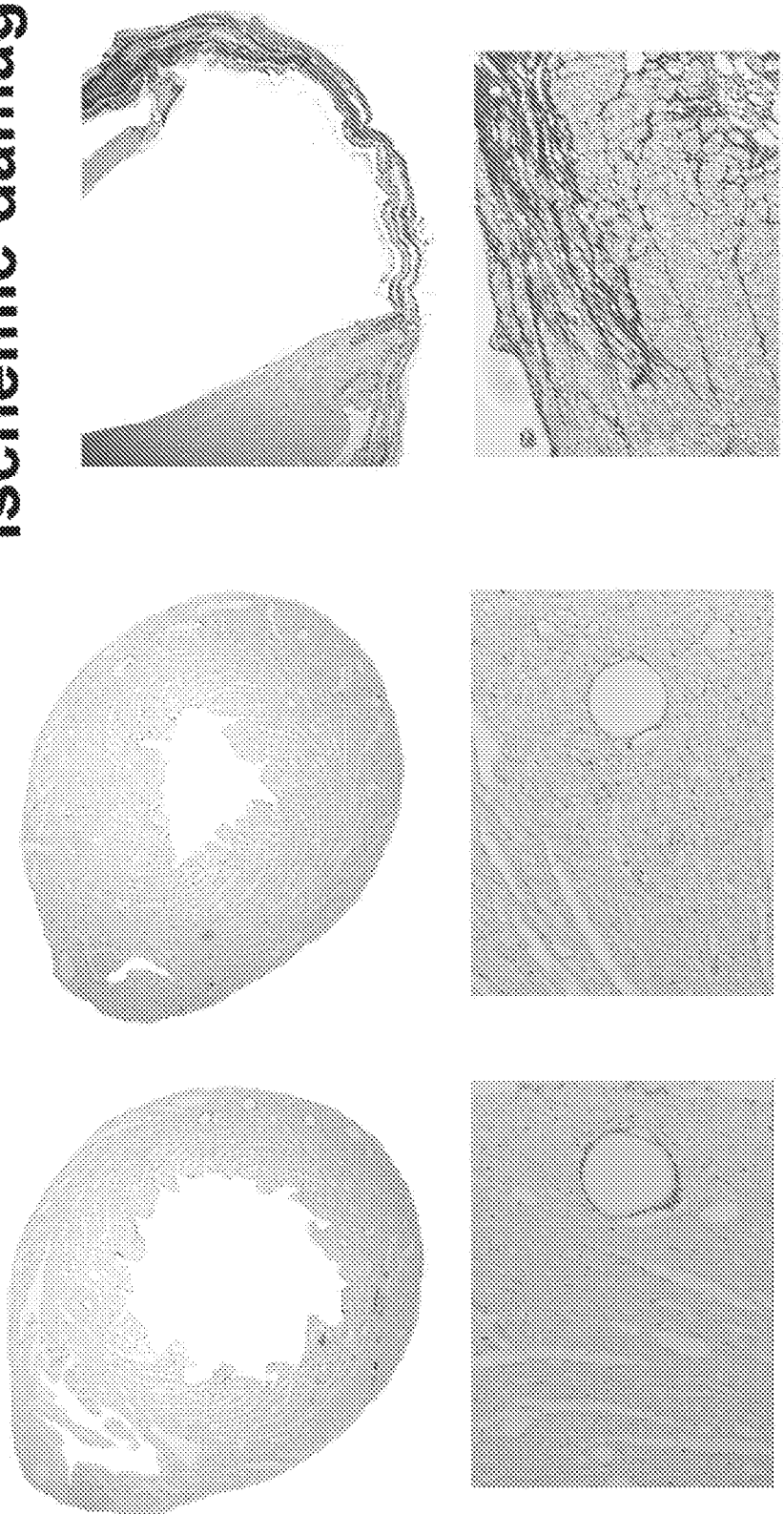
FIG. 8. There is no evidence of fibrosis in Yap 5SA OE hearts. Picrosirius Red stain shows that neither Yap5SA OE hearts nor control have a fibrosis phenotype. A representative heart with fibrotic damage is also shown for comparison FIG. 9. Sequencing Quality Control. (Top) High reproducibility in both sets of ATAC-seq. (Bottom) High reproducibility between the RNA-seq sets. Reads from each indicated experiment were transformed with a regularized-logarithm transformation and displayed as scatter plots to show the relationship of replicate data sets. Note: the data sets are sample matched (e.g. Control-1 ATAC-seq and Control-1 nuclear RNA came from the same biological sample).

The inventors provided EdU ad-libitum in drinking water for two days after Yap5SA induction and stained for EdU on isolated CMs to study S-phase entry in uninjured adult CMs (FIG. 3H). Similarly to previous observations, EdU incorporation in uninjured control CMs was undetectable (FIG. 3H)[2]. In contrast, approximately 16% of Yap5SA OE CMs were EdU positive (FIG. 3H). Moreover, Yap5SA CMs expressed mitotic markers with approximately 11% of Yap5SA CMs Aurkb positive and 6% PHH3 positive (FIGS. 3I-3J). To calculate CM doubling time ($t_D$), infrequent recombination was induced with a single low dose of tamoxifen and LacZ positive CMs were counted at different timepoints. After converting to logarithmic form, the inventors found a $t_D$ of 1.37 days for Yap5SA OE CMs (FIG. 3K). Importantly, Yap5SA did not induce CM apoptosis or interstitial fibrosis (FIGS. 7, 8). Together, the data indicate that Yap5SA induces adult CM proliferation with the birth of new CMs.

Figure 4A:
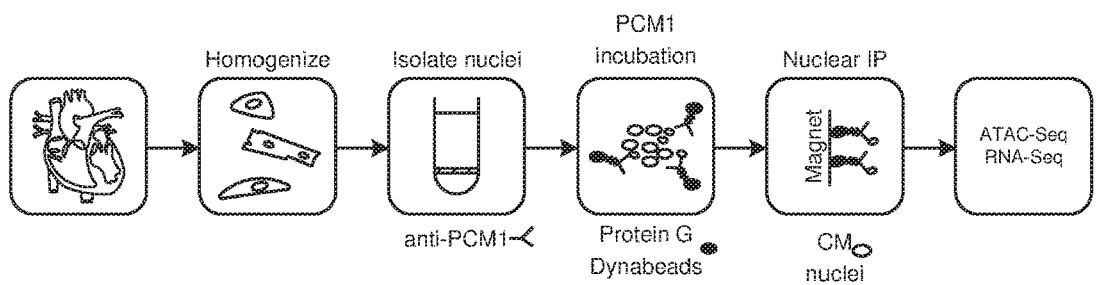
FIGS. 4A-4G. Epigenetic activation of the CM proliferation gene program.
Figure 4A:
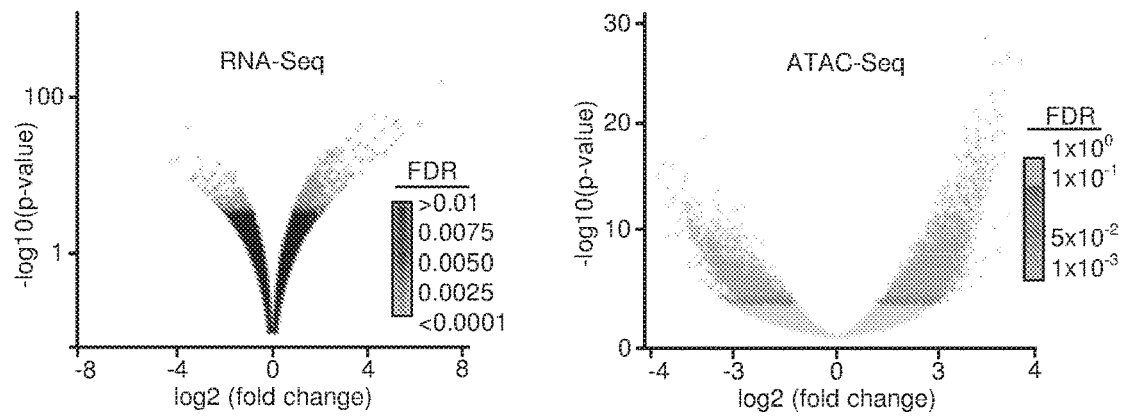
Figure 9:
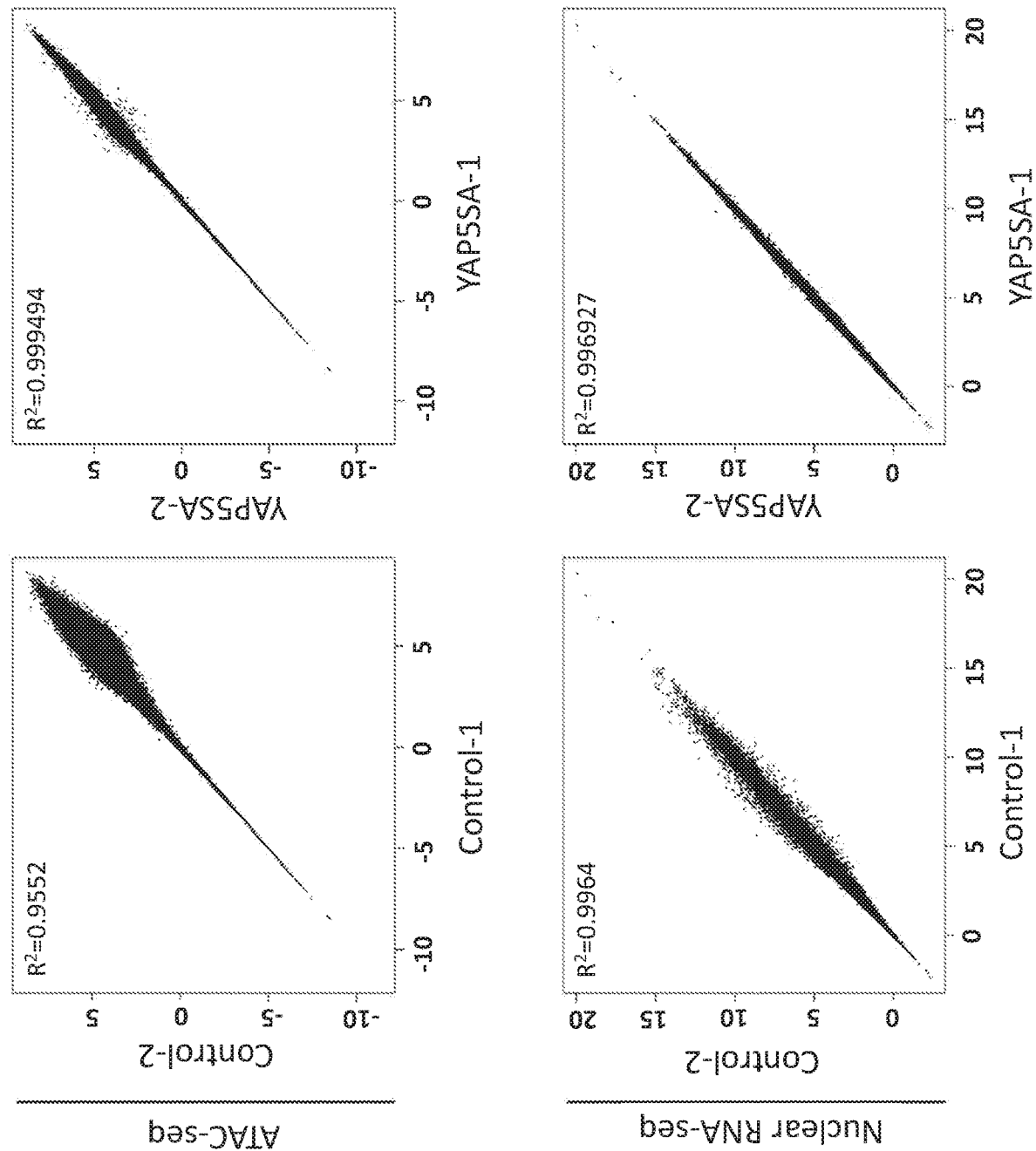
Figure 10A:
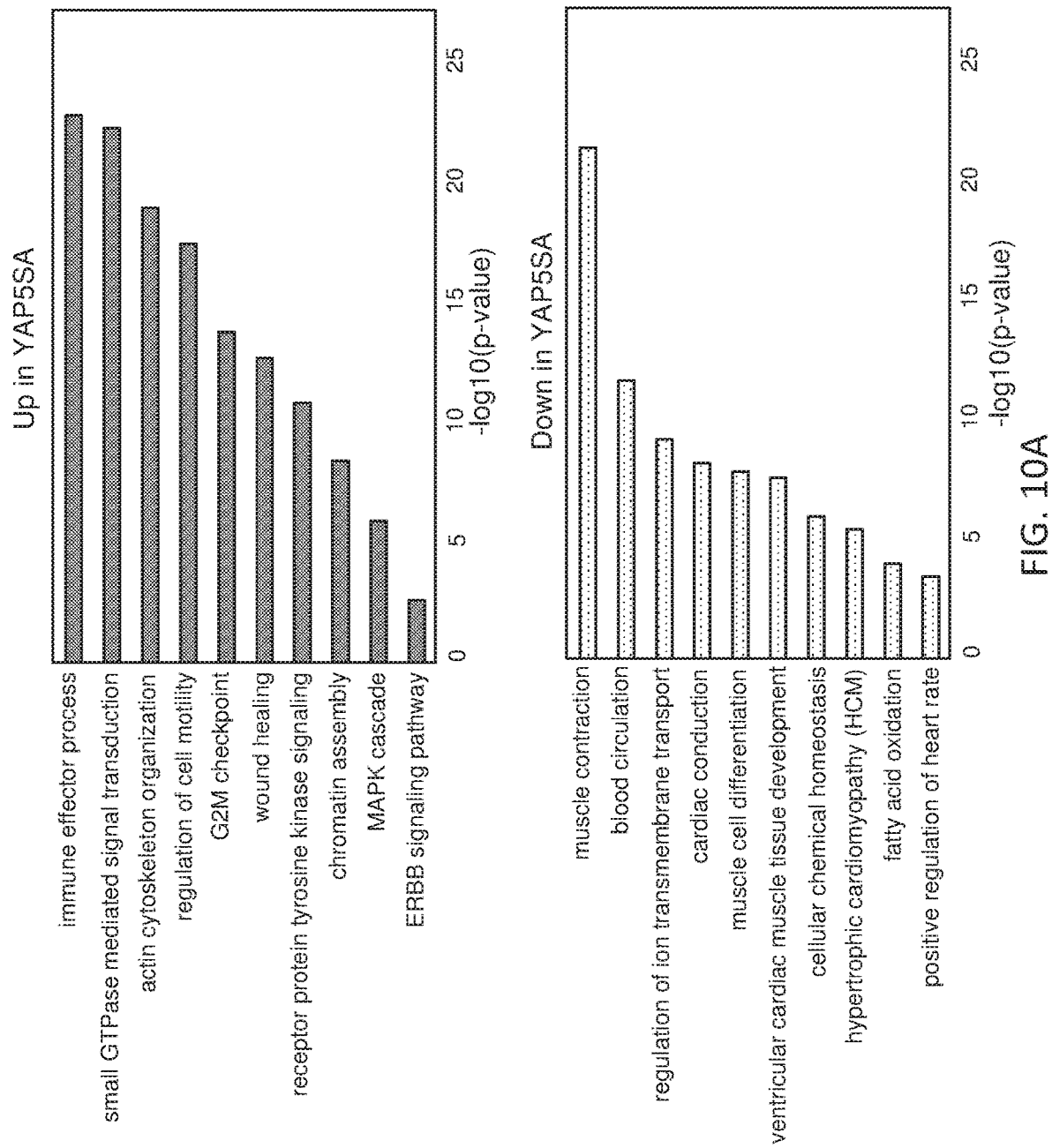
FIGS. 10A-10B.
Figure 10B:
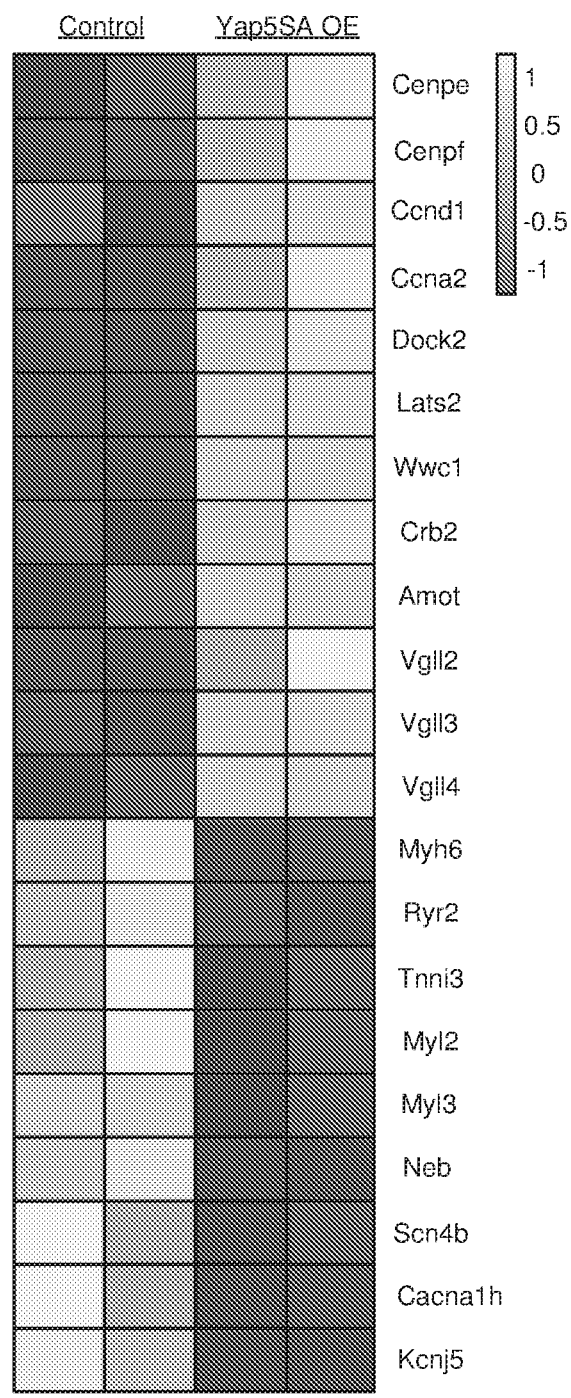

To gain insight into the Yap5SA target genes in the context of adult CM renewal, CM-specific nuclear RNA-seq was performed 48 hours post tamoxifen injection[21,22]. A total of 1,352 genes were significantly up-regulated and 748 were down-regulated in Yap5SA CMs (adjusted p-value<0.01) (FIGS. 4A, 9). Unbiased gene ontology analysis revealed that gene expression changes were consistent with a proliferative CM phenotype (FIG. 10A). Upregulated transcripts included the centromere genes, Cenpe and Cenpf, and the cyclins Ccnd1 and Ccna2. Other genes included Dock2, a Rho family guanine nucleotide exchange factor, that promotes cytoskeletal remodeling and cell proliferation[23]. Downregulated genes included genes encoding myosins and ion channels that characterize the differentiated CM phenotype (FIG. 10B). Interestingly, Hippo pathway genes were among the most significantly increased transcripts in Yap5SA CMs (FIG. 11). The core Hippo pathway genes Lats 2 and Kibra (Wwc1) were upregulated as were genes encoding Yap inhibitors Crb2, Amot, and Vgll2-4 (FIGS. 10B, 11).

Figure 4B:
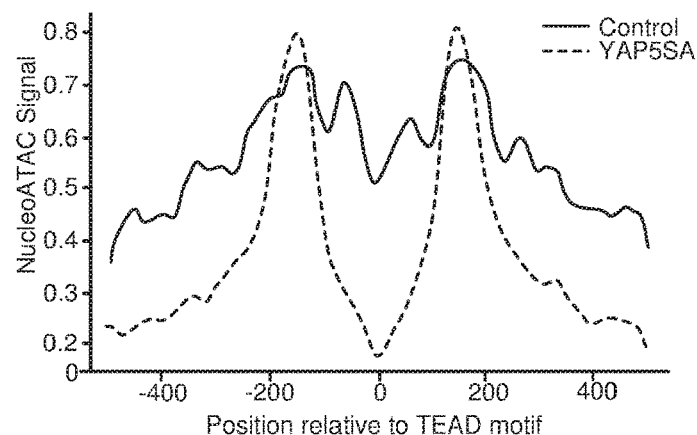

To investigate the Yap5SA OE CM chromatin landscape, an assay was performed for transposase accessible chromatin (ATAC)-seq on PCM-1 isolated CM nuclei[24]. In total, 16,189 peaks showed increased accessibility in Yap5SA CMs, while 13,353 ATAC peaks were diminished compared to control CMs (FIGS. 4A, 9). De novo motif discovery revealed that the top three enriched motifs within newly opened ATAC peaks in Yap5SA OE CMs all belonged to the transcription factor TEAD (FIG. 4B), a well-known Yap interactor[25]. Other enriched motifs were AP-1 elements consistent with previous Yap ChIP-seq data and Atf3 that has a role in preventing pathologic cardiac remodeling[26-28] The Nucleo-ATAC algorithm was applied to illustrate the open state of chromatin relative to TEAD DNA binding motifs and found nucleosome depletion at TEAD motifs, consistent with increased transcription factor occupancy[29] (FIG. 4B).

Figure 4C:
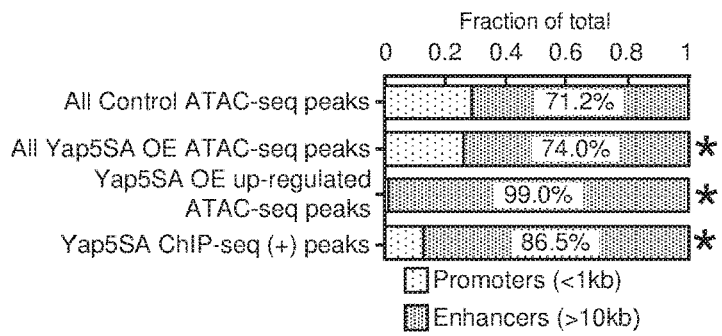
Figure 4D:
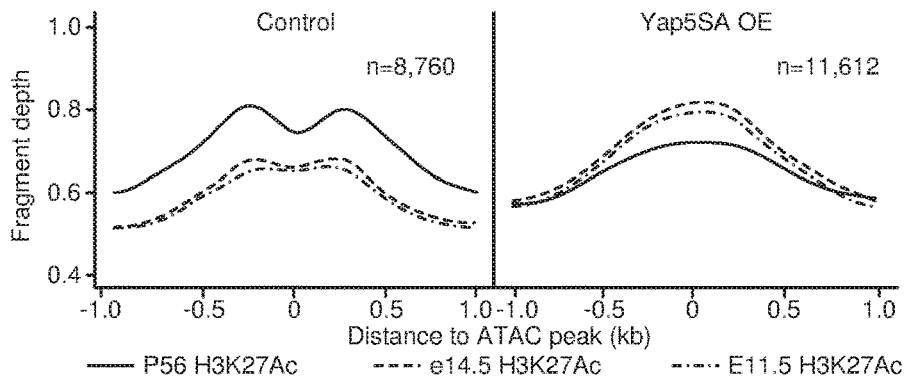
Figure 12A:
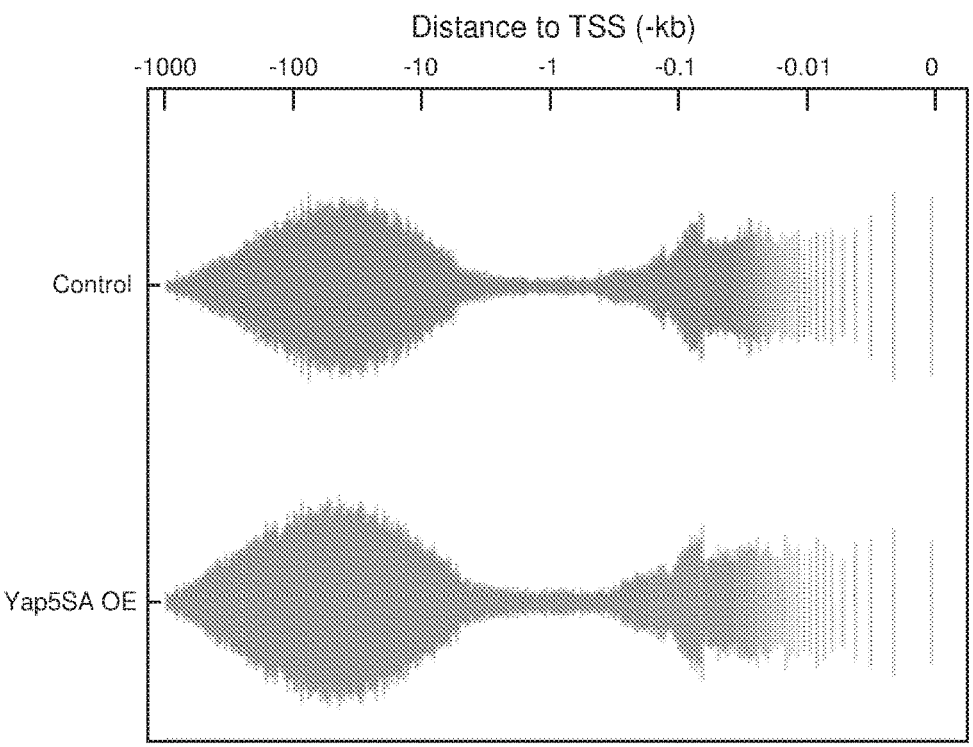
FIGS. 12A-12B. Geometric dot plots of intergenic ATAC-seq peaks relative to TSS.
Figure 12B:
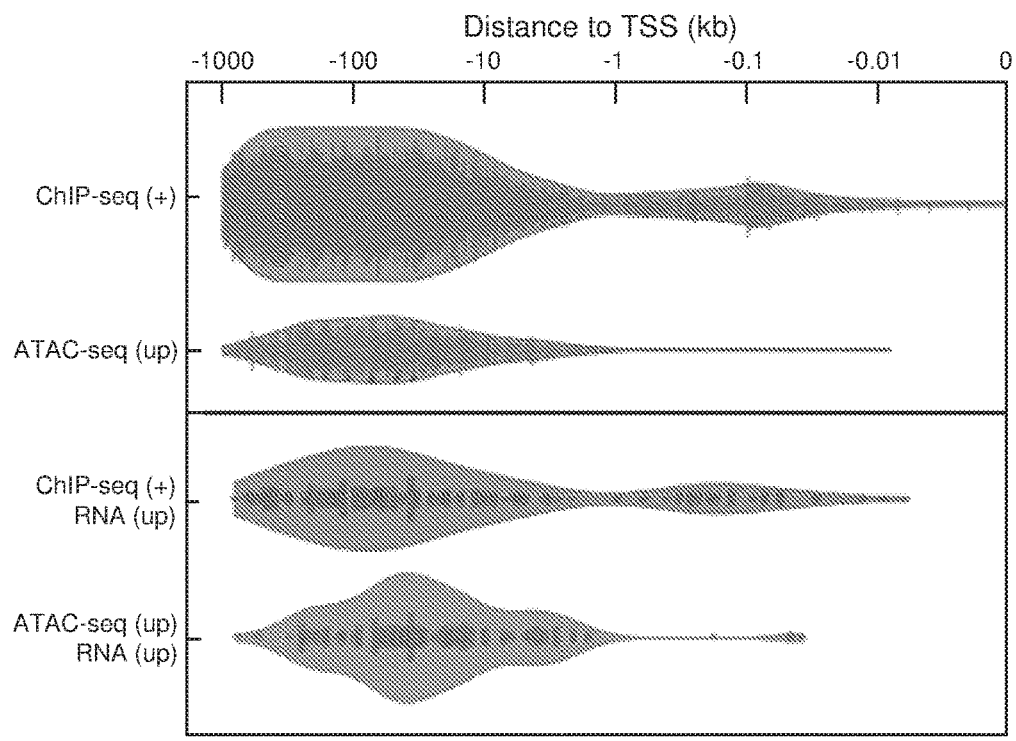

Intergenic ATAC peaks were plotted relative to the nearest transcription start sites (TSS) and there was a bimodal distribution containing promoter regions (<1 kb from TSS) and distal loci (>10 kb) in both control and Yap5SA OE CMs (FIG. 12A). Upregulated, newly accessible, ATAC peaks in Yap5SA OE CMs (adjusted p-value<1e-5) were primarily located distally within putative enhancers[24]. Likewise, ATAC peaks that map to actively transcribed genes were also enriched in distal regions (FIG. 4C, 12B). Previous work revealed that Yap-Tead binding sites were enriched for H3K27Ac, a marker of active chromatin[5]. Comparison of ATAC-seq data to existing H3K27Ac ChIP-seq data from developing and adult heart revealed that ATAC-seq peaks from Yap5SA OE CMs (adjusted p-value≤0.035) were enriched for embryonic H3K27Ac chromatin marks. In contrast, ATAC-seq peaks from control CMs (adjusted p-value≤0.035) showed enrichment for adult H3K27Ac chromatin marks[30] (FIG. 4D). These data suggest that Yap5SA promoted chromatin accessibility at developmental enhancers.

ChIP-seq was performed using an antibody against the Yap5SA Flag epitope to pulldown Yap5SA bound chromatin. Consistent with ATAC-seq data, Yap5SA ChIP-seq revealed that Yap5SA preferentially bound distal enhancer regions in approximately a 6.3 to 1 ratio (FIG. 4C)[26,31]. Yap also bound accessible promoters to positively regulate transcription of normally silent genes[31].

Figure 4E:
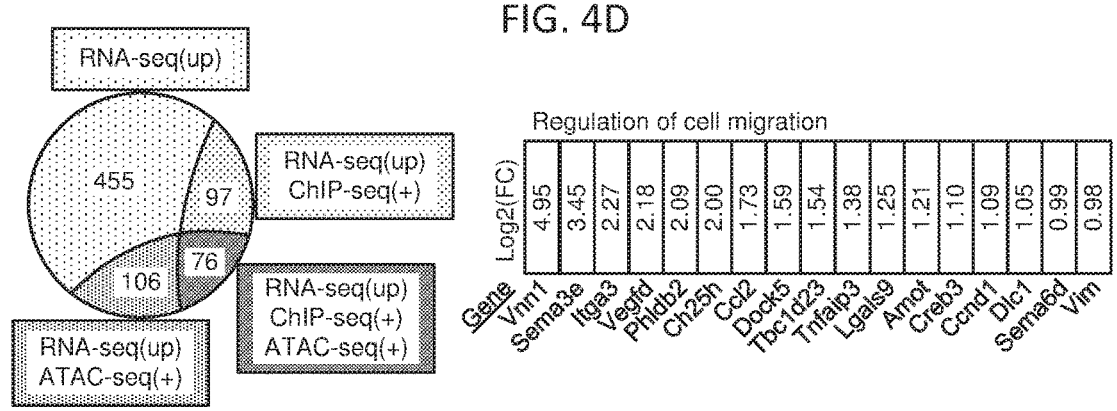
Figure 4E:
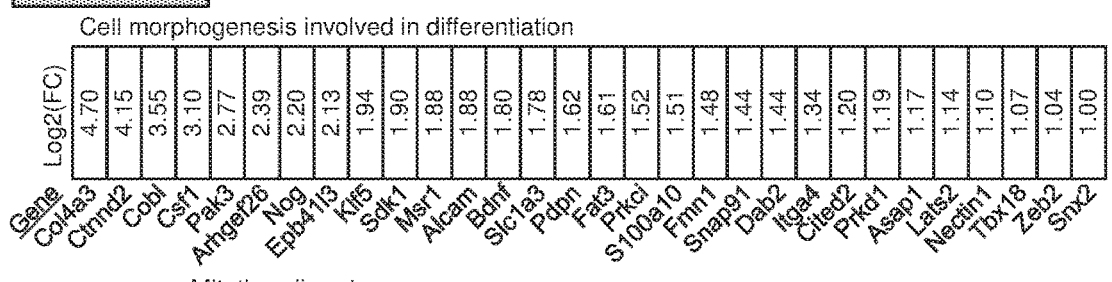
Figure 4E:
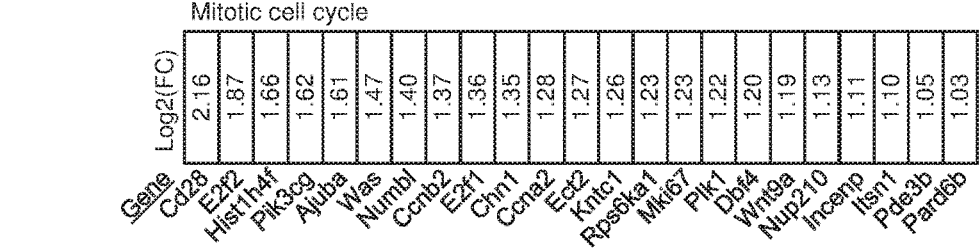
Figure 13B:
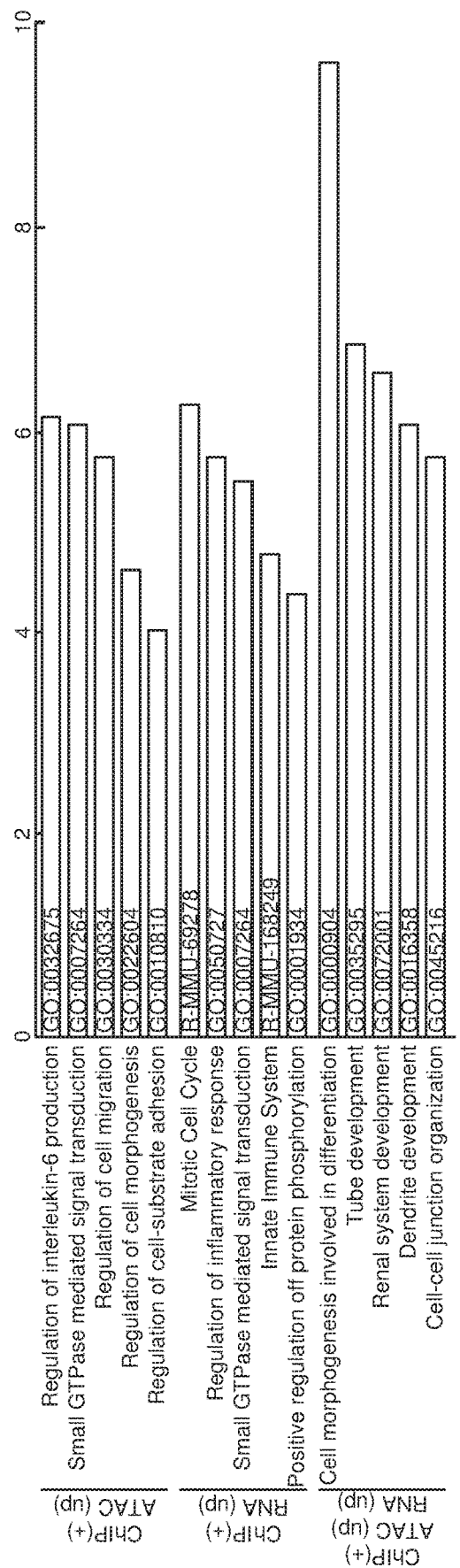
FIG. 13B. Most enriched gene ontology terms for the lists in A.
Figure 13D:
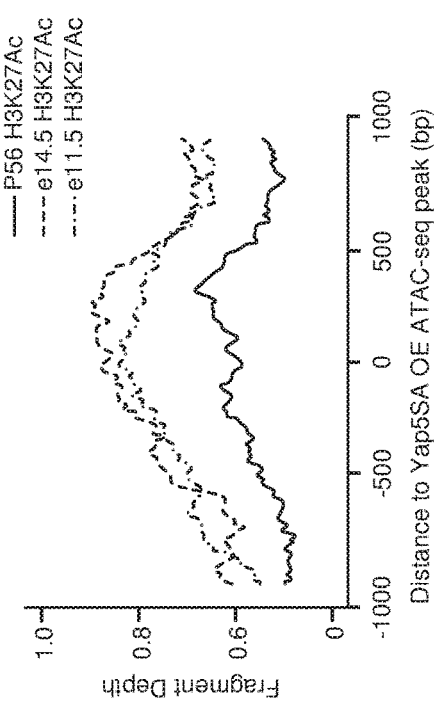
FIG. 13D. H3K27Ac ChIP-seq fragment coverage centered on the ATAC-seq peaks mapping to the 76 Yap target genes that show increased open chromatin.
Figure 13C:
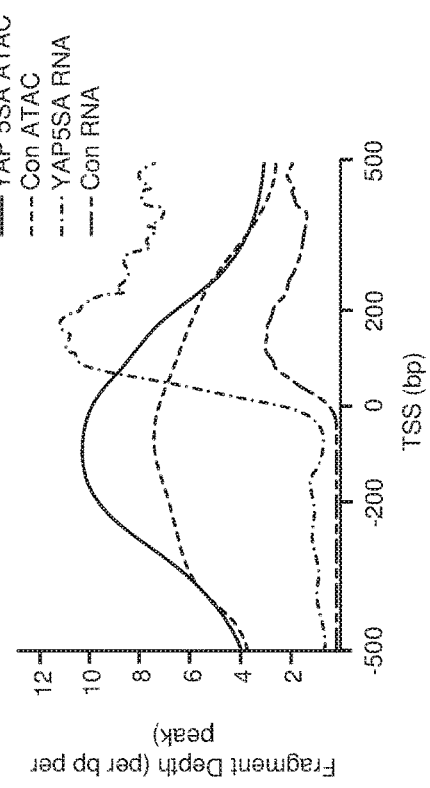
FIG. 13C. Averaged ATAC-seq and RNA-seq reads centered on the TSS of the 76 Yap target genes that show increased open chromatin.

Transcriptionally up-regulated genes were compared in Yap5SA CMs with Yap5SA ChIP-seq data and there were 173 genes were direct Yap5SA target genes. Of the direct Yap5SA target loci, 76 loci also had increased chromatin accessibility as determined by ATAC-seq while the other Yap5SA target loci already had an open chromatin signature (FIGS. 4E, 13A). Plotting the mean fragment depth for both the RNA-seq and ATAC-seq around a 1 kb window centered at the TSS of each gene revealed a pattern of high promoter accessibility and increased transcription at those loci (FIG. 13C).

Figure 4F:
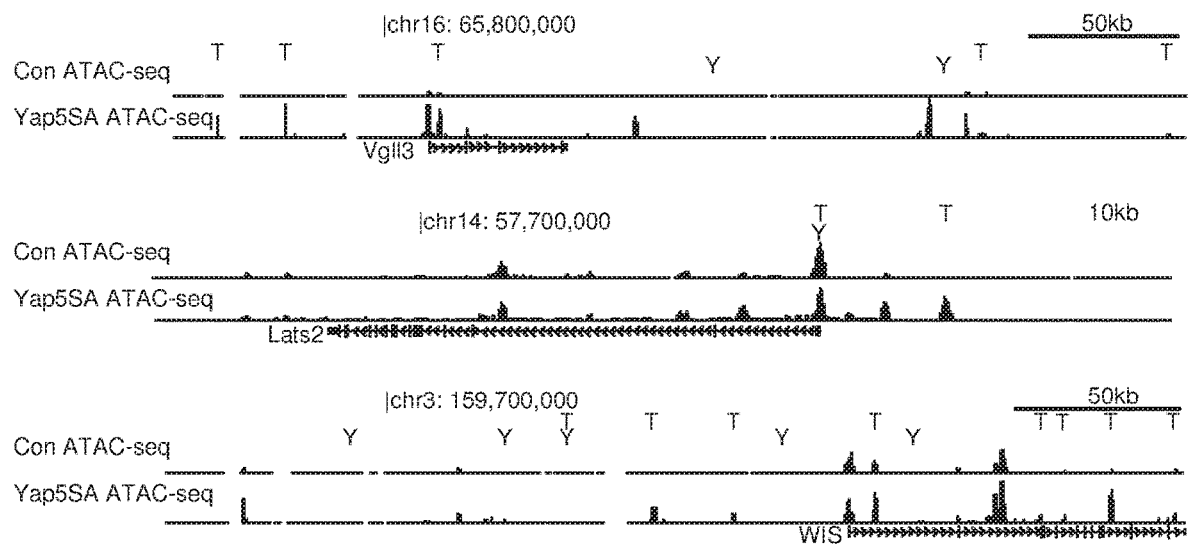
Figure 4G:
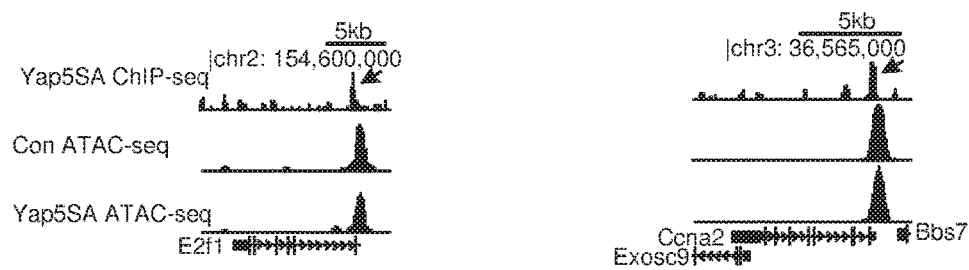
Figure 4G:
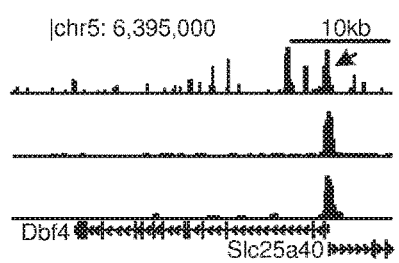
Figure 11A:
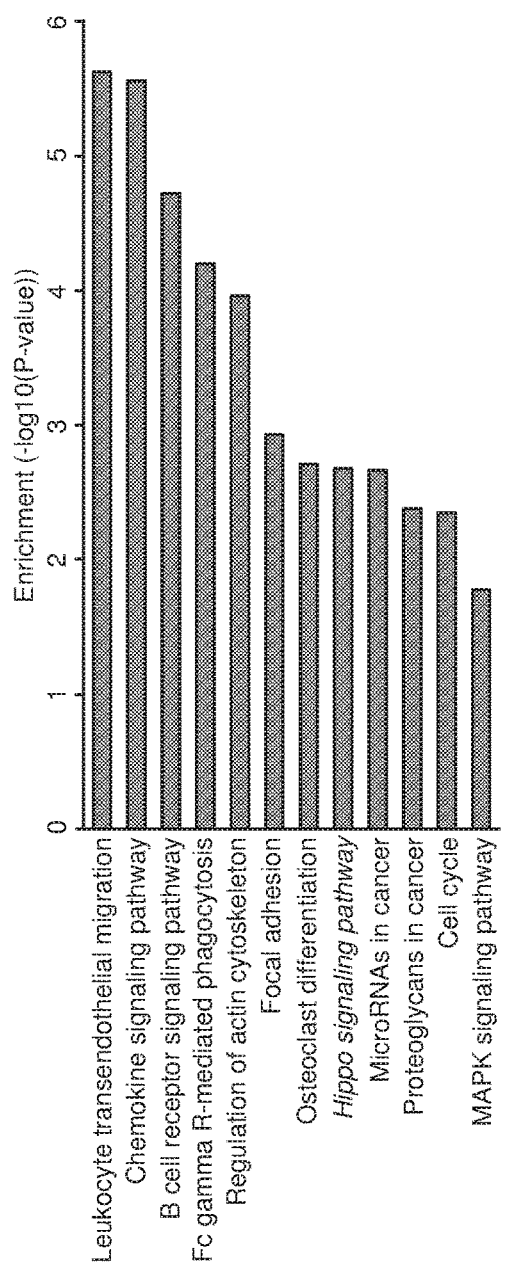
FIG. 11A. Pathway enrichment analysis on genes up-regulated in Yap5SA OE CMs indicated by RNA-seq. Highlighted is the Hippo pathway. (Pathway analysis carried out with g:Profiler) FIG. 11B. (Left) Western blot showing increased endogenous Yap phosphorylation in the Yap5SA OE hearts. (Right) Quantification of the band intensities, shown as mean+/−SEM (control n=4, Yap5SA OE n=3, P<0.01 by ANOVA with Bonferroni post-hoc tests).
Figure 11B:
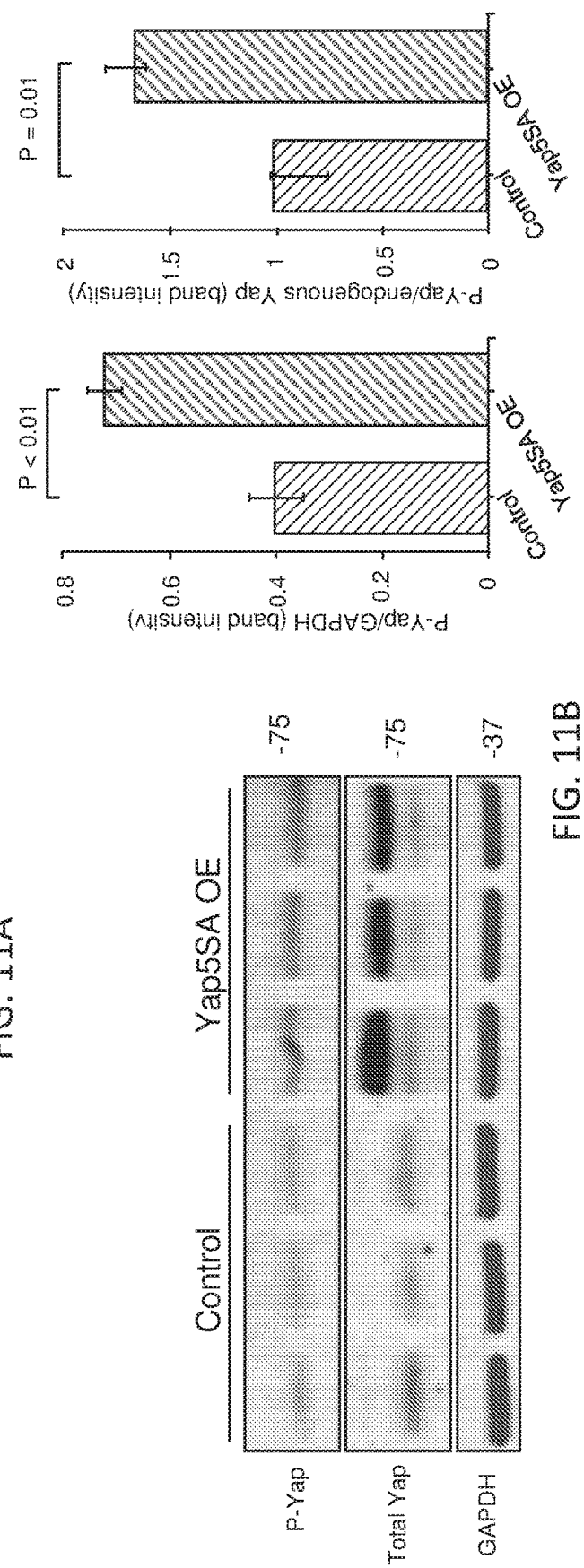

Among the 76 genes directly regulated by Yap5SA were Hippo pathway components, indicating that Yap directly activates a negative feedback loop to prevent CM proliferation (FIG. 4G, 11A-11B). The Hippo pathway genes included Lats2, Vgll2, Vgll3, and Wwc1[8,32] (FIG. 4F; 13A). Western blots revealed that endogenous, lower molecular weight Yap had increased serine 112 phosphorylation indicating upregulated Hippo activity (FIG. 11). Other genes directly regulated by Yap5SA included mitosis and cytokinesis genes such as Pkci[33]. A major category of accessible Yap5SA targets were genes encoding endosomal sorting components. This category included Snx2, Snx7 that encode retromer components. Dab2, encoding an endocytic adaptor protein, functions as a Wnt inhibitor while Wls is essential for endosomal trafficking of Wnt ligands[34,35] (FIGS. 13A1-13A3, 13B).

Genes that promote adherens junction assembly, such as Nectin1, Plekha7, Mtss1, and Ctnnd1, were also accessible Yap5SA targets further supporting the finding that new CMs functionally integrate into the heart[36]. Multiple genes that regulate the actin cytoskeleton were also found in the accessible Yap5SA targets. Ephexin and Pak3 encode proteins that are important to enhance Rho activity. Other genes such as Cobl, encoding an encode actin nucleator, and Cnn3, important in formation of stress fibers during wound healing. (FIGS. 13A1-13A3, 13B)

Figure 14C:
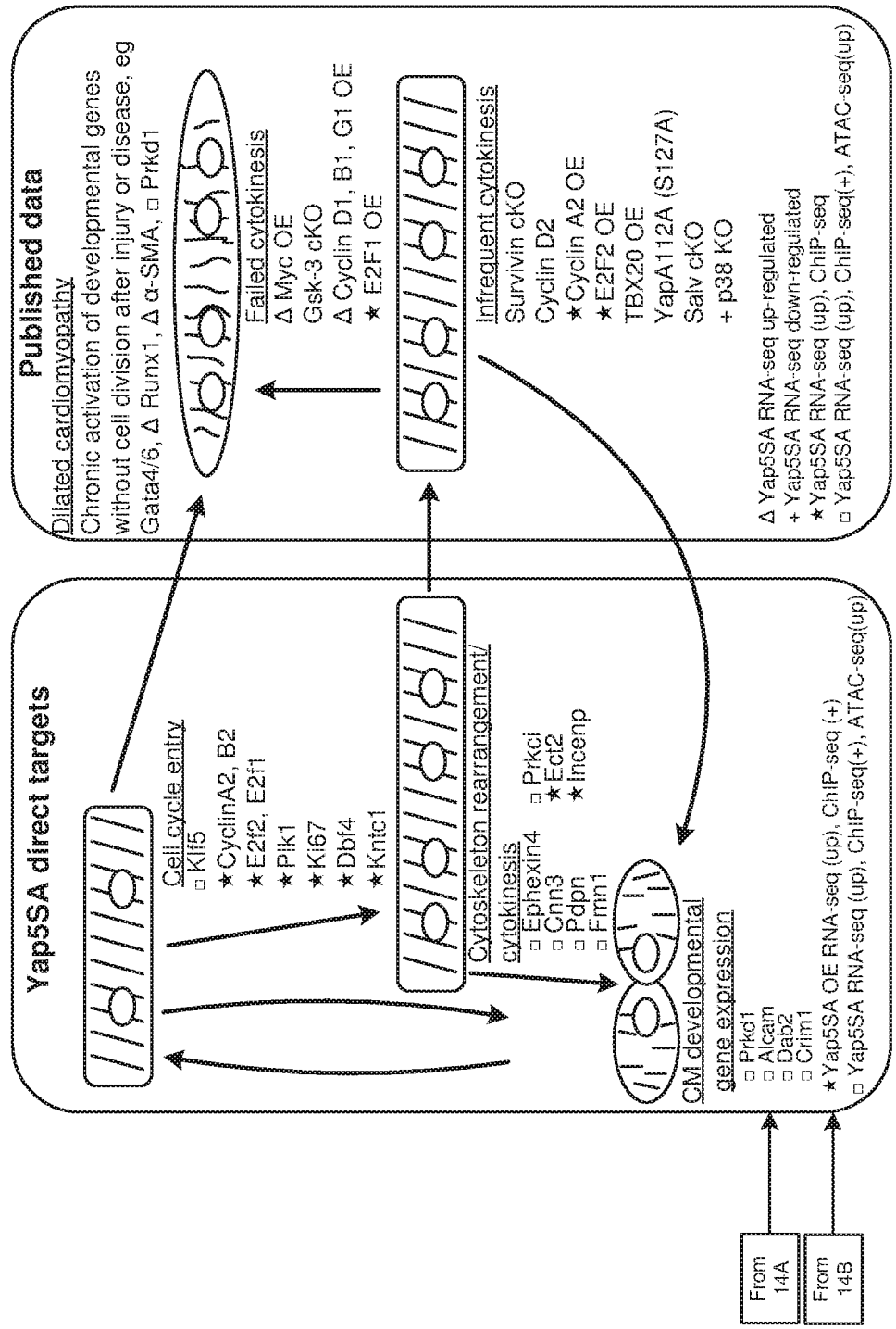

FIG. 14C summarizes genes differentially regulated by Yap5SA that are directly involved with the cell cycle, as well as summarizes the previous literature that described or attempted to initiate the cell cycle in adult cardiomyocytes. The key indicates (symbol) genes that are differentially regulated up or down in Yap5SA cardiomyocytes as determined by RNA-seq; genes that are direct targets of Yap5SA determined by Yap5SA chromatin immunoprecipitation, followed by sequencing (i.e. ChIP-seq(+); and genes that are epigenetically repressed in control cardiomyocytes, but not repressed in the presence of Yap5SA, as determined by assay for transposase accessible chromatin (i.e. ATAC-seq (up)).

The findings reveal that differentiated CMs proliferative capacity is effectively obstructed by decommissioned distal regulatory elements. By overexpressing Yap5SA, it was determined that Yap can activate a genetic program that promotes progression through mitosis. Importantly, Yap5SA target genes include cell cycle genes but also genes encoding endosomal sorting proteins that are important for productive cell division.

Movies produced by the inventors show short axis B-mode echocardiography of a Yap5SA OE heart before tamoxifen administration and of the same heart but, one day after tamoxifen administration and 4 days after. Movies also demonstrate short axis B-mode echocardiography of a Yap5SA OE Heart 2 days after the final tamoxifen dose, and 24 hours before that animal died. The ventricular chamber was diminished. Long axis B-mode echocardiography of a Yap5SA OE heart before tamoxifen and of the same heart but two days after tamoxifen, and then 5 days after. Thickening of the myocardium was evident.

Supplemental Materials

Materials and Methods
Experimental Animals

Mouse studies were performed in accordance with Baylor College of Medicine's institutional animal care and use committee. The inventors utilized pCMV-flag YAP2 5SA from Kunliang Guan (Addgene plasmid #27371), which was cloned into the CAG-loxP-eGFP-Stop-loxP-IRES-βGal expression construct as an example. This construct codes for a human Yap variant that has eight serine residues mutated to alanine at the five canonical Lats-dependant phosphorylation motifs (S61A, S109A, S127A, S128A, S131A, S163A, S164A, S381A). The Yap5SA OE (Tg(Jojo-Flag:: Yap5SA)5JFM) mice were generated by pronuclear injection of linearized DNA encoding the transgene (FIG. 1A) into fertilized oocytes from FVB/N mice, which were then implanted into pseudopregnant ICR mice. Single crosses were performed with homozygous αMyHC-Cre-ERT2 mice, which were maintained on the C57Bl/6 background. All control animals were littermates or age-matched siblings. Genotype was determined both visually by eGFP expression in the tail skin and by PCR genotyping (F:AAGCCTTGACTTGAGGTTAG (SEQ ID NO:5), R:CGTCATCGTCTTTGTAGTCC; SEQ ID NO:6). All adult experiments were performed on male and female mice, 7-10 weeks of age. Tamoxifen induction of Cre was accomplished similarly to previous publications by Heallen, et al. intraperitoneal injections (40 mg/kg), daily for four days[4]).

Ultrasound Echocardiography

M- and B-mode echocardiography were performed according to established protocols at the Baylor College of Medicine Mouse Phenotyping Core using a 30 MHx scanhead (RMV7007B) on a VisualSonics 770 system.

Single Cell Morphological and Physiological Measurements

The day after the fourth tamoxifen injection, cardiomyocytes were isolated by retrograde perfusion of collagenase A (Roche), as described elsewhere[37]. A portion of the cells were fixed (10% formalin, 10 minutes) for cell size quantification, which was accomplished by taking static images of plated cells (Nikon Eclipse 80i microscope, equipped with a Nikon DSFi1 camera), and outlining them in imageJ (NIH, Bethesda, Md., USA) to quantify the CM 2D profile area. The person quantifying the images was blinded to genotype. Live physiological imaging was performed using an IonOptix Myocyte Calcium and Contractility Recording System (IonOptix, Westwood, Mass.). Cardiomyocytes were plated in 1.8 mM $Ca^{2+}$-containing Tyrodes solution (HEPES buffered, pH7.4), selected for absent or minimal of GFP (post-recombination), and were field stimulated using a MyoPacer (IonOptix, Westwood, Mass.) at 20 V/cm; sarcomere shortening was quantified by Fourier transform of the sarcomere periodicity using the Ionoptix IonWizard software during the final 20 seconds of a two-minute, 1 Hz pacing protocol.

Optical Mapping

Mice were anesthetized with isoflurane to the surgical plane of anesthesia, and heparin was injected intraperitoneally (100 units) before cervical dislocation. The heart was then removed and washed in oxygenated (95% 02, 5% $CO_2$), cold Tyrode's Solution. The aorta was then cannulated with a 21 gauge cannula. After cannulation, the heart was retrogradely perfused with Tyrode's solution, maintaining aortic pressure between 80 and 120 mmHg. An electrode (Harvard Apparatus, MA, USA) was placed on the surface of right atrium for pacing stimulations (10 Hz, 12 Hz and 14 Hz), generated by PowerLab 26T (AD Instruments, Sydney, Australia). To eliminate contractile artifacts, hearts were loaded with blebbistatin (Sigma-Aldrich, B0560-5 mg, 50 ul of 2.5 mg/ml in DMSO). The inventors then perfused the hearts with the voltage sensitive dye, di-4-ANEPS (Invitrogen, D-1199, 20 ul of 2.5 mg/ml in DMSO). An LED light was used for excitation (wavelength: 530 nm). Fluorescence Emission, signifying Vm, was long pass filtered (>590 nm, 590FG05-50, Andover Corporation Optical Filter) and measured with a MiCAMO CMOS camera (SciMedia, CA, USA). Surface ECG (ADInstruments) was monitored during experiment using LabChart. Conduction velocities and activation maps were calculated with Rhythm software[38].

Histology, Immunofluorescence, Frozen sections, and EdU imaging

Freshly dissected embryos and postnatal hearts were dissected and imaged for endogenous fluorescence on a Zeiss SteREO Discovery.V12, equipped with a Zeiss Axio-Cam Hrc. For fixation, hearts were retrograde perfused with cardioplegic, 20 mM KCl-PBS, before perfusing 10% neutral buffered formalin, followed by embedding in paraffin. 7 micron transverse sections were cut and mounted onto charged poly-lysine slides (Denville UltraClear Plus, white frosted). A portion were stained with Masson's trichrome stain, and a portion were stained with Picro-sirius red. Immunohistochemistry was performed by first deparaffinizing and rehydrating sections, followed by antigen retrieval. Sections were blocked (10% donkey serum in PBS, 0.1% tween-20) and then stained (separately, in succession) overnight before imaging (primary: anti-CX43, Sigma rabbit 1:200; anti-β-gal, Abcam chicken 1:200) (secondary: standard fluorescently conjugated Life technologies Alexa antibodies). Nuclei were stained with DAPI. TUNEL staining was performed using the DeadEnd Fluorometric TUNEL system (Promega) on paraffin-embedded tissue. The person quantifying the images was blinded to genotype. All imaging was performed on a Zeiss LSM 780 confocal microscope in the Optical Imaging and Vital Micorscopy core at Baylor College of Medicine.

To cut frozen sections, hearts were extracted, perfused with 30% sucrose, 20 mM KCl-PBS, and then placed into Tissue-Tek® O.C.T. compound, before freezing over dry ice. 16 micron sections were then cut and mounted on glass slides. For immunofluorescence staining, antigen retrieval was performed by warming the sections to 42° and then placing in –20° acetone for 20 minutes before blocking with donkey serum and then incubated overnight with primary antibody (PHH3, rabbit Cell Signalin 1:400; AuroraB, rabbit Abcam 1:200; cTnT, mouse Thermo 1:200) at 4°, followed by secondary (Life Technologies Alexa anti rabbit; antimouse Vector Labs biotinylated 1:200, followed by Life Technologies Streptavidin-Alexa) antibody for 30 minutes at room temperature. Nuclei were stained with DAPI. The person quantifying the images was blinded to genotype. All imaging was performed on a Zeiss LSM 780 confocal microscope in the Optical Imaging and Vital Microscopy core at Baylor College of Medicine Immunocytochemistry was performed using standard protocols. Briefly, Langendorff-isolated CMs were fixed for 10 minutes at room temperature in 10% formalin. After permeabilizing with 0.5% triton-100 for 20 minutes and blocking with 2% FBS and 2% BSA, antibodies were incubated (separately, in succession) overnight before imaging (anti-Yap, rabbit Novus 1:200, cTnT, mouse Thermo 1:200) (secondary: standard fluorescently conjugated Life Technologies Alexa antibodies). EdU staining was performed using Click-it technology via Life Technologies' Click-it Alexa Fluor 647 imaging kit (C10340). Bona fide presence of EdU in individual cardiomyocytes was determined by confocal z-stacks. Nuclei number was quantified in these isolated cardiomyocytes by staining with DAPI and counting the number of nuclei per cell by confocal Z-stacks. The person quantifying the images was blinded to genotype. All imaging was performed on a Zeiss LSM 780 confocal microscope.

Western Blotting

Western blotting was performed by bead-homogenizing hearts in a HEPES, EDTA, triton buffer. The lysates were then loaded with a reducing tris-based SDS sample buffer (80 μg/well), and transferred to PVDA membranes, and imaged using the Li-Cor Odyssey imaging system. Primary Antibodies: Novus rabbit anti-Yap (1:1000); Sigma mouse anti-M2flag (1:1000); Millipore mouse anti-GAPDH (1:5000); Cell Signaling Technologies anti-P-Yap(S127—mouse homolog S112)), (1:1000). Li-Cor fluorescent secondary antibodies: goat anti-rabbit IgG, goat anti-mouse IgG (1:5000). Quantitation was performed using the Gel analysis feature in Fiji (ImageJ).

In Vivo Electrophysiology

As previously described[39], electrocardiograms were recorded continuously for 5 days spanning the Yap5SA OE induction protocol. Telemetry transmitters (Data Sciences International) were implanted in the abdominal cavity of ambulatory mice. The s.c. electrodes were placed in a lead II configuration, and recorded using version 4.1 Dataquest software. T-wave measurements were performed by computing the area under the curve.

Quantification of LV Size and Total Number of Myocytes

To determine the total number of cardiomyocytes in the left ventricles, the inventors first excised hearts and fixed them in diastole by retrograde perfusion with KCl, followed by 10% formalin, and then drop fixing in 10% formalin. The hearts were embedded in paraffin, and cut from apex to aorta in 7 micron sections. The inventors then computed the volume of the left ventricle in each heart by plotting the area of LV myocardium on a microscope slide as a function of tissue depth and then then integrated the area under that curve. From that volume, the LV weight to body weight ratio was computed by converting the volume to mass using the density of muscle of 1.053 g/mL[40]. The 7 micron sections at various tissue depths were then stained with anti-PCM1, DAPI, and WGA to label: CM nuclei, all nuclei, and the cell borders. Confocal microscopy was used to image through the entire thickness of each section, and then the inventors counted the number of PCM1(+) nuclei in the imaging frame. Partial nuclei on the bottom and left edges of the frame were not counted, while partial nuclei on the top and right edges were counted. Z-stacks were taken at random throughout sections from different tissue depths (40 Z-stacks/heart). Nuclei were counted only if they were both PCM1 and DAPI positive, with PCM1 encircling the DAPI (FIG. 3F). To find the total number of CMs, the number of nuclei counted per volume was computed to a nucleation density, which was then extrapolated to the entire volume of the myocardium and then corrected for the average nucleation of the myocytes from each genotype (control: 2.04 nuclei/CM; Yap5SA: 1.92 nuclei/CM, FIG. 3G) as described elsewhere. The person quantifying the images was blinded to genotype.

DNA Content Analysis by Flow Cytomotry

Cardiomyocytes were isolated by Langendorff perfusion, and then fixed in 10% formalin. Nuclei were isolated as previously described[42]. Cells were suspended and dounce homogenized 30 times in HB buffer (pH 7.4 15 mM Tris-HCl, 0.34 M sucrose, 15 mM NaCl, 60 mM KCl, 0.2 mM EDTA, 0.2 mM EGTA with proteinase inhibitors). The nuclei were then released by passage through an 18-G needle 15 times in PBTB buffer (0.1% Triton X-100, 5% BSA in PBS). To label CM-specific nuclei, the nuclei were incubated with PCM1 antibody (1:1000, Sigma; secondary: Life Technologies Alexa anti-rabbit 546), and DNA was labelled with DAPI. The nuclei were then run through a cell sorter (BD Biosciences FACSARIA II SORP), and PCM1 (+) cardiomyocyte nuclei DNA content was quantified as DAPI fluorescence intensity and analyzed using FlowJo software (Tree Star) for cell cycle stage.

LacZ Reporter Doubling Time Analysis

Hearts were dissected out, perfused with 20% glycerol in 20 mM KCl, embedded in O.C.T. compound, and frozen over dry ice. They were then sectioned into 16 μm sections, fixed for 15 minutes in 0.02% glutaraldehyde in PBS. The reaction with x-gal was allowed to proceed at 37° for 48 hours.

The number of cells resulting from cell division can be described by $N(t)=N_0 2^{2t/t_D}$, where N(t) is the number of cells at a given time, No is the starting number of cells, t is the amount of time that it takes to go from No to N(t), and $t_D$ is the doubling time. A single low dose (10 μg/g) tamoxifen injection was performed, followed by time-dependent sacrifices of the Yap5SA OE mice. The inventors then sectioned the hearts into and quantified the number of LacZ(+) cells per section. That total was then divided by the area of the section. The inventors then plotted the log 2 of those values and fitted the data to a linear function described by $$\log_2(N(t)) = \log_2(N_0) + \frac{2t}{t_D} (R^2 = 0.96).$$

By inserting data for $N_0$ and N(t), rearranging, and solving for $t_D$, the doubling time ($t_D$) was determined. Imaging was performed on a Nikon Eclipse 80i microscope, equipped with a Nikon DSFi1 camera). The person quantifying the images was blinded to the time point.

PCM1 Nuclear Isolations for ATAC-Seq and RNA-Seq:

Nuclear isolation was performed according to Mo et al. with the following modifications[43]. Briefly, fresh cardiac tissue was harvested on ice and immediately homogenized with a Biogen Series PRO200 (PRO Scientific) prior to dounce homogenization. Nuclei were isolated via density gradient centrifugation with optiprep density gradient medium (Sigma). All nuclei isolated from 30-40% interface were pre-cleared with Protein-G Dynabeads (Life technologies). Next, nuclei were immunoprecipitated with an anti-PCM1 (Sigma, HPA023370) antibody and Protein-G Dynabeads to enrich for cardiomyocyte nuclei[21].

ATAC-seq

Approximately 50,000 bead-bound PCM1+ nuclei were used as input for ATAC-seq. ATAC-seq libraries were generated according to (Buenrostro et al., 2013)[24]. Paired-end 2×75 bp sequencing was performed on an Illumina Nextseq instrument (DNA Link). Reads were mapped to the mouse genome (mm10) using Bowtie2 with default paired-end settings[44]. Next, all non-nuclear reads, and improperly paired reads were discarded. Duplicated reads were next removed with picard MarkDuplicates. Peak calling was carried out with MACS2 (callpeak—nomodel—broad). Blacklisted regions were lifted over from mm9 to mouse genome mm10 and removed along with peaks of low sequencing quality (require>q30). Reads were counted for each condition from the comprehensive peak file (Yap5SA and control replicates merged) using bedtools (multicov module)[45]. Quantile normalization of ATAC-seq data sets was performed with CQN[46], and offsets were fed into DESeq2 to quantify differential accessibility[47]. Nucleosome calling was carried out with NucleoATAC[29]. Motif enrichment analysis was conducted with Homer (findMotifsGenome.pl).

RNA-seq

RNA from Bead-bound PCM1+ nuclei was collected using the RNEasy Plus Micro kit (Qiagen). Nuclear RNA-seq libraries were constructed with the Stranded RNA-seq Kit with Ribo Erase (Kapa Biosystems) with custom Y-shaped adapters. Paired-end 2×75 bp sequencing was performed for RNA-seq libraries on an Illumina Nextseq instrument (DNA Link). Reads were first mapped to the mouse genome (mm10) using STAR[48]. Differential expression analysis was then carried out with DESeq2[47]. Gene ontology was performed using Metascape. De novo pathway analysis was performed using g:Profiler[49,50].

H3K27Ac ChIP-seq

Publicly available data: GSM1264370, GSM1264372, GSM1264372, and GSM1264372 were mapped to the mouse genome (build mm10) using bowtie2 default parameters. Following mapping, the heart E11.5 H3K27Ac replicates GSM1264370, and GSM1264372 were merged prior to analysis. Gene tracks were shown using the UCSC genome browser.

Yap ChIP-seq

Ventricles were dissected into cold DPBS to remove blood and then minced in PBS supplemented with 0.1% TritonX-100. They were then quickly homogenized with BioGen Pro200 and a 5 mm generator. Crosslinking was achieved in 1% formaldehyde at room temperature for 10 minutes on a rotator and quenched with 150 mM Glycine at room temperature for 10 minutes. Cells were pelleted and rinsed twice with with 0.1% Triton-PBS. Then they were lysed by incubating on ice for 20 minutes in 5 mL cell lysis buffer (5 nM Tris pH 8.0, 140 mM NaCl, 1 mM EDTA, 10% Glycerol, 0.5% NP-40, 0.25% TritonX-100, 0.5% Igepal CA-630, 50 mM HEPES, cOmplete EDTA-Free Roche protease inhibitors) and then dounce homogenized. Lysates were pelleted, resuspended in cell lysis buffer, and sonicated. Then, the inventors pelleted cells and nuclei at 2 kG for 10 minutes at 4 C, followed by resuspention in 600 uL nuclear lysis Buffer (10 mM Tris, 1 mM EDTA, 0.5 mM EGTA, 0.3% SDS, complete EDTA-Free Roche protease inhibitors) and sonicated. 15 ug sheared chromatin was used for ChIP with Flag antibody (Sigma, F1804) or IgG (Milipore 12-371) and Protein-G magnetic beads (Peirce), at 4 C overnight on rotator. Beads were washed for 5 min at 4 C on rotator, washed, de-crosslinked and DNA was purified. Sequencing libraries were prepared using the Kappa Library Preparation Kit (Ion Torrent, KK8301). YAP5SA-FLAG ChIP-seq libraries sequenced on the Ion Torrent Proton were mapped to the mm10 mouse genome assembly using Torrent Suite aligner Tmap (0.2.3) (Life Technologies). Three biological replicates were performed and only the uniquely mapped reads were kept. Peaks were called and annotated with HOMER (findPeaks and annotatePeaks.pl) from the combined YAP5SA ChIP-seq data set. Gene tracks were shown using the UCSC genome browser.

Example 2

YAPK265R Stability

Figure 15B:
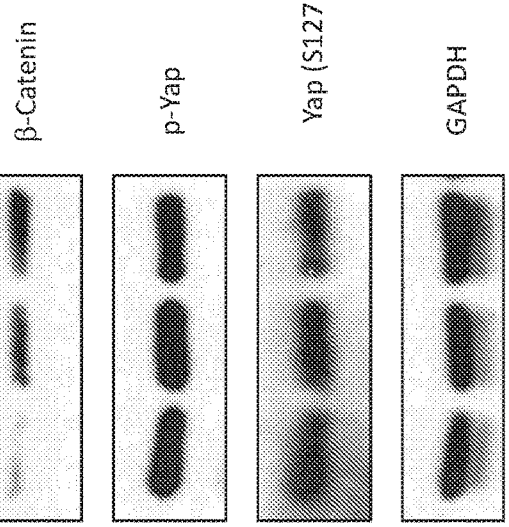
FIGS. 15A-15B. Yap K265R is less stable than WT Yap.
Figure 15A:
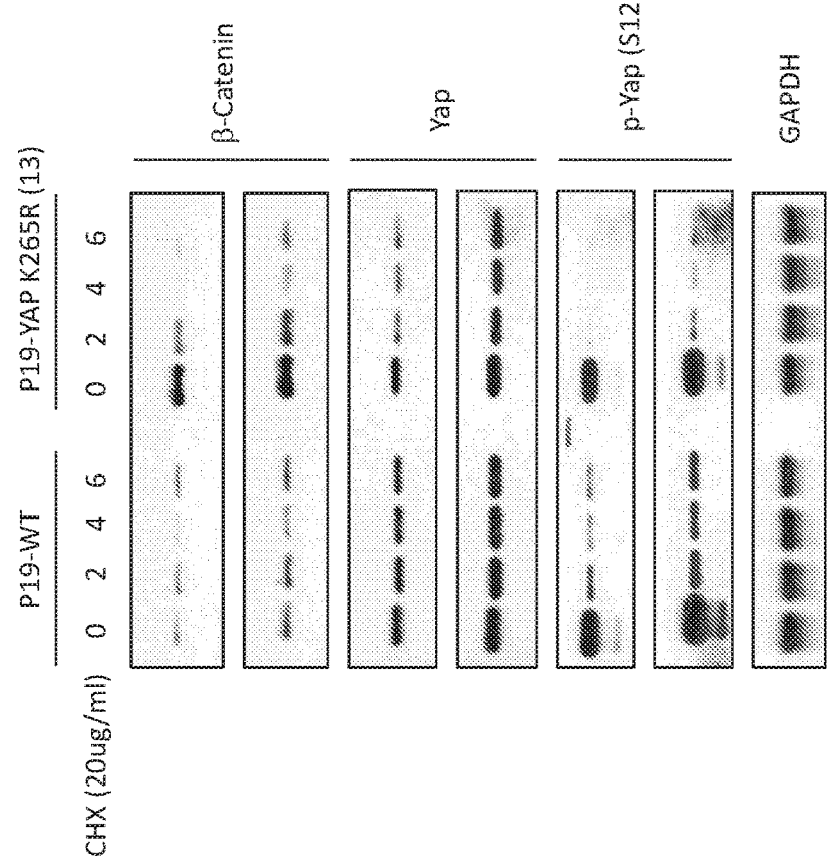

The inventors generated two P19 cell lines (No. 11 and No. 13) with Yap K265R (mutation of lysine to arginine on the 265 amino acid of Yap) homozygous mutation. To check the half-life of the YapK265R mutant, WT P19 cells and P19 cells were seeded with Yap K265R mutation (No. 13) in 6-well-plate. The next day, when the cells reach~60%-70% confluency, the cells were treated with 20 ug/ml cycloheximide (CHX) for 2, 4, or 6 hours (cells treated with DMSO as 0 hours). After treatment, cells were washed with ice-cold PBS twice and then harvested with 100 ul 0.5% NP40 lysis buffer (50 mM Tris-HCL, 150 mM NaCl, 0.5% NP40 and Protease inhibitor and phosphorylation inhibitor). Cell lysates were analyzed by western blotting to test the expression of Yap, Yap with S127 phosphorylation (p-Yap), and β-catenin. GAPDH expression was used as the internal control (FIG. 15A). CHX can inhibit protein synthesis, because without nascent protein supplement after treatment, the protein levels of Yap, p-Yap and β-catenin decreased by time. Compared with WT Yap, YapK265R decreased faster that means Yap with the K265R mutation is less stable (FIG. 15A). p-Yap and β-catenin are also less stable in YapK265R mutant P19 cells (FIG. 15A). Without CHX treatment, the basal level of Yap and p-Yap are slightly lower in YapK265R mutant P19 cells compared with WT P19 cells (FIG. 1B). Interestingly, β-catenin expression was increased in P19 cells with YapK265R mutation (FIGS. 1A and 1B).

Figure 16:
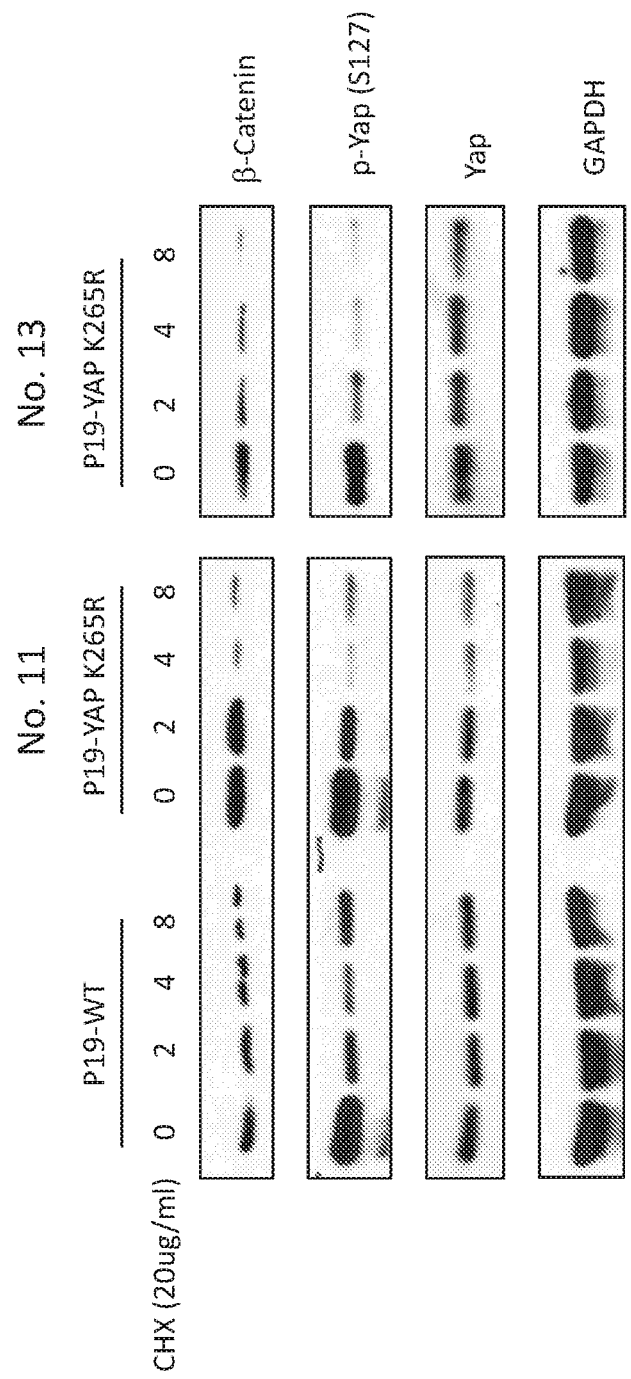
FIG. 16. Demonstrates determination of Yap mutant protein stability. WT P19 cells and P19 cells with YapK265R mutation treated with 20 ug/ml cycloheximide for 0, 2, 4 and 8 hours, and harvested with 0.5% NP40 lysis buffer. Immunoblotted for the antibodies as indicated.
Figure 17B:
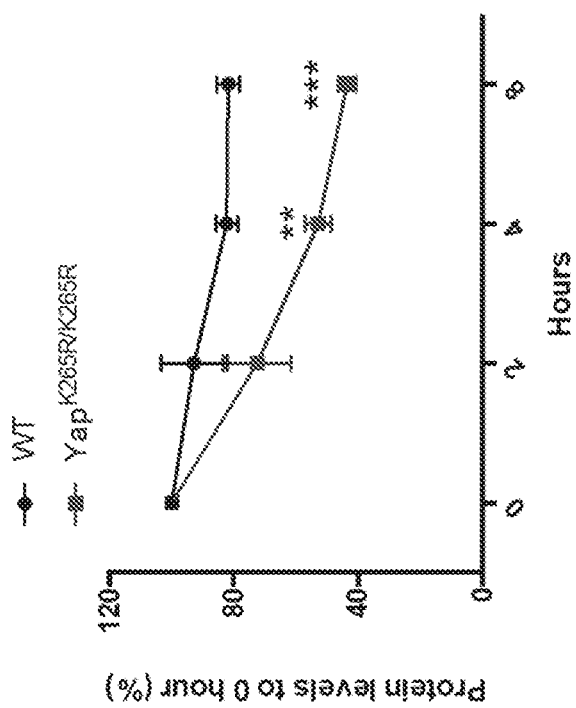
FIGS. 17A-17B. Determination of Yap mutant protein stability.
Figure 17A:
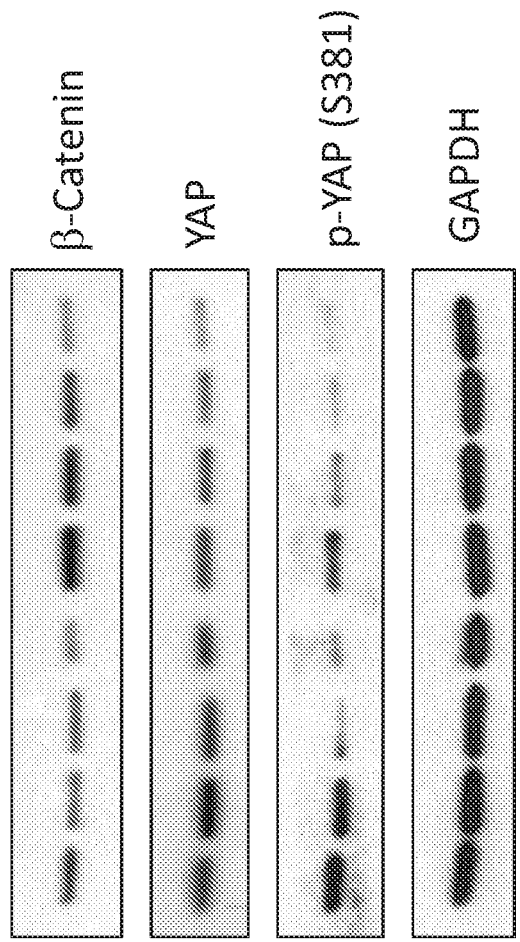
Figure 18B:
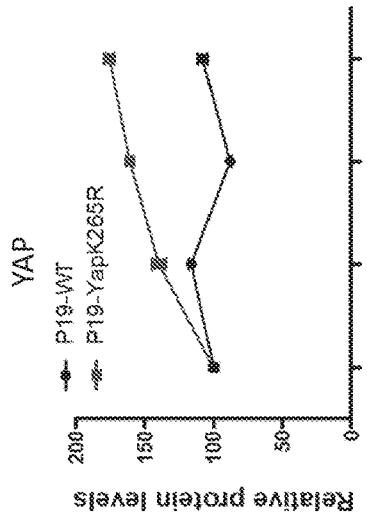
FIGS. 18A-18C. Determination of Yap mutant protein turnover rate.
Figure 18C:
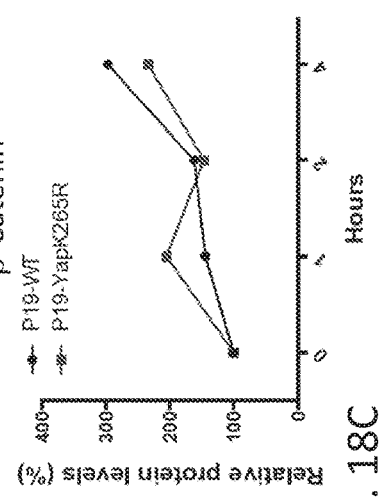
Figure 18A:
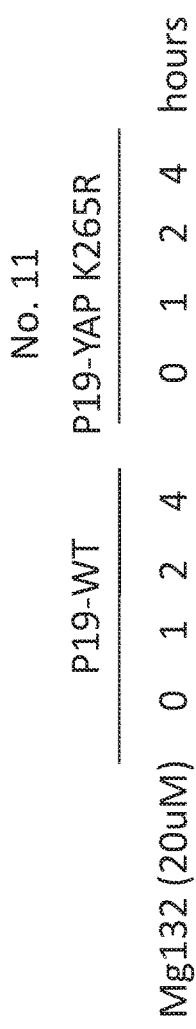

These studies were repeated twice with consistent results (FIG. 16 and FIG. 17), and the statistic result is shown in FIG. 17B. To test the protein turnover rate of Yap, the cells were treated with 20 um/ml Mg132, which is a proteasome inhibitor; protein levels increased with time because of the inability to degrade. More Yap protein accumulation in YapK265R mutant P19 cells indicates YapK265R has a higher turnover rate as compared with WT Yap; in other words, YapK265R is less stable than WT Yap (FIGS. 18A and 18B). However, the turnover rate of β-catenin was unchanged in YapK265R mutant cells (FIGS. 18A and 18C).

Yap is a transcriptional cofactor that works together with DNA binding partners in nuclear to regulate gene expression. To test the nuclear localization of YapK265R mutant, P19 cells were lysed, and the nuclear and cytosol fractions were harvested for western blotting analysis. Yap protein amount is less in the nuclear fraction but unchanged in the cytosol fraction of YapK265R mutant cells, that suggest less nuclear localization of YapK265R (FIG. 19). This experiment was performed twice and with total three replicates (FIGS. 19A and 19B). The statistic result is shown in FIGS. 19C and 19D.

Examples of Antibodies: Yap (1:1000, Novas Biologicals, NB110-58358); β-catenin (1:1000, Santa Cruz, sc-7963); p-Yap (S127) (1:1000, Cell Signaling, #4911); p-Yap (S381) (1:1000, Cell Signaling, #13619); GAPDH (1:3000, Abcam, ab9485); HDAC2 (1:5000, Thermo Scientific, PA1-861)

REFERENCES

All patents, patent applications, and publications cited herein are hereby incorporated by reference in their entirety herein.

1 Bergmann, O. et al. Dynamics of Cell Generation and Turnover in the Human Heart. *Cell* 161, 1566-1575, doi:10.1016/j.cell.2015.05.026 (2015).
2 Soonpaa, M. H. & Field, L. J. Assessment of cardiomyocyte DNA synthesis in normal and injured adult mouse hearts. *The American journal of physiology* 272, H220-226 (1997).
3 Yu, F. X., Zhao, B. & Guan, K. L. Hippo Pathway in Organ Size Control, Tissue Homeostasis, and Cancer. *Cell* 163, 811-828, doi:10.1016/j.cell.2015.10.044 (2015).
4 Heallen, T. et al. Hippo signaling impedes adult heart regeneration. *Development* 140, 4683-4690 (2013).
5 Morikawa, Y. et al. Actin cytoskeletal remodeling with protrusion formation is essential for heart regeneration in Hippo deficient mice. submitted (2015).
6 Xin, M. et al. Hippo pathway effector Yap promotes cardiac regeneration. *Proc Natl Acad Sci USA* 110, 13839-13844, doi:10.1073/pnas.1313192110 (2013).
7 Lin, Z. et al. Cardiac-specific YAP activation improves cardiac function and survival in an experimental murine MI model. *Circulation research* 115, 354-363, doi: 10.1161/circresaha.115.303632 (2014).
8 Zhao, B., Li, L., Tumaneng, K., Wang, C. Y. & Guan, K. L. A coordinated phosphorylation by Lats and CK1 regulates YAP stability through SCF(beta-TRCP). *Genes & development* 24, 72-85, doi:10.1101/gad.1843810 (2010).
9 Sultana, N. et al. Optimizing Cardiac Delivery of Modified mRNA. *Mol Ther* 25, 1306-1315, doi:10.1016/j.ymthe.2017.03.016 (2017).
10 Chatterjee, K., Zhang, J., Honbo, N. & Karliner, J. S. Doxorubicin cardiomyopathy. *Cardiology* 115, 155-162, doi:10.1159/000265166 (2010).
11 Florido, R., Smith, K. L., Cuomo, K. K. & Russell, S. D. Cardiotoxicity From Human Epidermal Growth Factor Receptor-2 (HER2) Targeted Therapies. *J Am Heart Assoc* 6, doi:10.1161/JAHA.117.006915 (2017).
12 Mathiowitz E1, J. J., Jong Y S, Carino G P, Chickering D E, Chaturvedi P, Santos C A, Vijayaraghavan K, Montgomery S, Bassett M, Morrell C. Biologically erodable microspheres as potential oral drug delivery systems. *Nature* 386, 410-414, doi:10.1038/386410a0 (1997).

13 Hwang S Jl, P. H., Park K. Gastric retentive drug-delivery systems. *Critical reviews in therapeutic drug carrier systems* 15, 243-284 (1998).

14 Mitsuko Takenaga*, Y. S., Yasutaka Azechi, Akira Ochiai, Yasuo Kosaka, & Rie Igarashi, Y. M. Microparticle resins as a potential nasal drug delivery system for insulin. *Journal of controlled release* 52, 81-87 (1996).

15 Sohal, D. S. et al. Temporally regulated and tissue-specific gene manipulations in the adult and embryonic heart using a tamoxifen-inducible Cre protein. *Circulation research* 89, 20-25 (2001).

16 Bersell, K. et al. Moderate and high amounts of tamoxifen in alphaMHC-MerCreMer mice induce a DNA damage response, leading to heart failure and death. *Disease models & mechanisms* 6, 1459-1469, doi:10.1242/dmm.010447 (2013).

17 Alkass, K. et al. No Evidence for Cardiomyocyte Number Expansion in Preadolescent Mice. *Cell* 163, 1026-1036, doi:10.1016/j.cell.2015.10.035 (2015).

18 Bersell, K., Arab, S., Haring, B. & Kuhn, B. Neuregulinl/ErbB4 signaling induces cardiomyocyte proliferation and repair of heart injury. *Cell* 138, 257-270, doi:10.1016/j.cell.2009.04.060 (2009).

19 Castedo, M. et al. Cell death by mitotic catastrophe: a molecular definition. *Oncogene* 23, 2825-2837, doi:10.1038/sj.onc.1207528 (2004).

20 Baildam, A. D. et al. DNA analysis by flow cytometry, response to endocrine treatment and prognosis in advanced carcinoma of the breast. *British journal of cancer* 55, 553-559 (1987).

21 Gilsbach, R. et al. Dynamic DNA methylation orchestrates cardiomyocyte development, maturation and disease. *Nature communications* 5, 5288, doi:10.1038/ncomms6288 (2014).

22 Preissl, S. et al. Deciphering the Epigenetic Code of Cardiac Myocyte Transcription. *Circulation research* 117, 413-423, doi:10.1161/circresaha.115.306337 (2015).

23 Guo, X. & Chen, S. Y. Dedicator of Cytokinesis 2 in Cell Signaling Regulation and Disease Development. *Journal of cellular physiology*, doi:10.1002/jcp.25512 (2016).

24 Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. *Nature methods* 10, 1213-1218, doi:10.1038/nmeth.2688 (2013).

25 Halder, G. & Johnson, R. L. Hippo signaling: growth control and beyond. *Development* 138, 9-22, doi:10.1242/dev.045500 (2011).

26 Zanconato, F. et al. Genome-wide association between YAP/TAZ/TEAD and AP-1 at enhancers drives oncogenic growth. *Nature cell biology* 17, 1218-1227, doi:10.1038/ncb3216 (2015).

27 Stein, C. et al. YAP1 Exerts Its Transcriptional Control via TEAD-Mediated Activation of Enhancers. *PLoS genetics* 11, e1005465, doi:10.1371/journal.pgen.1005465 (2015).

28 Kalfon, R. et al. ATF3 expression in cardiomyocytes preserves homeostasis in the heart and controls peripheral glucose tolerance. *Cardiovascular research* 113, 134-146, doi:10.1093/cvr/cvw228 (2017).

29 Schep, A. N. et al. Structured nucleosome fingerprints enable high-resolution mapping of chromatin architecture within regulatory regions. *Genome research* 25, 1757-1770, doi:10.1101/gr.192294.115 (2015).

30 Nord, A. S. et al. Rapid and pervasive changes in genome-wide enhancer usage during mammalian development. *Cell* 155, 1521-1531, doi:10.1016/j.cell.2013.11.033 (2013).

31 Galli, G. G. et al. YAP Drives Growth by Controlling Transcriptional Pause Release from Dynamic Enhancers. *Molecular cell* 60, 328-337, doi:10.1016/j.molcel.2015.09.001 (2015).

32 Lin, Z. et al. Acetylation of VGLL4 Regulates Hippo-YAP Signaling and Postnatal Cardiac Growth. *Developmental cell* 39, 466-479, doi:10.1016/j.devcel.2016.09.005 (2016).

33 Passer, D., van de Vrugt, A., Atmanli, A. & Domian, I. J. Atypical Protein Kinase C-Dependent Polarized Cell Division Is Required for Myocardial Trabeculation. *Cell reports* 14, 1662-1672, doi:10.1016/j.celrep.2016.01.030 (2016).

34 Hofsteen, P., Robitaille, A. M., Chapman, D. P., Moon, R. T. & Murry, C. E. Quantitative proteomics identify DAB2 as a cardiac developmental regulator that inhibits WNT/beta-catenin signaling. *Proc Natl Acad Sci USA* 113, 1002-1007, doi:10.1073/pnas.1523930113 (2016).

35 Hausmann, G., Banziger, C. & Basler, K. Helping Wingless take flight: how WNT proteins are secreted. *Nature reviews. Molecular cell biology* 8, 331-336, doi:10.1038/nrm2141 (2007).

36 Saarikangas, J. et al. Missing-in-metastasis MIM/MTSS1 promotes actin assembly at intercellular junctions and is required for integrity of kidney epithelia. *Journal of cell science* 124, 1245-1255, doi:10.1242/jcs.082610 (2011).

37 Reynolds, J. O. et al. Junctophilin-2 gene therapy rescues heart failure by normalizing RyR2-mediated Ca(2+) release. *Int J Cardiol* 225, 371-380, doi:10.1016/j.ijcard.2016.10.021 (2016).

38 Laughner, J. I., Ng, F. S., Sulkin, M. S., Arthur, R. M. & Efimov, I. R. Processing and analysis of cardiac optical mapping data obtained with potentiometric dyes. *Am J Physiol Heart Circ Physiol* 303, H753-765, doi:10.1152/ajpheart.00404.2012 (2012).

39 Wang, J. et al. Pitx2-microRNA pathway that delimits sinoatrial node development and inhibits predisposition to atrial fibrillation. *Proc Natl Acad Sci USA* 111, 9181-9186, doi:10.1073/pnas.1405411111 (2014).

40 Vinnakota, K. C. & Bassingthwaighte, J. B. Myocardial density and composition: a basis for calculating intracellular metabolite concentrations. *American Journal of Physiology—Heart and Circulatory Physiology* 286, doi:10.1152/ajpheart.00478.2003 (2004).

41 Brüel, A. & Nyengaard, J. R. Design-based stereological estimation of the total number of cardiac myocytes in histological sections. *Basic research in cardiology* 100, 311-319, doi:10.1007/s00395-005-0524-9 (2005).

42 Bonn, S. et al. Cell type-specific chromatin immunoprecipitation from multicellular complex samples using BiTS-ChIP. *Nature protocols* 7, 978-994, doi:10.1038/nprot.2012.049 (2012).

43 Mo, A. et al. Epigenomic Signatures of Neuronal Diversity in the Mammalian Brain. *Neuron* 86, 1369-1384, doi:10.1016/j.neuron.2015.05.018 (2015).

44 Langmead, B., Trapnell, C., Pop, M. & Salzberg, S. L. Ultrafast and memory-efficient alignment of short DNA sequences to the human genome. *Genome Biology* 10, 1-10, doi:10.1186/gb-2009-10-3-r25 (2009).

45 Quinlan, A. R. BEDTools: the Swiss army tool for genome feature analysis. *Current protocols in bioinformatics*, doi:10.1002/0471250953.bi1112s47 (2014).

46 Hansen, K. D., Irizarry, R. A. & Wu, Z. Removing technical variability in RNA-seq data using conditional quantile normalization. *Biostatistics* (Oxford, England) 13, 204-216, doi:10.1093/biostatistics/kxr054 (2012).
47 Love, M. I., Huber, W. & Anders, S. Moderated estimation of fold change and dispersion for RNA-seq data with DESeq2. *Genome biology* 15, 550, doi:10.1186/s13059-014-0550-8 (2014).
48 Dobin, A. et al. STAR: ultrafast universal RNA-seq aligner. *Bioinformatics* (Oxford, England) 29, 15-21, doi: 10.1093/bioinformatics/bts635 (2013).
49 Reimand, J., Kull, M., Peterson, H., Hansen, J. & Vilo, J. g:Profiler—a web-based toolset for functional profiling of gene lists from large-scale experiments. *Nucleic acids research* 35, 200, doi:10.1093/nar/gkm226 (2007).
50 Reimand, J. et al. g:Profiler-a web server for functional interpretation of gene lists (2016 update). *Nucleic acids research* 44, 9, doi:10.1093/nar/gkw199 (2016).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of delivering a polynucleotide to an individual, the method comprising providing to the individual a composition comprising a polynucleotide encoding a mutated variant of Yes-associated protein (Yap), wherein the polynucleotide comprises SEQ ID NO: 1, wherein lysine is substituted with arginine at position 280 of SEQ ID NO: 1.

2. The method of claim 1, wherein the individual has a cardiac condition selected from the group consisting of heart disease, cardiomyopathy, heart valve problems, pericarditis, arrhythmia, cardiac arrest, congenital heart defect, heart failure, cardiac disease, cardiotoxicity, congestive heart failure, ischemic heart disease, acute myocardial infarction, atrial fibrillation, coronary artery disease, ischemic heart disease, valvular heart disease, hypertensive heart disease, and arrhythmias.

3. The method of claim 1, wherein the individual has Duchenne muscular dystrophy.

4. The method of claim 1, wherein the composition is provided to the individual more than once.

5. The method of claim 1, wherein the composition is provided to the individual systemically.

6. The method of claim 1, wherein the composition is provided to the individual locally.

7. The method of claim 1, wherein the individual is provided an additional therapy for a condition.

* * * * *

SEQUENCE LISTING

<160> NUMBER OF SEQ ID NOS: 6

<210> SEQ ID NO 1
<211> LENGTH: 488
<212> TYPE: PRT
<213> ORGANISM: Artificial Sequence
<220> FEATURE:
<223> OTHER INFORMATION: Synthetic protein

<400> SEQUENCE: 1

```
Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Pro Ser Gly
                20                  25                  30

Pro Gly Gln Pro Ala Pro Ala Ala Thr Gln Ala Ala Pro Gln Ala Pro
            35                  40                  45

Pro Ala Gly His Gln Ile Val His Val Arg Gly Asp Ser Glu Thr Asp
        50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
    210                 215                 220

Met Asn Ser Ala Ser Gly Pro Leu Pro Asp Gly Trp Glu Gln Ala Met
```

```
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
                260                 265                 270

Ile Ser Gln Ser Ala Pro Val Lys Gln Pro Pro Leu Ala Pro Gln
                275                 280                 285

Ser Pro Gln Gly Gly Val Met Gly Gly Ser Asn Ser Asn Gln Gln Gln
            290                 295                 300

Gln Met Arg Leu Gln Gln Leu Gln Met Glu Lys Glu Arg Leu Arg Leu
305                 310                 315                 320

Lys Gln Gln Glu Leu Leu Arg Gln Glu Leu Ala Leu Arg Ser Gln Leu
                325                 330                 335

Pro Thr Leu Glu Gln Asp Gly Gly Thr Gln Asn Pro Val Ser Ser Pro
                340                 345                 350

Gly Met Ser Gln Glu Leu Arg Thr Met Thr Thr Asn Ser Ser Asp Pro
            355                 360                 365

Phe Leu Asn Ser Gly Thr Tyr His Ser Arg Asp Glu Ser Thr Asp Ser
    370                 375                 380

Gly Leu Ser Met Ser Ser Tyr Ser Val Pro Arg Thr Pro Asp Asp Phe
385                 390                 395                 400

Leu Asn Ser Val Asp Glu Met Asp Thr Gly Asp Thr Ile Asn Gln Ser
                405                 410                 415

Thr Leu Pro Ser Gln Gln Asn Arg Phe Pro Asp Tyr Leu Glu Ala Ile
                420                 425                 430

Pro Gly Thr Asn Val Asp Leu Gly Thr Leu Glu Gly Asp Gly Met Asn
            435                 440                 445

Ile Glu Gly Glu Glu Leu Met Pro Ser Leu Gln Glu Ala Leu Ser Ser
        450                 455                 460

Asp Ile Leu Asn Asp Met Glu Ser Val Leu Ala Ala Thr Lys Leu Asp
465                 470                 475                 480

Lys Glu Ser Phe Leu Thr Trp Leu
                485

<210> SEQ ID NO 2
<211> LENGTH: 488
<212> TYPE: PRT
<213> ORGANISM: Artificial Sequence
<220> FEATURE:
<223> OTHER INFORMATION: Synthetic protein

<400> SEQUENCE: 2

Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Pro Ser Gly
                20                  25                  30

Pro Gly Gln Pro Ala Pro Ala Ala Thr Gln Ala Ala Pro Gln Ala Pro
            35                  40                  45

Pro Ala Gly His Gln Ile Val His Val Arg Gly Asp Ala Glu Thr Asp
        50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ala Thr Asp Ala
```

```
            100                 105                 110
Gly Thr Ala Gly Ala Leu Thr Pro Gln His Val Arg Ala His Ala Ala
            115                 120                 125

Pro Ala Ala Leu Gln Leu Gly Ala Val Ser Pro Gly Thr Leu Thr Pro
            130                 135                 140

Thr Gly Val Val Ser Gly Pro Ala Ala Thr Pro Thr Ala Gln His Leu
145                 150                 155                 160

Arg Gln Ala Ala Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
            195                 200                 205

Gln Met Asn Val Thr Ala Pro Thr Ser Pro Val Gln Gln Asn Met
            210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
            260                 265                 270

Ile Ser Gln Ser Ala Pro Val Lys Gln Pro Pro Leu Ala Pro Gln
            275                 280                 285

Ser Pro Gln Gly Gly Val Met Gly Gly Ser Asn Ser Asn Gln Gln Gln
            290                 295                 300

Gln Met Arg Leu Gln Gln Leu Gln Met Glu Lys Glu Arg Leu Arg Leu
305                 310                 315                 320

Lys Gln Gln Glu Leu Leu Arg Gln Glu Leu Ala Leu Arg Ser Gln Leu
                325                 330                 335

Pro Thr Leu Glu Gln Asp Gly Gly Thr Gln Asn Pro Val Ser Ser Pro
            340                 345                 350

Gly Met Ser Gln Glu Leu Arg Thr Met Thr Thr Asn Ser Ser Asp Pro
            355                 360                 365

Phe Leu Asn Ser Gly Thr Tyr His Ser Arg Asp Glu Ala Thr Asp Ser
370                 375                 380

Gly Leu Ser Met Ser Ser Tyr Ser Val Pro Arg Thr Pro Asp Asp Phe
385                 390                 395                 400

Leu Asn Ser Val Asp Glu Met Asp Thr Gly Asp Thr Ile Asn Gln Ser
                405                 410                 415

Thr Leu Pro Ser Gln Gln Asn Arg Phe Pro Asp Tyr Leu Glu Ala Ile
            420                 425                 430

Pro Gly Thr Asn Val Asp Leu Gly Thr Leu Glu Gly Asp Gly Met Asn
            435                 440                 445

Ile Glu Gly Glu Glu Leu Met Pro Ser Leu Gln Glu Ala Leu Ser Ser
            450                 455                 460

Asp Ile Leu Asn Asp Met Glu Ser Val Leu Ala Ala Thr Lys Leu Asp
465                 470                 475                 480

Lys Glu Ser Phe Leu Thr Trp Leu
                485

<210> SEQ ID NO 3
<211> LENGTH: 523
<212> TYPE: PRT
<213> ORGANISM: Artificial Sequence
```

<220> FEATURE:
<223> OTHER INFORMATION: Synthetic protein

<400> SEQUENCE: 3

```
Met Asp Tyr Lys Asp Asp Asp Lys Leu Ala Ala Asn Ser Ser
1               5                   10                  15

Leu Ala Thr Met Asp Tyr Lys Asp Asp Asp Lys Ala Arg Leu Glu
            20                  25                  30

Ser Val Pro Lys Asp Pro Gly Gln Gln Pro Pro Gln Pro Ala Pro
                35                  40                  45

Gln Gly Gln Gly Gln Pro Pro Ser Gln Pro Pro Gln Gly Gln Gly Pro
        50                  55                  60

Pro Ser Gly Pro Gly Gln Pro Ala Pro Ala Ala Thr Gln Ala Ala Pro
65                      70                  75                  80

Gln Ala Pro Pro Ala Gly His Gln Ile Val His Val Arg Gly Asp Ala
                85                  90                  95

Glu Thr Asp Leu Glu Ala Leu Phe Asn Ala Val Met Asn Pro Lys Thr
            100                 105                 110

Ala Asn Val Pro Gln Thr Val Pro Met Arg Leu Arg Lys Leu Pro Asp
                115                 120                 125

Ser Phe Phe Lys Pro Pro Glu Pro Lys Ser His Ser Arg Gln Ala Ala
130                 135                 140

Thr Asp Ala Gly Thr Ala Gly Ala Leu Thr Pro Gln His Val Arg Ala
145                 150                 155                 160

His Ala Ala Pro Ala Ala Leu Gln Leu Gly Ala Val Ser Pro Gly Thr
                165                 170                 175

Leu Thr Pro Thr Gly Val Val Ser Gly Pro Ala Ala Thr Pro Thr Ala
            180                 185                 190

Gln His Leu Arg Gln Ala Ala Phe Glu Ile Pro Asp Asp Val Pro Leu
                195                 200                 205

Pro Ala Gly Trp Glu Met Ala Lys Thr Ser Ser Gly Gln Arg Tyr Phe
            210                 215                 220

Leu Asn His Ile Asp Gln Thr Thr Thr Trp Gln Asp Pro Arg Lys Ala
225                 230                 235                 240

Met Leu Ser Gln Met Asn Val Thr Ala Pro Thr Ser Pro Pro Val Gln
                245                 250                 255

Gln Asn Met Met Asn Ser Ala Ser Gly Pro Leu Pro Asp Gly Trp Glu
            260                 265                 270

Gln Ala Met Thr Gln Asp Gly Glu Ile Tyr Tyr Ile Asn His Lys Asn
                275                 280                 285

Lys Thr Thr Ser Trp Leu Asp Pro Arg Leu Asp Pro Arg Phe Ala Met
290                 295                 300

Asn Gln Arg Ile Ser Gln Ser Ala Pro Val Lys Gln Pro Pro Pro Leu
305                 310                 315                 320

Ala Pro Gln Ser Pro Gln Gly Gly Val Met Gly Gly Ser Asn Ser Asn
                325                 330                 335

Gln Gln Gln Gln Met Arg Leu Gln Gln Leu Gln Met Glu Lys Glu Arg
            340                 345                 350

Leu Arg Leu Lys Gln Gln Glu Leu Leu Arg Gln Glu Leu Ala Leu Arg
                355                 360                 365

Ser Gln Leu Pro Thr Leu Glu Gln Asp Gly Gly Thr Gln Asn Pro Val
            370                 375                 380

Ser Ser Pro Gly Met Ser Gln Glu Leu Arg Thr Met Thr Thr Asn Ser
385                 390                 395                 400
```

```
Ser Asp Pro Phe Leu Asn Ser Gly Thr Tyr His Ser Arg Asp Glu Ala
            405                 410                 415

Thr Asp Ser Gly Leu Ser Met Ser Ser Tyr Ser Val Pro Arg Thr Pro
        420                 425                 430

Asp Asp Phe Leu Asn Ser Val Asp Glu Met Asp Thr Gly Asp Thr Ile
            435                 440                 445

Asn Gln Ser Thr Leu Pro Ser Gln Gln Asn Arg Phe Pro Asp Tyr Leu
        450                 455                 460

Glu Ala Ile Pro Gly Thr Asn Val Asp Leu Gly Thr Leu Glu Gly Asp
465                 470                 475                 480

Gly Met Asn Ile Glu Gly Glu Glu Leu Met Pro Ser Leu Gln Glu Ala
            485                 490                 495

Leu Ser Ser Asp Ile Leu Asn Asp Met Glu Ser Val Leu Ala Ala Thr
        500                 505                 510

Lys Leu Asp Lys Glu Ser Phe Leu Thr Trp Leu
            515                 520

<210> SEQ ID NO 4
<211> LENGTH: 1572
<212> TYPE: DNA
<213> ORGANISM: Artificial Sequence
<220> FEATURE:
<223> OTHER INFORMATION: Synthetic DNA

<400> SEQUENCE: 4
atggactaca aagacgatga cgacaagctt gcggccgcga attcaagctt agccaccatg      60
gactacaaag acgatgacga taaagcaagg ctcgaatcgg tacctaagga tcccgggcag     120
cagccgccgc ctcaaccggc cccccagggc caagggcagc cgccttcgca gccccccgcag    180 gggcagggcc cgccgtccgg acccgggcaa ccggcacccg cggcgaccca ggcggcgccg     240
caggcacccc ccgccgggca tcagatcgtg cacgtccgcg gggacgcgga gaccgacctg     300
gaggcgctct tcaacgccgt catgaacccc aagacggcca acgtgcccca gaccgtgccc     360
atgaggctcc ggaagctgcc cgactccttc ttcaagccgc cggagcccaa atcccactcc     420
cgacaggccg ctactgatgc aggcactgca ggagccctga ctccacagca tgttcgagct     480
catgccgctc cagctgctct gcagttggga gctgtttctc ctgggacact gaccccccact    540 ggagtagtct ctggcccagc agctacaccc acagctcagc atcttcgaca ggctgctttt     600
gagatacctg atgatgtacc tctgccagca ggttgggaga tggcaaagac atcttctggt     660
cagagatact tcttaaatca catcgatcag acaacaacat ggcaggaccc caggaaggcc     720
atgctgtccc agatgaacgt cacagccccc accagtccac cagtgcagca gaatatgatg     780
aactcggctt caggtcctct tcctgatgga tgggaacaag ccatgactca ggatggagaa     840
atttactata taaaccataa gaacaagacc acctcttggc tagacccaag gcttgaccct     900
cgttttgcca tgaaccagag aatcagtcag agtgctccag tgaaacagcc accacccctg     960
gctccccaga gcccacaggg aggcgtcatg ggtggcagca actccaacca gcagcaacag    1020
atgcgactgc agcaactgca gatggagaag gagaggctgc ggctgaaaca gcaagaactg    1080
cttcggcagg agttagccct gcgtagccag ttaccaacac tggagcagga tgtgggact    1140 caaaatccag tgtcttctcc cgggatgtct caggaattga gaacaatgac gaccaatagc    1200
tcagatcctt tccttaacag tggcacctat cactctcgag atgaggctac agacagtgga    1260
ctaagcatga gcagctacag tgtccctcga accccagatg acttcctgaa cagtgtggat    1320
```

```
gagatggata caggtgatac tatcaaccaa agcaccctgc cctcacagca gaaccgtttc    1380
ccagactacc ttgaagccat tcctgggaca aatgtggacc ttggaacact ggaaggagat    1440
ggaatgaaca tagaaggaga ggagctgatg ccaagtctgc aggaagcttt gagttctgac    1500
atccttaatg acatggagtc tgttttggct gccaccaagc tagataaaga aagctttctt    1560
acatggttat ag                                                        1572

<210> SEQ ID NO 5
<211> LENGTH: 20
<212> TYPE: PRT
<213> ORGANISM: Artificial Sequence
<220> FEATURE:
<223> OTHER INFORMATION: Synthetic primer

<400> SEQUENCE: 5

Ala Ala Gly Cys Cys Thr Thr Gly Ala Cys Thr Gly Ala Gly Gly
1               5                   10                  15

Thr Thr Ala Gly
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic primer

<400> SEQUENCE: 6

Cys Gly Thr Cys Ala Thr Cys Gly Thr Cys Thr Thr Thr Gly Thr Ala
1               5                   10                  15

Gly Thr Cys Cys
            20
```